US010316084B2

(12) United States Patent
Polson et al.

(10) Patent No.: US 10,316,084 B2
(45) Date of Patent: Jun. 11, 2019

(54) ANTI-LGR5 ANTIBODIES AND USES THEREOF

(71) Applicant: GENENTECH, INC., South San Francisco, CA (US)

(72) Inventors: Andrew G. Polson, San Francisco, CA (US); Weiguang Mao, San Mateo, CA (US); Ron Firestein, Burlingame, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 15/363,045

(22) Filed: Nov. 29, 2016

(65) Prior Publication Data
US 2017/0233471 A1 Aug. 17, 2017

Related U.S. Application Data

(63) Continuation of application No. PCT/US2015/035111, filed on Jun. 10, 2015.

(60) Provisional application No. 62/010,637, filed on Jun. 11, 2014.

(51) Int. Cl.
*C07K 16/28* (2006.01)
*C07K 16/30* (2006.01)
*G01N 33/574* (2006.01)
*G01N 33/58* (2006.01)
*A61K 39/395* (2006.01)
*A61K 39/00* (2006.01)

(52) U.S. Cl.
CPC .......... *C07K 16/28* (2013.01); *C07K 16/3046* (2013.01); *G01N 33/574* (2013.01); *G01N 33/57492* (2013.01); *A61K 39/39558* (2013.01); *A61K 2039/5152* (2013.01); *C07K 2317/56* (2013.01); *C07K 2317/565* (2013.01); *C07K 2317/70* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 5,686,578 A | * | 11/1997 | Goldenberg | A61K 51/1084 530/387.3 |
| 9,175,089 B2 | * | 11/2015 | Hongo | C07K 16/30 |
| 2005/0276812 A1 | | 12/2005 | Ebens et al. | |
| 2011/0076287 A1 | | 3/2011 | Cohen et al. | |
| 2011/0256157 A1 | | 10/2011 | Howard et al. | |
| 2013/0336885 A1 | * | 12/2013 | Hongo | C07K 16/30 424/1.49 |

FOREIGN PATENT DOCUMENTS

| | | |
|---|---|---|
| DE | 10339820 | 3/2005 |
| EP | 2216344 | 8/2010 |
| WO | 2009/005809 | 1/2009 |
| WO | 2010/016766 | 2/2010 |
| WO | 2013/149159 A1 | 10/2013 |

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
George et al., Circulation. 1998; 97: 900-906.*
Alley et al., "Antibody-drug conjugates: targeted drug delivery for cancer" Current Opinion in Chemical Biology 14:529-537 (2010).
de Lau et al., "Lgr5 homologues associate with Wnt receptors and mediate R-spondin signalling" Nature 476(7360):293-297 (2011).
Gao et al., "Lgr5 over-expression is positively related to the tumor progression and HER2 expression in stage pTNM IV colorectal cancer" Int J Clin Exp Pathol 7(4):1572-1579 (2014).
Iyer et al., "Antibody drug conjugates—Trojan horses in the war on cancer" Journal of Pharmacological and Toxicological Methods 64:207-212 (2011).
Morita et al., "Neonatal Lethality of LGR5 Null Mice is Associate with Ankyloglossia and Gastrointestinal Distension" Mol Cell Biol 24(22):9736-9743 (2004).
Notification of Transmittal of the International Search Report and the Written Opinion of the International Searching Authority, or the Declaration, pp. 19 (dated Aug. 12, 2013).
Notification of Transmittal of the International Search Report and the Written Opinion of the International Searching Authority, or the Declaration, pp. 17 (dated Oct. 30, 2015).
Plaks et al., "Lgr5-expressing cells are sufficient and necessary for postnatal mammary gland organogenesis" Cell Rep 3(1):70-78 (2013).
Ricart et al., "Technology Insight: cytotoxic drug immunoconjugates for cancer therapy" Nature Clinical Practice 4(4):245-255 (2007).
Sasaki et al., "Establishment of a novel monoclonal antibody against LGR5" Biochem Biophys Res Comm 394:498-502 (2010).
Takahashi et al., "Significance of Lgr5+ve Cancer Stem Cells in the Colon and Rectum" Annals of Surgical Oncology 18(4):1166-1174 (2011).
Tian et al., "A reserve stem cell population in small intestine renders Lgr5-positive cells dispensable" Nature 478(7368):255-259 (2011).
Walker et al., "LGR5 Is a Negative Regulator of Tumourigenicity, Antagonizes Wnt Signalling and Regulates Cell Adhesion in Colorectal Cancer Cell Lines" PLoS One 6(7):e22733 (2011).
Wu et al., "Lgr5 is a potential marker of colorectal carcinoma stem cells that correlates with patient survival" World Journal of Surgical Oncology 10(1):244 (2012).

* cited by examiner

*Primary Examiner* — Hong Sang
(74) *Attorney, Agent, or Firm* — McNeill Baur PLLC

(57) ABSTRACT

The invention provides anti-LgR5 antibodies and methods of using the same.

33 Claims, 8 Drawing Sheets
Specification includes a Sequence Listing.

FIG. 4B

| Kabat number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 35a | 36 | 37 | 38 | 39 | 40 | 41 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| GEN89.LGR5.1-12 | Q | S | L | E | E | S | G | G | G | L | V | Q | P | E | G | S | L | T | L | T | C | T | A | S | G | F | S | F | S | R | T | Y | W | I | C | . | W | D | R | Q | A | P |
| GEN89.LGR5.26-1 | Q | S | L | E | E | S | G | G | D | L | V | K | . | P | G | G | T | L | T | L | T | C | T | A | S | G | I | D | F | S | Y | Y | S | Y | M | C | W | V | R | Q | A | P |

CDR H1 – Contact (26–33); CDR H1 – Kabat (31–35B)

| Kabat number | 42 | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| GEN89.LGR5.1-12 | G | K | G | L | E | W | I | A | C | I | Y | A | G | G | S | D | N | T | Y | Y | A | S | W | A | K | G | R | F | T | I | S | K | T | S | S | T | T | V | T | L | Q | V |
| GEN89.LGR5.26-1 | G | K | G | L | E | W | I | A | C | I | Y | A | G | T | S | G | S | T | Y | Y | A | S | W | A | K | G | R | F | T | I | S | K | T | S | S | T | T | V | T | L | Q | M |

CDR H2 – Contact; CDR H2 – Kabat

| Kabat number | 82a | 82b | 82c | 83 | 84 | 85 | 86 | 87 | 88 | 89 | 90 | 91 | 92 | 93 | 94 | 95 | 96 | 97 | 98 | 99 | 100 | 100a | 100b | 100c | 100d | 100e | 100f | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|---|---|---|---|---|---|---|---|---|---|---|---|---|---|---|---|---|---|---|
| GEN89.LGR5.1-12 | T | S | L | T | A | A | D | T | A | T | Y | F | C | A | R | Y | Y | A | G | S | E | Y | F | . | . | . | . | N | L | W | G | P | G | T | L | V | T | V | S | S |
| GEN89.LGR5.26-1 | I | S | L | T | A | A | D | T | A | T | Y | F | C | A | R | S | Y | Y | T | F | G | V | N | G | Y | A | W | D | L | W | G | P | G | T | L | V | T | V | S | S |

CDR H3 – Contact; CDR H3 – Kabat

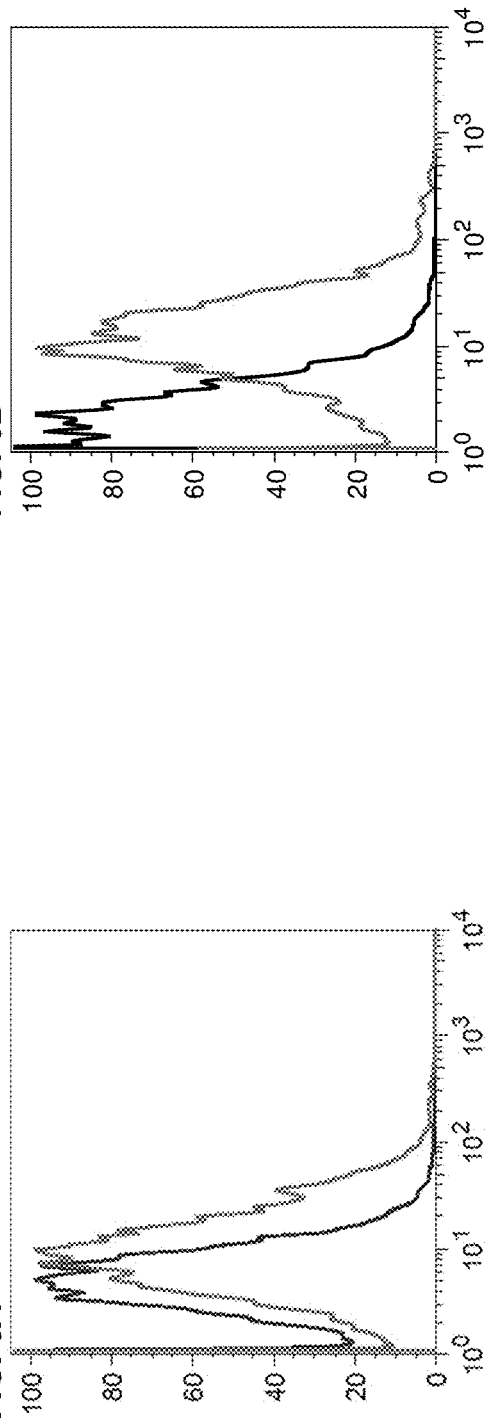
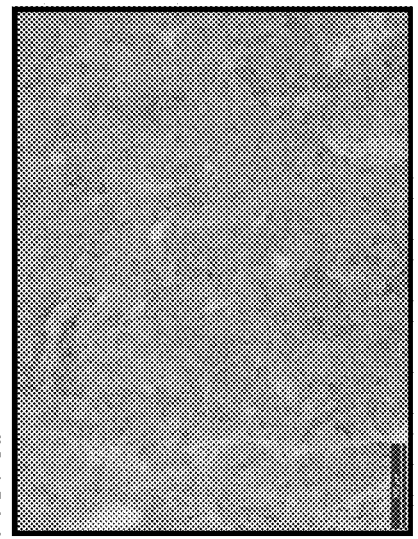
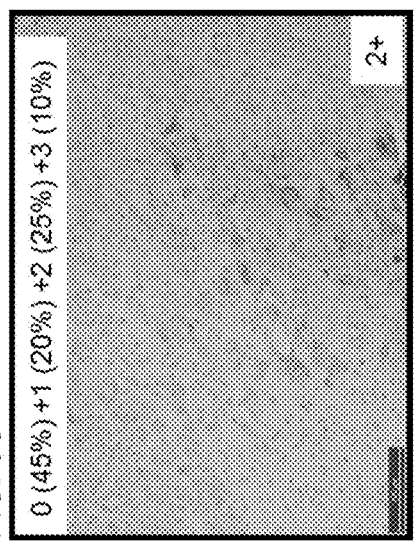
FIG. 6A
FIG. 6B
FIG. 6C
FIG. 6D

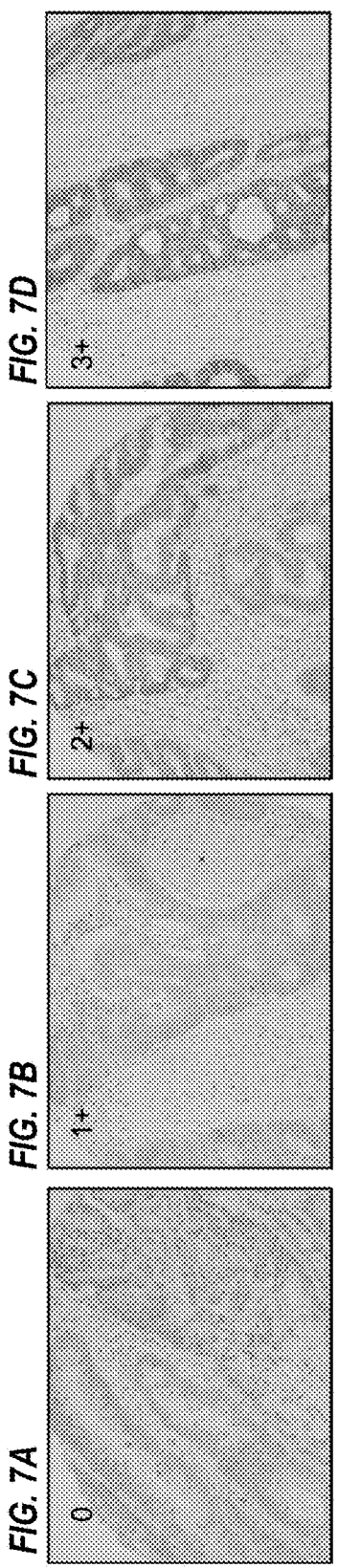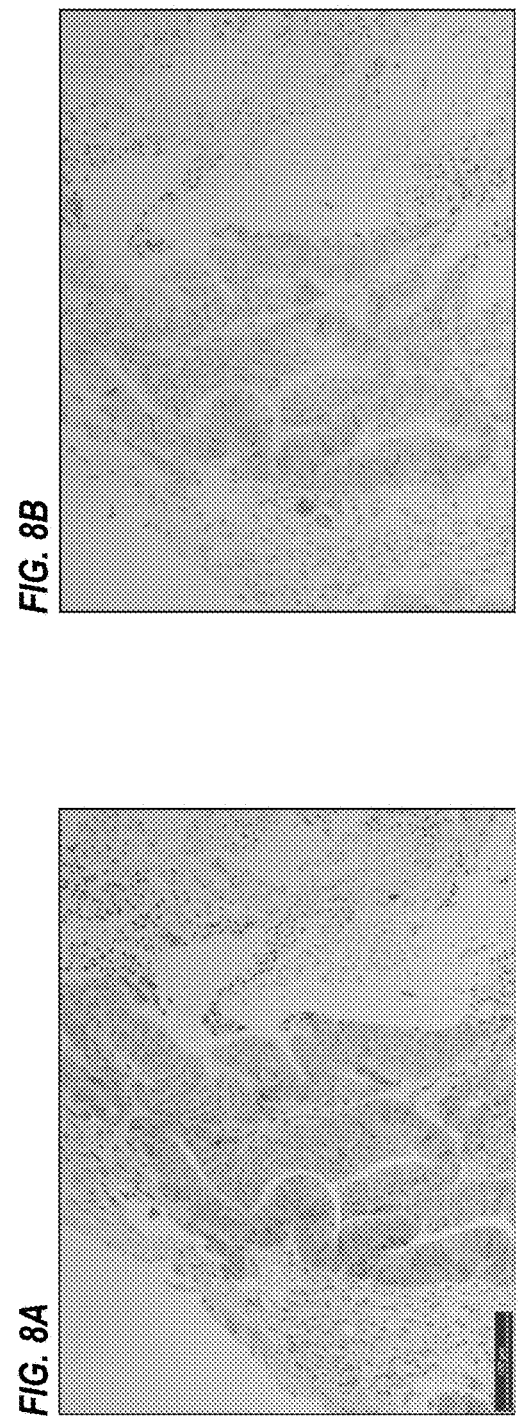

SEQUENCE LISTING

<160> NUMBER OF SEQ ID NOS: 96

<210> SEQ ID NO 1
<211> LENGTH: 216
<212> TYPE: PRT
<213> ORGANISM: Oryctolagus cuniculus

<400> SEQUENCE: 1

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Gly Ser Asn
            20                  25                  30

Leu Ala Trp Tyr Gln Gln Lys Pro Gly Gln Pro Pro Lys Leu Leu Ile
        35                  40                  45

Tyr Gly Ala Ser Asn Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Thr Tyr Gly Ser Ser Ser
                85                  90                  95

Asp Gly Phe Phe Trp Thr Phe Gly Gly Gly Thr Glu Val Val Val Lys
            100                 105                 110

Gly Asp Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215
```

<210> SEQ ID NO 2
<211> LENGTH: 443
<212> TYPE: PRT
<213> ORGANISM: Oryctolagus cuniculus

<400> SEQUENCE: 2

```
Gln Ser Leu Glu Glu Ser Gly Gly Gly Leu Val Gln Pro Glu Gly Ser
1               5                   10                  15

Leu Thr Leu Thr Cys Thr Ala Ser Gly Phe Ser Phe Ser Arg Thr Tyr
                20                  25                  30

Trp Ile Cys Trp Asp Arg Gln Ala Pro Gly Lys Gly Leu Glu Trp Ile
            35                  40                  45

Ala Cys Ile Tyr Ala Gly Gly Ser Asp Asn Thr Tyr Tyr Ala Ser Trp
50                      55                  60

Ala Lys Gly Arg Phe Thr Ile Ser Lys Thr Ser Ser Thr Thr Val Thr
65                  70                  75                  80

Leu Gln Val Thr Ser Leu Thr Ala Ala Asp Thr Ala Thr Tyr Phe Cys
                85                  90                  95

Ala Arg Tyr Tyr Ala Gly Ser Ser Glu Tyr Phe Asn Leu Trp Gly Pro
            100                 105                 110

Gly Thr Leu Val Thr Val Ser Ser Ala Ser Thr Lys Gly Pro Ser Val
        115                 120                 125

Phe Pro Leu Ala Pro Cys Cys Gly Asp Thr Pro Ser Ser Thr Val Thr
    130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
            180                 185                 190

Ser Ser Ser Gln Pro Val Thr Cys Asn Val Ala His Pro Ala Thr Asn
        195                 200                 205

Thr Lys Val Asp Lys Thr Val Ala Pro Ser Thr Cys Ser Lys Pro Thr
    210                 215                 220

Cys Pro Pro Pro Glu Leu Leu Gly Gly Pro Ser Val Phe Ile Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser Gln Asp Asp Pro Glu Val Gln Phe Thr
        260                 265                 270

Trp Tyr Ile Asn Asn Glu Gln Val Arg Thr Ala Arg Pro Pro Leu Arg
    275                 280                 285

Glu Gln Gln Phe Asn Ser Thr Ile Arg Val Val Ser Thr Leu Pro Ile
290                 295                 300

Ala His Gln Asp Trp Leu Arg Gly Lys Glu Phe Lys Cys Lys Val His
305                 310                 315                 320

Asn Lys Ala Leu Pro Ala Pro Ile Glu Lys Thr Ile Ser Lys Ala Arg
            325                 330                 335

Gly Gln Pro Leu Glu Pro Lys Val Tyr Thr Met Gly Pro Pro Arg Glu
        340                 345                 350

Glu Leu Ser Ser Arg Ser Val Ser Leu Thr Cys Met Ile Asn Gly Phe
    355                 360                 365

Tyr Pro Ser Asp Ile Ser Val Glu Trp Glu Lys Asn Gly Lys Ala Glu
370                 375                 380

Asp Asn Tyr Lys Thr Thr Pro Ala Val Leu Asp Ser Asp Gly Ser Tyr
385                 390                 395                 400

Phe Leu Tyr Ser Lys Leu Ser Val Pro Thr Ser Glu Trp Gln Arg Gly
            405                 410                 415

Asp Val Phe Thr Cys Ser Val Met His Glu Ala Leu His Asn His Tyr
```

```
                    420               425               430

Thr Gln Lys Ser Ile Ser Arg Ser Pro Gly Lys
        435                 440

<210> SEQ ID NO 3
<211> LENGTH: 214
<212> TYPE: PRT
<213> ORGANISM: Oryctolagus cuniculus

<400> SEQUENCE: 3

Ala Phe Glu Leu Thr Gln Thr Pro Ser Ser Val Glu Ala Ala Val Gly
1               5                   10                  15

Gly Thr Val Thr Ile Lys Cys Gln Ala Ser Gln Ser Ile Ser Val Gly
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Arg Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Asp Ser Ser Thr
                85                  90                  95

Thr Ala Asn Val Phe Gly Gly Gly Thr Glu Val Val Val Lys Gly Asp
            100                 105                 110

Pro Val Ala Pro Thr Val Leu Ile Phe Pro Pro Ala Ala Asp Gln Val
        115                 120                 125

Ala Thr Gly Thr Val Thr Ile Val Cys Val Ala Asn Lys Tyr Phe Pro
    130                 135                 140

Asp Val Thr Val Thr Trp Glu Val Asp Gly Thr Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
            180                 185                 190

Glu Tyr Thr Cys Lys Val Thr Gln Gly Thr Thr Ser Val Val Gln Ser
        195                 200                 205

Phe Asn Arg Gly Asp Cys
    210

<210> SEQ ID NO 4
<211> LENGTH: 446
<212> TYPE: PRT
<213> ORGANISM: Oryctolagus cuniculus

<400> SEQUENCE: 4

Gln Ser Leu Glu Glu Ser Gly Gly Asp Leu Val Lys Pro Gly Gly Thr
1               5                   10                  15

Leu Thr Leu Thr Cys Thr Ala Ser Gly Ile Asp Phe Ser Tyr Tyr Ser
            20                  25                  30

Tyr Met Cys Trp Val Arg Gln Ala Pro Gly Lys Gly Leu Glu Trp Ile
        35                  40                  45

Ala Cys Ile Tyr Ala Gly Thr Gly Ser Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Met Ile Ser Leu Thr Ala Ala Asp Thr Ala Thr Tyr Phe Cys
```

```
              85                  90                  95
Ala Arg Ser Tyr Tyr Thr Phe Gly Val Asn Gly Tyr Ala Trp Asp Leu
            100                 105                 110

Trp Gly Pro Gly Thr Leu Val Thr Val Ser Ser Ala Ser Thr Lys Gly
        115                 120                 125

Pro Ser Val Phe Pro Leu Ala Pro Cys Cys Gly Asp Thr Pro Ser Ser
    130                 135                 140

Thr Val Thr Leu Gly Cys Leu Val Lys Gly Tyr Leu Pro Glu Pro Val
145                 150                 155                 160

Thr Val Thr Trp Asn Ser Gly Thr Leu Thr Asn Gly Val Arg Thr Phe
                165                 170                 175

Pro Ser Val Arg Gln Ser Ser Gly Leu Tyr Ser Leu Ser Ser Val Val
            180                 185                 190

Ser Val Thr Ser Ser Ser Gln Pro Val Thr Cys Asn Val Ala His Pro
        195                 200                 205

Ala Thr Asn Thr Lys Val Asp Lys Thr Val Ala Pro Ser Thr Cys Ser
    210                 215                 220

Lys Pro Thr Cys Pro Pro Pro Glu Leu Leu Gly Gly Pro Ser Val Phe
225                 230                 235                 240

Ile Phe Pro Pro Lys Pro Lys Asp Thr Leu Met Ile Ser Arg Thr Pro
                245                 250                 255

Glu Val Thr Cys Val Val Val Asp Val Ser Gln Asp Asp Pro Glu Val
            260                 265                 270

Gln Phe Thr Trp Tyr Ile Asn Asn Glu Gln Val Arg Thr Ala Arg Pro
        275                 280                 285

Pro Leu Arg Glu Gln Gln Phe Asn Ser Thr Ile Arg Val Val Ser Thr
    290                 295                 300

Leu Pro Ile Ala His Gln Asp Trp Leu Arg Gly Lys Glu Phe Lys Cys
305                 310                 315                 320

Lys Val His Asn Lys Ala Leu Pro Ala Pro Ile Glu Lys Thr Ile Ser
                325                 330                 335

Lys Ala Arg Gly Gln Pro Leu Glu Pro Lys Val Tyr Thr Met Gly Pro
            340                 345                 350

Pro Arg Glu Glu Leu Ser Ser Arg Ser Val Ser Leu Thr Cys Met Ile
        355                 360                 365

Asn Gly Phe Tyr Pro Ser Asp Ile Ser Val Glu Trp Glu Lys Asn Gly
    370                 375                 380

Lys Ala Glu Asp Asn Tyr Lys Thr Thr Pro Ala Val Leu Asp Ser Asp
385                 390                 395                 400

Gly Ser Tyr Phe Leu Tyr Ser Lys Leu Ser Val Pro Thr Ser Glu Trp
                405                 410                 415

Gln Arg Gly Asp Val Phe Thr Cys Ser Val Met His Glu Ala Leu His
            420                 425                 430

Asn His Tyr Thr Gln Lys Ser Ile Ser Arg Ser Pro Gly Lys
        435                 440                 445

<210> SEQ ID NO 5
<211> LENGTH: 112
<212> TYPE: PRT
<213> ORGANISM: Oryctolagus cuniculus

<400> SEQUENCE: 5

Ala Tyr Asp Met Thr Gln Thr Pro Ala Ser Val Glu Val Ala Val Gly
1               5                   10                  15
```

Gly Thr Val Thr Ile Lys Cys Gln Ala Ser Gln Ser Ile Ser Asn
            20                  25                  30

Leu Ala Trp Tyr Gln Gln Lys Pro Gly Gln Pro Pro Lys Leu Leu Ile
        35                  40                  45

Tyr Gly Ala Ser Asn Leu Ala Ser Gly Val Ser Ser Arg Phe Lys Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Gln Thr Thr Tyr Gly Ser Ser Ser
                85                  90                  95

Asp Gly Phe Phe Trp Thr Phe Gly Gly Gly Thr Glu Val Val Val Lys
            100                 105                 110

<210> SEQ ID NO 6
<211> LENGTH: 120
<212> TYPE: PRT
<213> ORGANISM: Oryctolagus cuniculus

<400> SEQUENCE: 6

Gln Ser Leu Glu Glu Ser Gly Gly Gly Leu Val Gln Pro Glu Gly Ser
1               5                   10                  15

Leu Thr Leu Thr Cys Thr Ala Ser Gly Phe Ser Phe Ser Arg Thr Tyr
            20                  25                  30

Trp Ile Cys Trp Asp Arg Gln Ala Pro Gly Lys Gly Leu Glu Trp Ile
        35                  40                  45

Ala Cys Ile Tyr Ala Gly Gly Ser Asp Asn Thr Tyr Tyr Ala Ser Trp
    50                  55                  60

Ala Lys Gly Arg Phe Thr Ile Ser Lys Thr Ser Ser Thr Thr Val Thr
65                  70                  75                  80

Leu Gln Val Thr Ser Leu Thr Ala Ala Asp Thr Ala Thr Tyr Phe Cys
                85                  90                  95

Ala Arg Tyr Tyr Ala Gly Ser Ser Glu Tyr Phe Asn Leu Trp Gly Pro
            100                 105                 110

Gly Thr Leu Val Thr Val Ser Ser
        115                 120

<210> SEQ ID NO 7
<211> LENGTH: 110
<212> TYPE: PRT
<213> ORGANISM: Oryctolagus cuniculus

<400> SEQUENCE: 7

Ala Phe Glu Leu Thr Gln Thr Pro Ser Ser Val Glu Ala Ala Val Gly
1               5                   10                  15

Gly Thr Val Thr Ile Lys Cys Gln Ala Ser Gln Ser Ile Ser Val Gly
            20                  25                  30

Leu Ala Trp Tyr Gln Gln Lys Pro Gly Gln Pro Pro Lys Leu Leu Ile
        35                  40                  45

Tyr Lys Ala Ser Thr Leu Ala Ser Gly Val Pro Ser Arg Phe Lys Gly
    50                  55                  60

Ser Arg Ser Gly Thr Glu Phe Thr Leu Thr Ile Ser Asp Leu Glu Cys
65                  70                  75                  80

Ala Asp Ala Ala Thr Tyr Tyr Cys Gln Ser Tyr Tyr Asp Ser Ser Thr
                85                  90                  95

Thr Ala Asn Val Phe Gly Gly Gly Thr Glu Val Val Val Lys
            100                 105                 110

<210> SEQ ID NO 8
<211> LENGTH: 123
<212> TYPE: PRT
<213> ORGANISM: Oryctolagus cuniculus

<400> SEQUENCE: 8

Gln Ser Leu Glu Glu Ser Gly Gly Asp Leu Val Lys Pro Gly Gly Thr
1               5                   10                  15

Leu Thr Leu Thr Cys Thr Ala Ser Gly Ile Asp Phe Ser Tyr Tyr Ser
            20                  25                  30

Tyr Met Cys Trp Val Arg Gln Ala Pro Gly Lys Gly Leu Glu Trp Ile
        35                  40                  45

Ala Cys Ile Tyr Ala Gly Thr Ser Gly Ser Thr Tyr Tyr Ala Ser Trp
    50                  55                  60

Ala Lys Gly Arg Phe Thr Ile Ser Lys Thr Ser Thr Thr Val Thr
65                  70                  75                  80

Leu Gln Met Ile Ser Leu Thr Ala Ala Asp Thr Ala Thr Tyr Phe Cys
                85                  90                  95

Ala Arg Ser Tyr Tyr Thr Phe Gly Val Asn Gly Tyr Ala Trp Asp Leu
            100                 105                 110

Trp Gly Pro Gly Thr Leu Val Thr Val Ser Ser
        115                 120

<210> SEQ ID NO 9
<211> LENGTH: 11
<212> TYPE: PRT
<213> ORGANISM: Oryctolagus cuniculus

<400> SEQUENCE: 9

Gln Ala Ser Gln Ser Ile Gly Ser Asn Leu Ala
1               5                   10

<210> SEQ ID NO 10
<211> LENGTH: 7
<212> TYPE: PRT
<213> ORGANISM: Oryctolagus cuniculus

<400> SEQUENCE: 10

Gly Ala Ser Asn Leu Ala Ser
1               5

<210> SEQ ID NO 11
<211> LENGTH: 14
<212> TYPE: PRT
<213> ORGANISM: Oryctolagus cuniculus

<400> SEQUENCE: 11

Gln Thr Thr Tyr Gly Ser Ser Ser Asp Gly Phe Phe Trp Thr
1               5                   10

<210> SEQ ID NO 12
<211> LENGTH: 6
<212> TYPE: PRT
<213> ORGANISM: Oryctolagus cuniculus

<400> SEQUENCE: 12

Arg Thr Tyr Trp Ile Cys
1               5

<210> SEQ ID NO 13
<211> LENGTH: 17

```
<212> TYPE: PRT
<213> ORGANISM: Oryctolagus cuniculus

<400> SEQUENCE: 13

Cys Ile Tyr Ala Gly Gly Ser Asp Asn Thr Tyr Tyr Ala Ser Trp Ala
1               5                   10                  15
Lys

<210> SEQ ID NO 14
<211> LENGTH: 11
<212> TYPE: PRT
<213> ORGANISM: Oryctolagus cuniculus

<400> SEQUENCE: 14

Tyr Tyr Ala Gly Ser Ser Glu Tyr Phe Asn Leu
1               5                   10

<210> SEQ ID NO 15
<211> LENGTH: 11
<212> TYPE: PRT
<213> ORGANISM: Oryctolagus cuniculus

<400> SEQUENCE: 15

Gln Ala Ser Gln Ser Ile Ser Val Gly Leu Ala
1               5                   10

<210> SEQ ID NO 16
<211> LENGTH: 7
<212> TYPE: PRT
<213> ORGANISM: Oryctolagus cuniculus

<400> SEQUENCE: 16

Lys Ala Ser Thr Leu Ala Ser
1               5

<210> SEQ ID NO 17
<211> LENGTH: 12
<212> TYPE: PRT
<213> ORGANISM: Oryctolagus cuniculus

<400> SEQUENCE: 17

Gln Ser Tyr Tyr Asp Ser Ser Thr Thr Ala Asn Val
1               5                   10

<210> SEQ ID NO 18
<211> LENGTH: 6
<212> TYPE: PRT
<213> ORGANISM: Oryctolagus cuniculus

<400> SEQUENCE: 18

Tyr Tyr Ser Tyr Met Cys
1               5

<210> SEQ ID NO 19
<211> LENGTH: 17
<212> TYPE: PRT
<213> ORGANISM: Oryctolagus cuniculus

<400> SEQUENCE: 19

Cys Ile Tyr Ala Gly Thr Ser Gly Ser Thr Tyr Tyr Ala Ser Trp Ala
1               5                   10                  15
Lys
```

```
<210> SEQ ID NO 20
<211> LENGTH: 14
<212> TYPE: PRT
<213> ORGANISM: Oryctolagus cuniculus

<400> SEQUENCE: 20

Ser Tyr Tyr Thr Phe Gly Val Asn Gly Tyr Ala Trp Asp Leu
1               5                   10

<210> SEQ ID NO 21
<211> LENGTH: 907
<212> TYPE: PRT
<213> ORGANISM: Homo sapiens

<400> SEQUENCE: 21

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
    290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
```

-continued

```
                325                 330                 335
Gly Ala Gln Ile Ser Ser Leu Pro Gln Thr Val Cys Asn Gln Leu Pro
            340                 345                 350
Asn Leu Gln Val Leu Asp Leu Ser Tyr Asn Leu Leu Glu Asp Leu Pro
            355                 360                 365
Ser Phe Ser Val Cys Gln Lys Leu Gln Lys Ile Asp Leu Arg His Asn
370                 375                 380
Glu Ile Tyr Glu Ile Lys Val Asp Thr Phe Gln Gln Leu Leu Ser Leu
385                 390                 395                 400
Arg Ser Leu Asn Leu Ala Trp Asn Lys Ile Ala Ile His Pro Asn
                405                 410                 415
Ala Phe Ser Thr Leu Pro Ser Leu Ile Lys Leu Asp Leu Ser Ser Asn
            420                 425                 430
Leu Leu Ser Ser Phe Pro Ile Thr Gly Leu His Gly Leu Thr His Leu
            435                 440                 445
Lys Leu Thr Gly Asn His Ala Leu Gln Ser Leu Ile Ser Ser Glu Asn
450                 455                 460
Phe Pro Glu Leu Lys Val Ile Glu Met Pro Tyr Ala Tyr Gln Cys Cys
465                 470                 475                 480
Ala Phe Gly Val Cys Glu Asn Ala Tyr Lys Ile Ser Asn Gln Trp Asn
                485                 490                 495
Lys Gly Asp Asn Ser Ser Met Asp Asp Leu His Lys Lys Asp Ala Gly
            500                 505                 510
Met Phe Gln Ala Gln Asp Glu Arg Asp Leu Glu Asp Phe Leu Leu Asp
            515                 520                 525
Phe Glu Glu Asp Leu Lys Ala Leu His Ser Val Gln Cys Ser Pro Ser
530                 535                 540
Pro Gly Pro Phe Lys Pro Cys Glu His Leu Leu Asp Gly Trp Leu Ile
545                 550                 555                 560
Arg Ile Gly Val Trp Thr Ile Ala Val Leu Ala Leu Thr Cys Asn Ala
                565                 570                 575
Leu Val Thr Ser Thr Val Phe Arg Ser Pro Leu Tyr Ile Ser Pro Ile
            580                 585                 590
Lys Leu Leu Ile Gly Val Ile Ala Ala Val Asn Met Leu Thr Gly Val
            595                 600                 605
Ser Ser Ala Val Leu Ala Gly Val Asp Ala Phe Thr Phe Gly Ser Phe
            610                 615                 620
Ala Arg His Gly Ala Trp Trp Glu Asn Gly Val Gly Cys His Val Ile
625                 630                 635                 640
Gly Phe Leu Ser Ile Phe Ala Ser Glu Ser Ser Val Phe Leu Leu Thr
                645                 650                 655
Leu Ala Ala Leu Glu Arg Gly Phe Ser Val Lys Tyr Ser Ala Lys Phe
            660                 665                 670
Glu Thr Lys Ala Pro Phe Ser Ser Leu Lys Val Ile Ile Leu Leu Cys
            675                 680                 685
Ala Leu Leu Ala Leu Thr Met Ala Ala Val Pro Leu Leu Gly Gly Ser
            690                 695                 700
Lys Tyr Gly Ala Ser Pro Leu Cys Leu Pro Leu Pro Phe Gly Glu Pro
705                 710                 715                 720
Ser Thr Met Gly Tyr Met Val Ala Leu Ile Leu Leu Asn Ser Leu Cys
                725                 730                 735
Phe Leu Met Met Thr Ile Ala Tyr Thr Lys Leu Tyr Cys Asn Leu Asp
            740                 745                 750
```

```
Lys Gly Asp Leu Glu Asn Ile Trp Asp Cys Ser Met Val Lys His Ile
            755                 760                 765

Ala Leu Leu Leu Phe Thr Asn Cys Ile Leu Asn Cys Pro Val Ala Phe
        770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Pro Leu Pro Ala Cys Leu Asn
                805                 810                 815

Pro Leu Leu Tyr Ile Leu Phe Asn Pro His Phe Lys Glu Asp Leu Val
                820                 825                 830

Ser Leu Arg Lys Gln Thr Tyr Val Trp Thr Arg Ser Lys His Pro Ser
            835                 840                 845

Leu Met Ser Ile Asn Ser Asp Asp Val Glu Lys Gln Ser Cys Asp Ser
        850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
            900                 905

<210> SEQ ID NO 22
<211> LENGTH: 886
<212> TYPE: PRT
<213> ORGANISM: Homo sapiens

<400> SEQUENCE: 22

Gly Ser Ser Pro Arg Ser Gly Val Leu Leu Arg Gly Cys Pro Thr His
1               5                   10                  15

Cys His Cys Glu Pro Asp Gly Arg Met Leu Leu Arg Val Asp Cys Ser
            20                  25                  30

Asp Leu Gly Leu Ser Glu Leu Pro Ser Asn Leu Ser Val Phe Thr Ser
        35                  40                  45

Tyr Leu Asp Leu Ser Met Asn Asn Ile Ser Gln Leu Leu Pro Asn Pro
50                  55                  60

Leu Pro Ser Leu Arg Phe Leu Glu Glu Leu Arg Leu Ala Gly Asn Ala
65                  70                  75                  80

Leu Thr Tyr Ile Pro Lys Gly Ala Phe Thr Gly Leu Tyr Ser Leu Lys
                85                  90                  95

Val Leu Met Leu Gln Asn Asn Gln Leu Arg His Val Pro Thr Glu Ala
            100                 105                 110

Leu Gln Asn Leu Arg Ser Leu Gln Ser Leu Arg Leu Asp Ala Asn His
        115                 120                 125

Ile Ser Tyr Val Pro Pro Ser Cys Phe Ser Gly Leu His Ser Leu Arg
130                 135                 140

His Leu Trp Leu Asp Asp Asn Ala Leu Thr Glu Ile Pro Val Gln Ala
145                 150                 155                 160

Phe Arg Ser Leu Ser Ala Leu Gln Ala Met Thr Leu Ala Leu Asn Lys
                165                 170                 175

Ile His His Ile Pro Asp Tyr Ala Phe Gly Asn Leu Ser Ser Leu Val
            180                 185                 190

Val Leu His Leu His Asn Asn Arg Ile His Ser Leu Gly Lys Lys Cys
        195                 200                 205

Phe Asp Gly Leu His Ser Leu Glu Thr Leu Asp Leu Asn Tyr Asn Asn
```

```
                210                 215                 220

Leu Asp Glu Phe Pro Thr Ala Ile Arg Thr Leu Ser Asn Leu Lys Glu
225                 230                 235                 240

Leu Gly Phe His Ser Asn Asn Ile Arg Ser Ile Pro Glu Lys Ala Phe
                245                 250                 255

Val Gly Asn Pro Ser Leu Ile Thr Ile His Phe Tyr Asp Asn Pro Ile
                260                 265                 270

Gln Phe Val Gly Arg Ser Ala Phe Gln His Leu Pro Glu Leu Arg Thr
                275                 280                 285

Leu Thr Leu Asn Gly Ala Ser Gln Ile Thr Glu Phe Pro Asp Leu Thr
        290                 295                 300

Gly Thr Ala Asn Leu Glu Ser Leu Thr Leu Thr Gly Ala Gln Ile Ser
305                 310                 315                 320

Ser Leu Pro Gln Thr Val Cys Asn Gln Leu Pro Asn Leu Gln Val Leu
                325                 330                 335

Asp Leu Ser Tyr Asn Leu Leu Glu Asp Leu Pro Ser Phe Ser Val Cys
                340                 345                 350

Gln Lys Leu Gln Lys Ile Asp Leu Arg His Asn Glu Ile Tyr Glu Ile
                355                 360                 365

Lys Val Asp Thr Phe Gln Gln Leu Leu Ser Leu Arg Ser Leu Asn Leu
        370                 375                 380

Ala Trp Asn Lys Ile Ala Ile His Pro Asn Ala Phe Ser Thr Leu
385                 390                 395                 400

Pro Ser Leu Ile Lys Leu Asp Leu Ser Ser Asn Leu Leu Ser Ser Phe
                405                 410                 415

Pro Ile Thr Gly Leu His Gly Leu Thr His Leu Lys Leu Thr Gly Asn
                420                 425                 430

His Ala Leu Gln Ser Leu Ile Ser Ser Glu Asn Phe Pro Glu Leu Lys
                435                 440                 445

Val Ile Glu Met Pro Tyr Ala Tyr Gln Cys Cys Ala Phe Gly Val Cys
                450                 455                 460

Glu Asn Ala Tyr Lys Ile Ser Asn Gln Trp Asn Lys Gly Asp Asn Ser
465                 470                 475                 480

Ser Met Asp Asp Leu His Lys Lys Asp Ala Gly Met Phe Gln Ala Gln
                485                 490                 495

Asp Glu Arg Asp Leu Glu Asp Phe Leu Leu Asp Phe Glu Glu Asp Leu
                500                 505                 510

Lys Ala Leu His Ser Val Gln Cys Ser Pro Ser Pro Gly Pro Phe Lys
                515                 520                 525

Pro Cys Glu His Leu Leu Asp Gly Trp Leu Ile Arg Ile Gly Val Trp
        530                 535                 540

Thr Ile Ala Val Leu Ala Leu Thr Cys Asn Ala Leu Val Thr Ser Thr
545                 550                 555                 560

Val Phe Arg Ser Pro Leu Tyr Ile Ser Pro Ile Lys Leu Leu Ile Gly
                565                 570                 575

Val Ile Ala Ala Val Asn Met Leu Thr Gly Val Ser Ser Ala Val Leu
                580                 585                 590

Ala Gly Val Asp Ala Phe Thr Phe Gly Ser Phe Ala Arg His Gly Ala
                595                 600                 605

Trp Trp Glu Asn Gly Val Gly Cys His Val Ile Gly Phe Leu Ser Ile
        610                 615                 620

Phe Ala Ser Glu Ser Ser Val Phe Leu Leu Thr Leu Ala Ala Leu Glu
625                 630                 635                 640
```

Arg Gly Phe Ser Val Lys Tyr Ser Ala Lys Phe Glu Thr Lys Ala Pro
            645                 650                 655

Phe Ser Ser Leu Lys Val Ile Ile Leu Leu Cys Ala Leu Leu Ala Leu
            660                 665                 670

Thr Met Ala Ala Val Pro Leu Leu Gly Gly Ser Lys Tyr Gly Ala Ser
            675                 680                 685

Pro Leu Cys Leu Pro Leu Pro Phe Gly Glu Pro Ser Thr Met Gly Tyr
            690                 695                 700

Met Val Ala Leu Ile Leu Leu Asn Ser Leu Cys Phe Leu Met Met Thr
705                 710                 715                 720

Ile Ala Tyr Thr Lys Leu Tyr Cys Asn Leu Asp Lys Gly Asp Leu Glu
            725                 730                 735

Asn Ile Trp Asp Cys Ser Met Val Lys His Ile Ala Leu Leu Leu Phe
            740                 745                 750

Thr Asn Cys Ile Leu Asn Cys Pro Val Ala Phe Leu Ser Phe Ser Ser
            755                 760                 765

Leu Ile Asn Leu Thr Phe Ile Ser Pro Glu Val Ile Lys Phe Ile Leu
            770                 775                 780

Leu Val Val Val Pro Leu Pro Ala Cys Leu Asn Pro Leu Leu Tyr Ile
785                 790                 795                 800

Leu Phe Asn Pro His Phe Lys Glu Asp Leu Val Ser Leu Arg Lys Gln
            805                 810                 815

Thr Tyr Val Trp Thr Arg Ser Lys His Pro Ser Leu Met Ser Ile Asn
            820                 825                 830

Ser Asp Asp Val Glu Lys Gln Ser Cys Asp Ser Thr Gln Ala Leu Val
            835                 840                 845

Thr Phe Thr Ser Ser Ser Ile Thr Tyr Asp Leu Pro Pro Ser Ser Val
            850                 855                 860

Pro Ser Pro Ala Tyr Pro Val Thr Glu Ser Cys His Leu Ser Ser Val
865                 870                 875                 880

Ala Phe Val Pro Cys Leu
            885

<210> SEQ ID NO 23
<211> LENGTH: 875
<212> TYPE: PRT
<213> ORGANISM: Macaca fascicularis

<400> SEQUENCE: 23

Gly Cys Pro Thr His Cys His Cys Glu Pro Asp Gly Arg Met Leu Leu
1               5                   10                  15

Arg Val Asp Cys Ser Asp Leu Gly Leu Ser Glu Leu Pro Ser Asn Leu
            20                  25                  30

Ser Val Phe Thr Ser Tyr Leu Asp Leu Ser Met Asn Asn Ile Ser Gln
            35                  40                  45

Leu Leu Pro Asn Pro Leu Pro Ser Leu Arg Phe Leu Glu Glu Leu Arg
            50                  55                  60

Leu Ala Gly Asn Ala Leu Thr Tyr Ile Pro Lys Gly Ala Phe Thr Gly
65                  70                  75                  80

Leu Tyr Ser Leu Lys Val Leu Met Leu Gln Asn Asn Gln Leu Arg Gln
            85                  90                  95

Val Pro Thr Glu Ala Leu Gln Asn Leu Arg Ser Leu Gln Ser Leu Arg
            100                 105                 110

Leu Asp Ala Asn His Ile Ser Tyr Val Pro Pro Ser Cys Phe Ser Gly

```
              115                 120                 125
Leu His Ser Leu Arg His Leu Trp Leu Asp Asp Asn Ala Leu Thr Glu
130                 135                 140

Ile Pro Val Gln Ala Phe Arg Ser Leu Ser Ala Leu Gln Ala Met Thr
145                 150                 155                 160

Leu Ala Leu Asn Lys Ile His His Ile Pro Asp Tyr Ala Phe Gly Asn
                165                 170                 175

Leu Ser Ser Leu Val Val Leu His Leu His Asn Asn Arg Ile His Ser
            180                 185                 190

Leu Gly Lys Lys Cys Phe Asp Gly Leu His Ser Leu Glu Thr Leu Asp
        195                 200                 205

Leu Asn Tyr Asn Asn Leu Asp Glu Phe Pro Thr Ala Ile Arg Thr Leu
    210                 215                 220

Ser Asn Leu Lys Glu Leu Gly Phe His Ser Asn Asn Ile Arg Ser Ile
225                 230                 235                 240

Pro Glu Lys Ala Phe Val Gly Asn Pro Ser Leu Ile Thr Ile His Phe
                245                 250                 255

Tyr Asp Asn Pro Ile Gln Phe Val Gly Arg Ser Ala Phe Gln His Leu
            260                 265                 270

Pro Glu Leu Arg Thr Leu Thr Leu Asn Gly Ala Ser Gln Ile Thr Glu
        275                 280                 285

Phe Pro Asp Leu Thr Gly Thr Ala Asn Leu Glu Ser Leu Thr Leu Thr
    290                 295                 300

Gly Ala Gln Ile Ser Ser Leu Pro Gln Thr Val Cys Asn Gln Leu Pro
305                 310                 315                 320

Asn Leu Gln Val Leu Asp Leu Ser Tyr Asn Leu Leu Glu Asp Leu Pro
                325                 330                 335

Ser Phe Ser Val Cys Gln Lys Leu Gln Lys Ile Asp Leu Arg His Asn
            340                 345                 350

Glu Ile Tyr Glu Ile Lys Val Asp Thr Phe Gln Gln Leu Leu Ser Leu
        355                 360                 365

Arg Ser Leu Asn Leu Ala Trp Asn Lys Ile Ala Ile His Pro Asn
    370                 375                 380

Ala Phe Ser Thr Leu Pro Ser Leu Ile Lys Leu Asp Leu Ser Ser Asn
385                 390                 395                 400

Leu Leu Ser Ser Phe Pro Val Thr Gly Leu His Gly Leu Thr His Leu
                405                 410                 415

Lys Leu Thr Gly Asn His Ala Leu Gln Ser Leu Ile Ser Ser Glu Asn
            420                 425                 430

Phe Pro Glu Leu Lys Ile Ile Glu Met Pro Tyr Ala Tyr Gln Cys Cys
        435                 440                 445

Ala Phe Gly Val Cys Glu Asn Ala Tyr Lys Ile Ser Asn Gln Trp Asn
    450                 455                 460

Lys Gly Asp Asn Ser Ser Met Asp Asp Leu His Lys Lys Asp Ala Gly
465                 470                 475                 480

Met Phe Gln Val Gln Asp Glu Arg Asp Leu Glu Asp Phe Leu Leu Asp
                485                 490                 495

Phe Glu Glu Asp Leu Lys Ala Leu His Ser Val Gln Cys Ser Pro Ser
            500                 505                 510

Pro Gly Pro Phe Lys Pro Cys Glu His Leu Leu Asp Gly Trp Leu Ile
        515                 520                 525

Arg Ile Gly Val Trp Thr Ile Ala Val Leu Ala Leu Thr Cys Asn Ala
    530                 535                 540
```

Leu Val Thr Ser Thr Val Phe Arg Ser Pro Leu Tyr Ile Ser Pro Ile
545                 550                 555                 560

Lys Leu Leu Ile Gly Val Ile Ala Val Val Asn Met Leu Thr Gly Val
                565                 570                 575

Ser Ser Ala Val Leu Ala Gly Val Asp Ala Phe Thr Phe Gly Ser Phe
            580                 585                 590

Ala Arg His Gly Ala Trp Trp Glu Asn Gly Val Gly Cys Gln Val Ile
        595                 600                 605

Gly Phe Leu Ser Ile Phe Ala Ser Glu Ser Ser Val Phe Leu Leu Thr
    610                 615                 620

Leu Ala Ala Leu Glu Arg Gly Phe Ser Val Lys Cys Ser Ala Lys Phe
625                 630                 635                 640

Glu Thr Lys Ala Pro Phe Ser Ser Leu Lys Val Ile Ile Leu Leu Cys
                645                 650                 655

Ala Leu Leu Ala Leu Thr Met Ala Ala Val Pro Leu Leu Gly Gly Ser
            660                 665                 670

Glu Tyr Gly Ala Ser Pro Leu Cys Leu Pro Leu Pro Phe Gly Glu Pro
        675                 680                 685

Ser Thr Thr Gly Tyr Met Val Ala Leu Ile Leu Asn Ser Leu Cys
    690                 695                 700

Phe Leu Met Met Thr Ile Ala Tyr Thr Lys Leu Tyr Cys Asn Leu Asp
705                 710                 715                 720

Lys Gly Asp Leu Glu Asn Ile Trp Asp Cys Ser Met Val Lys His Ile
                725                 730                 735

Ala Leu Leu Phe Thr Asn Cys Ile Leu Tyr Cys Pro Val Ala Phe
            740                 745                 750

Leu Ser Phe Ser Ser Leu Leu Asn Leu Thr Phe Ile Ser Pro Glu Val
        755                 760                 765

Ile Lys Phe Ile Leu Leu Val Ile Val Pro Leu Pro Ala Cys Leu Asn
    770                 775                 780

Pro Leu Leu Tyr Ile Leu Phe Asn Pro His Phe Lys Glu Asp Leu Val
785                 790                 795                 800

Ser Leu Gly Lys Gln Thr Tyr Phe Trp Thr Arg Ser Lys His Pro Ser
                805                 810                 815

Leu Met Ser Ile Asn Ser Asp Asp Val Glu Lys Gln Ser Cys Asp Ser
            820                 825                 830

Thr Gln Ala Leu Val Thr Phe Thr Ser Ser Ile Ala Tyr Asp Leu
        835                 840                 845

Pro Pro Ser Ser Val Pro Ser Pro Ala Tyr Pro Val Thr Glu Ser Cys
850                 855                 860

His Leu Ser Ser Val Ala Phe Val Pro Cys Leu
865                 870                 875

<210> SEQ ID NO 24
<211> LENGTH: 907
<212> TYPE: PRT
<213> ORGANISM: Rattus rattus

<400> SEQUENCE: 24

Met Asp Thr Ser Arg Val Arg Met Leu Leu Ser Leu Leu Ala Leu Leu
1               5                   10                  15

Gln Leu Val Ala Ala Gly Ser Pro Pro Arg Pro Asp Thr Met Pro Arg
                20                  25                  30

Gly Cys Pro Ser Tyr Cys His Cys Glu Leu Asp Gly Arg Met Leu Leu

```
             35                  40                  45
Arg Val Asp Cys Ser Asp Leu Gly Leu Ser Glu Leu Pro Ser Asn Leu
 50                  55                  60

Ser Val Phe Thr Ser Tyr Leu Asp Leu Ser Met Asn Asn Ile Ser Gln
 65                  70                  75                  80

Leu Pro Ala Ser Leu Leu His Arg Leu Arg Phe Leu Glu Glu Leu Arg
                 85                  90                  95

Leu Ala Gly Asn Ala Leu Thr His Ile Pro Lys Gly Ala Phe Ala Gly
                100                 105                 110

Leu His Ser Leu Lys Val Leu Met Leu Gln Asn Asn Gln Leu Arg Gln
                115                 120                 125

Val Pro Glu Glu Ala Leu Gln Asn Leu Arg Ser Leu Gln Ser Leu Arg
130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Asp
                165                 170                 175

Val Pro Val Gln Ala Phe Arg Ser Leu Ser Ala Leu Gln Ala Met Thr
                180                 185                 190

Leu Ala Leu Asn Lys Ile His His Ile Ala Asp His Ala Phe Gly Asn
                195                 200                 205

Leu Ser Ser Leu Val Leu His Leu His Asn Asn Arg Ile His Ser
210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Lys Thr Leu
                245                 250                 255

Ser Asn Leu Lys Glu Leu Gly Phe His Ser Asn Asn Ile Arg Ser Ile
                260                 265                 270

Pro Glu Arg Ala Phe Val Gly Asn Pro Ser Leu Ile Thr Ile His Phe
                275                 280                 285

Tyr Asp Asn Pro Ile Gln Phe Val Gly Ile Ser Ala Phe Gln His Leu
290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Thr Leu Glu Ser Leu Thr Leu Thr
                325                 330                 335

Gly Ala Lys Ile Ser Ser Leu Pro Gln Thr Val Cys Asp Gln Leu Pro
                340                 345                 350

Asn Leu Gln Val Leu Asp Leu Ser Tyr Asn Leu Leu Glu Asp Leu Pro
                355                 360                 365

Ser Leu Ser Gly Cys Gln Lys Leu Gln Lys Ile Asp Leu Arg His Asn
                370                 375                 380

Glu Ile Tyr Glu Ile Lys Gly Gly Thr Phe Gln Gln Leu Phe Asn Leu
385                 390                 395                 400

Arg Ser Leu Asn Leu Ala Arg Asn Lys Ile Ala Ile Ile His Pro Asn
                405                 410                 415

Ala Phe Ser Thr Leu Pro Ser Leu Ile Lys Leu Asp Leu Ser Ser Asn
                420                 425                 430

Leu Leu Ser Ser Phe Pro Val Thr Gly Leu His Gly Leu Thr His Leu
                435                 440                 445

Lys Leu Thr Gly Asn Arg Ala Leu Gln Ser Leu Ile Pro Ser Ala Asn
                450                 455                 460
```

```
Phe Pro Glu Leu Lys Ile Ile Glu Met Pro Tyr Ala Tyr Gln Cys Cys
465                 470                 475                 480

Ala Phe Gly Gly Cys Glu Asn Val Tyr Lys Ile Pro Asn Gln Trp Asn
            485                 490                 495

Lys Asp Asp Ser Ser Val Asp Asp Leu Arg Lys Lys Asp Ala Gly
        500                 505                 510

Leu Phe Gln Val Gln Asp Glu Arg Asp Leu Glu Asp Phe Leu Leu Asp
            515                 520                 525

Phe Glu Glu Asp Leu Lys Val Leu His Ser Val Gln Cys Ser Pro Pro
530                 535                 540

Pro Gly Pro Phe Lys Pro Cys Glu His Leu Phe Gly Ser Trp Leu Ile
545                 550                 555                 560

Arg Ile Gly Val Trp Thr Thr Ala Val Leu Ala Leu Ser Cys Asn Ala
                565                 570                 575

Leu Val Ala Phe Thr Val Phe Arg Thr Pro Leu Tyr Ile Ser Ser Ile
            580                 585                 590

Lys Leu Leu Ile Gly Val Ile Ala Val Val Asp Ile Leu Met Gly Val
            595                 600                 605

Ser Ser Ala Ile Leu Ala Val Val Asp Thr Phe Thr Phe Gly Ser Phe
610                 615                 620

Ala Gln His Gly Ala Trp Trp Glu Gly Gly Ile Gly Cys Gln Ile Val
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Cys Ser Ser Lys Phe
            660                 665                 670

Glu Met Lys Ala Pro Leu Ser Ser Leu Lys Ala Ile Ile Leu Leu Cys
            675                 680                 685

Val Leu Leu Ala Leu Thr Ile Ala Thr Val Pro Leu Leu Gly Gly Ser
690                 695                 700

Glu Tyr Asn Ala Ser Pro Leu Cys Leu Pro Leu Pro Phe Gly Glu Pro
705                 710                 715                 720

Ser Thr Thr Gly Tyr Met Val Ala Leu Val Leu Leu Asn Ser Leu Cys
                725                 730                 735

Phe Leu Ile Met Thr Ile Ala Tyr Thr Arg Leu Tyr Cys Ser Leu Glu
            740                 745                 750

Lys Gly Glu Leu Glu Asn Leu Trp Asp Cys Ser Met Val Lys His Thr
            755                 760                 765

Ala Leu Leu Leu Phe Thr Asn Cys Ile Leu Tyr Cys Pro Val Ala Phe
770                 775                 780

Leu Ser Phe Ser Ser Leu Leu Asn Leu Thr Phe Ile Ser Pro Glu Val
785                 790                 795                 800

Ile Lys Phe Ile Leu Leu Val Ile Val Pro Leu Pro Ala Cys Leu Asn
                805                 810                 815

Pro Leu Leu Tyr Ile Val Phe Asn Pro His Phe Lys Glu Asp Met Gly
            820                 825                 830

Ser Leu Gly Lys Gln Thr Arg Phe Trp Thr Arg Ala Lys His Pro Ser
            835                 840                 845

Leu Leu Ser Ile Asn Ser Asp Asp Val Glu Lys Arg Ser Cys Asp Ser
850                 855                 860

Thr Gln Ala Leu Val Ser Phe Thr His Ala Ser Ile Ala Tyr Asp Leu
865                 870                 875                 880
```

Pro Ser Asp Ser Gly Ser Ser Pro Ala Tyr Pro Met Thr Glu Ser Cys
                885                 890                 895
His Leu Ser Ser Val Ala Phe Val Pro Cys Leu
            900                 905

<210> SEQ ID NO 25
<211> LENGTH: 886
<212> TYPE: PRT
<213> ORGANISM: Rattus rattus

<400> SEQUENCE: 25

Gly Ser Pro Pro Arg Pro Asp Thr Met Pro Arg Gly Cys Pro Ser Tyr
1               5                   10                  15

Cys His Cys Glu Leu Asp Gly Arg Met Leu Leu Arg Val Asp Cys Ser
                20                  25                  30

Asp Leu Gly Leu Ser Glu Leu Pro Ser Asn Leu Ser Val Phe Thr Ser
            35                  40                  45

Tyr Leu Asp Leu Ser Met Asn Asn Ile Ser Gln Leu Pro Ala Ser Leu
    50                  55                  60

Leu His Arg Leu Arg Phe Leu Glu Glu Leu Arg Leu Ala Gly Asn Ala
65                  70                  75                  80

Leu Thr His Ile Pro Lys Gly Ala Phe Ala Gly Leu His Ser Leu Lys
                85                  90                  95

Val Leu Met Leu Gln Asn Asn Gln Leu Arg Gln Val Pro Glu Glu Ala
                100                 105                 110

Leu Gln Asn Leu Arg Ser Leu Gln Ser Leu Arg Leu Asp Ala Asn His
            115                 120                 125

Ile Ser Tyr Val Pro Pro Ser Cys Phe Ser Gly Leu His Ser Leu Arg
    130                 135                 140

His Leu Trp Leu Asp Asp Asn Ala Leu Thr Asp Val Pro Val Gln Ala
145                 150                 155                 160

Phe Arg Ser Leu Ser Ala Leu Gln Ala Met Thr Leu Ala Leu Asn Lys
                165                 170                 175

Ile His His Ile Ala Asp His Ala Phe Gly Asn Leu Ser Ser Leu Val
                180                 185                 190

Val Leu His Leu His Asn Asn Arg Ile His Ser Leu Gly Lys Lys Cys
            195                 200                 205

Phe Asp Gly Leu His Ser Leu Glu Thr Leu Asp Leu Asn Tyr Asn Asn
    210                 215                 220

Leu Asp Glu Phe Pro Thr Ala Ile Lys Thr Leu Ser Asn Leu Lys Glu
225                 230                 235                 240

Leu Gly Phe His Ser Asn Asn Ile Arg Ser Ile Pro Glu Arg Ala Phe
                245                 250                 255

Val Gly Asn Pro Ser Leu Ile Thr Ile His Phe Tyr Asp Asn Pro Ile
                260                 265                 270

Gln Phe Val Gly Ile Ser Ala Phe His Leu Pro Glu Leu Arg Thr
            275                 280                 285

Leu Thr Leu Asn Gly Ala Ser Gln Ile Thr Glu Phe Pro Asp Leu Thr
    290                 295                 300

Gly Thr Ala Thr Leu Glu Ser Leu Thr Leu Thr Gly Ala Lys Ile Ser
305                 310                 315                 320

Ser Leu Pro Gln Thr Val Cys Asp Gln Leu Pro Asn Leu Gln Val Leu
                325                 330                 335

Asp Leu Ser Tyr Asn Leu Leu Glu Asp Leu Pro Ser Leu Ser Gly Cys
                340                 345                 350

```
Gln Lys Leu Gln Lys Ile Asp Leu Arg His Asn Glu Ile Tyr Glu Ile
        355                 360                 365
Lys Gly Gly Thr Phe Gln Gln Leu Phe Asn Leu Arg Ser Leu Asn Leu
    370                 375                 380
Ala Arg Asn Lys Ile Ala Ile Ile His Pro Asn Ala Phe Ser Thr Leu
385                 390                 395                 400
Pro Ser Leu Ile Lys Leu Asp Leu Ser Ser Asn Leu Leu Ser Ser Phe
                405                 410                 415
Pro Val Thr Gly Leu His Gly Leu Thr His Leu Lys Leu Thr Gly Asn
                420                 425                 430
Arg Ala Leu Gln Ser Leu Ile Pro Ser Ala Asn Phe Pro Glu Leu Lys
                435                 440                 445
Ile Ile Glu Met Pro Tyr Ala Tyr Gln Cys Cys Ala Phe Gly Gly Cys
            450                 455                 460
Glu Asn Val Tyr Lys Ile Pro Asn Gln Trp Asn Lys Asp Asp Ser Ser
465                 470                 475                 480
Ser Val Asp Asp Leu Arg Lys Lys Asp Ala Gly Leu Phe Gln Val Gln
                485                 490                 495
Asp Glu Arg Asp Leu Glu Asp Phe Leu Leu Asp Phe Glu Glu Asp Leu
                500                 505                 510
Lys Val Leu His Ser Val Gln Cys Ser Pro Pro Gly Pro Phe Lys
                515                 520                 525
Pro Cys Glu His Leu Phe Gly Ser Trp Leu Ile Arg Ile Gly Val Trp
            530                 535                 540
Thr Thr Ala Val Leu Ala Leu Ser Cys Asn Ala Leu Val Ala Phe Thr
545                 550                 555                 560
Val Phe Arg Thr Pro Leu Tyr Ile Ser Ser Ile Lys Leu Leu Ile Gly
                565                 570                 575
Val Ile Ala Val Val Asp Ile Leu Met Gly Val Ser Ser Ala Ile Leu
                580                 585                 590
Ala Val Val Asp Thr Phe Thr Phe Gly Ser Phe Ala Gln His Gly Ala
            595                 600                 605
Trp Trp Glu Gly Gly Ile Gly Cys Gln Ile Val Gly Phe Leu Ser Ile
        610                 615                 620
Phe Ala Ser Glu Ser Ser Val Phe Leu Leu Thr Leu Ala Ala Leu Glu
625                 630                 635                 640
Arg Gly Phe Ser Val Lys Cys Ser Ser Lys Phe Glu Met Lys Ala Pro
                645                 650                 655
Leu Ser Ser Leu Lys Ala Ile Ile Leu Leu Cys Val Leu Leu Ala Leu
                660                 665                 670
Thr Ile Ala Thr Val Pro Leu Leu Gly Gly Ser Glu Tyr Asn Ala Ser
                675                 680                 685
Pro Leu Cys Leu Pro Leu Pro Phe Gly Glu Pro Ser Thr Thr Gly Tyr
            690                 695                 700
Met Val Ala Leu Val Leu Leu Asn Ser Leu Cys Phe Leu Ile Met Thr
705                 710                 715                 720
Ile Ala Tyr Thr Arg Leu Tyr Cys Ser Leu Glu Lys Gly Glu Leu Glu
                725                 730                 735
Asn Leu Trp Asp Cys Ser Met Val Lys His Thr Ala Leu Leu Leu Phe
            740                 745                 750
Thr Asn Cys Ile Leu Tyr Cys Pro Val Ala Phe Leu Ser Phe Ser Ser
            755                 760                 765
```

```
Leu Leu Asn Leu Thr Phe Ile Ser Pro Glu Val Ile Lys Phe Ile Leu
        770                 775                 780

Leu Val Ile Val Pro Leu Pro Ala Cys Leu Asn Pro Leu Leu Tyr Ile
785                 790                 795                 800

Val Phe Asn Pro His Phe Lys Glu Asp Met Gly Ser Leu Gly Lys Gln
                805                 810                 815

Thr Arg Phe Trp Thr Arg Ala Lys His Pro Ser Leu Leu Ser Ile Asn
                820                 825                 830

Ser Asp Asp Val Glu Lys Arg Ser Cys Asp Ser Thr Gln Ala Leu Val
            835                 840                 845

Ser Phe Thr His Ala Ser Ile Ala Tyr Asp Leu Pro Ser Asp Ser Gly
        850                 855                 860

Ser Ser Pro Ala Tyr Pro Met Thr Glu Ser Cys His Leu Ser Ser Val
865                 870                 875                 880

Ala Phe Val Pro Cys Leu
                885

<210> SEQ ID NO 26
<211> LENGTH: 907
<212> TYPE: PRT
<213> ORGANISM: Mus musculus

<400> SEQUENCE: 26

Met Asp Thr Ser Cys Val His Met Leu Leu Ser Leu Leu Ala Leu Leu
1               5                   10                  15

Gln Leu Val Ala Ala Gly Ser Ser Pro Gly Pro Asp Ala Ile Pro Arg
            20                  25                  30

Gly Cys Pro Ser His Cys His Cys Glu Leu Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Pro Ala Ser Leu Leu His Arg Leu Cys Phe Leu Glu Glu Leu Arg
                85                  90                  95

Leu Ala Gly Asn Ala Leu Thr His Ile Pro Lys Gly Ala Phe Thr Gly
            100                 105                 110

Leu His Ser Leu Lys Val Leu Met Leu Gln Asn Asn Gln Leu Arg Gln
        115                 120                 125

Val Pro Glu Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Asp
                165                 170                 175

Val Pro Val Gln Ala Phe Arg Ser Leu Ser Ala Leu Gln Ala Met Thr
            180                 185                 190

Leu Ala Leu Asn Lys Ile His His Ile Ala Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Lys Thr Leu
                245                 250                 255
```

```
Ser Asn Leu Lys Glu Leu Gly Phe His Ser Asn Ile Arg Ser Ile
            260                 265                 270

Pro Glu Arg Ala Phe Val Gly Asn Pro Ser Leu Ile Thr Ile His Phe
            275                 280                 285

Tyr Asp Asn Pro Ile Gln Phe Val Gly Val Ser Ala Phe Gln His Leu
            290                 295                 300

Pro Glu Leu Arg Thr Leu Thr Leu Asn Gly Ala Ser His Ile Thr Glu
305                 310                 315                 320

Phe Pro His Leu Thr Gly Thr Ala Thr Leu Glu Ser Leu Thr Leu Thr
                    325                 330                 335

Gly Ala Lys Ile Ser Ser Leu Pro Gln Ala Val Cys Asp Gln Leu Pro
            340                 345                 350

Asn Leu Gln Val Leu Asp Leu Ser Tyr Asn Leu Leu Glu Asp Leu Pro
            355                 360                 365

Ser Leu Ser Gly Cys Gln Lys Leu Gln Lys Ile Asp Leu Arg His Asn
            370                 375                 380

Glu Ile Tyr Glu Ile Lys Gly Ser Thr Phe Gln Gln Leu Phe Asn Leu
385                 390                 395                 400

Arg Ser Leu Asn Leu Ala Trp Asn Lys Ile Ala Ile His Pro Asn
            405                 410                 415

Ala Phe Ser Thr Leu Pro Ser Leu Ile Lys Leu Asp Leu Ser Ser Asn
                    420                 425                 430

Leu Leu Ser Ser Phe Pro Val Thr Gly Leu His Gly Leu Thr His Leu
            435                 440                 445

Lys Leu Thr Gly Asn Arg Ala Leu Gln Ser Leu Ile Pro Ser Ala Asn
            450                 455                 460

Phe Pro Glu Leu Lys Ile Ile Glu Met Pro Ser Ala Tyr Gln Cys Cys
465                 470                 475                 480

Ala Phe Gly Gly Cys Glu Asn Val Tyr Lys Ile Ser Asn Gln Trp Asn
                    485                 490                 495

Lys Asp Asp Gly Asn Ser Val Asp Asp Leu His Lys Lys Asp Ala Gly
            500                 505                 510

Leu Phe Gln Val Gln Asp Glu Arg Asp Leu Glu Asp Phe Leu Leu Asp
            515                 520                 525

Phe Glu Glu Asp Leu Lys Ala Leu His Ser Val Gln Cys Ser Pro Ser
530                 535                 540

Pro Gly Pro Phe Lys Pro Cys Glu His Leu Phe Gly Ser Trp Leu Ile
545                 550                 555                 560

Arg Ile Gly Val Trp Thr Thr Ala Val Leu Ala Leu Ser Cys Asn Ala
                    565                 570                 575

Leu Val Ala Leu Thr Val Phe Arg Thr Pro Leu Tyr Ile Ser Ser Ile
            580                 585                 590

Lys Leu Leu Ile Gly Val Ile Ala Val Asp Ile Leu Met Gly Val
            595                 600                 605

Ser Ser Ala Val Leu Ala Ala Val Asp Ala Phe Thr Phe Gly Arg Phe
            610                 615                 620

Ala Gln His Gly Ala Trp Trp Glu Asp Gly Ile Gly Cys Gln Ile Val
625                 630                 635                 640

Gly Phe Leu Ser Ile Phe Ala Ser Glu Ser Ser Ile Phe Leu Leu Thr
                    645                 650                 655

Leu Ala Ala Leu Glu Arg Gly Phe Ser Val Lys Cys Ser Ser Lys Phe
            660                 665                 670
```

```
Glu Val Lys Ala Pro Leu Phe Ser Leu Arg Ala Ile Val Leu Leu Cys
            675                 680                 685

Val Leu Leu Ala Leu Thr Ile Ala Thr Ile Pro Leu Leu Gly Gly Ser
690                 695                 700

Lys Tyr Asn Ala Ser Pro Leu Cys Leu Pro Leu Pro Phe Gly Glu Pro
705                 710                 715                 720

Ser Thr Thr Gly Tyr Met Val Ala Leu Val Leu Leu Asn Ser Leu Cys
            725                 730                 735

Phe Leu Ile Met Thr Ile Ala Tyr Thr Lys Leu Tyr Cys Ser Leu Glu
            740                 745                 750

Lys Gly Glu Leu Glu Asn Leu Trp Asp Cys Ser Met Val Lys His Ile
            755                 760                 765

Ala Leu Leu Leu Phe Ala Asn Cys Ile Leu Tyr Cys Pro Val Ala Phe
            770                 775                 780

Leu Ser Phe Ser Ser Leu Leu Asn Leu Thr Phe Ile Ser Pro Asp Val
785                 790                 795                 800

Ile Lys Phe Ile Leu Leu Val Ile Val Pro Leu Pro Ser Cys Leu Asn
            805                 810                 815

Pro Leu Leu Tyr Ile Val Phe Asn Pro His Phe Lys Glu Asp Met Gly
            820                 825                 830

Ser Leu Gly Lys His Thr Arg Phe Trp Met Arg Ser Lys His Ala Ser
            835                 840                 845

Leu Leu Ser Ile Asn Ser Asp Asp Val Glu Lys Arg Ser Cys Glu Ser
            850                 855                 860

Thr Gln Ala Leu Val Ser Phe Thr His Ala Ser Ile Ala Tyr Asp Leu
865                 870                 875                 880

Pro Ser Thr Ser Gly Ala Ser Pro Ala Tyr Pro Met Thr Glu Ser Cys
            885                 890                 895

His Leu Ser Ser Val Ala Phe Val Pro Cys Leu
            900                 905

<210> SEQ ID NO 27
<211> LENGTH: 886
<212> TYPE: PRT
<213> ORGANISM: Mus musculus

<400> SEQUENCE: 27

Gly Ser Ser Pro Gly Pro Asp Ala Ile Pro Arg Gly Cys Pro Ser His
1               5                   10                  15

Cys His Cys Glu Leu Asp Gly Arg Met Leu Leu Arg Val Asp Cys Ser
                20                  25                  30

Asp Leu Gly Leu Ser Glu Leu Pro Ser Asn Leu Ser Val Phe Thr Ser
            35                  40                  45

Tyr Leu Asp Leu Ser Met Asn Asn Ile Ser Gln Leu Pro Ala Ser Leu
50                  55                  60

Leu His Arg Leu Cys Phe Leu Glu Glu Leu Arg Leu Ala Gly Asn Ala
65                  70                  75                  80

Leu Thr His Ile Pro Lys Gly Ala Phe Thr Gly Leu His Ser Leu Lys
                85                  90                  95

Val Leu Met Leu Gln Asn Asn Gln Leu Arg Gln Val Pro Glu Glu Ala
                100                 105                 110

Leu Gln Asn Leu Arg Ser Leu Gln Ser Leu Arg Leu Asp Ala Asn His
            115                 120                 125

Ile Ser Tyr Val Pro Pro Ser Cys Phe Ser Gly Leu His Ser Leu Arg
130                 135                 140
```

```
His Leu Trp Leu Asp Asp Asn Ala Leu Thr Asp Val Pro Val Gln Ala
145                 150                 155                 160

Phe Arg Ser Leu Ser Ala Leu Gln Ala Met Thr Leu Ala Leu Asn Lys
            165                 170                 175

Ile His His Ile Ala Asp Tyr Ala Phe Gly Asn Leu Ser Ser Leu Val
        180                 185                 190

Val Leu His Leu His Asn Asn Arg Ile His Ser Leu Gly Lys Lys Cys
    195                 200                 205

Phe Asp Gly Leu His Ser Leu Glu Thr Leu Asp Leu Asn Tyr Asn Asn
210                 215                 220

Leu Asp Glu Phe Pro Thr Ala Ile Lys Thr Leu Ser Asn Leu Lys Glu
225                 230                 235                 240

Leu Gly Phe His Ser Asn Asn Ile Arg Ser Ile Pro Glu Arg Ala Phe
            245                 250                 255

Val Gly Asn Pro Ser Leu Ile Thr Ile His Phe Tyr Asp Asn Pro Ile
        260                 265                 270

Gln Phe Val Gly Val Ser Ala Phe Gln His Leu Pro Glu Leu Arg Thr
    275                 280                 285

Leu Thr Leu Asn Gly Ala Ser His Ile Thr Glu Phe Pro His Leu Thr
290                 295                 300

Gly Thr Ala Thr Leu Glu Ser Leu Thr Leu Thr Gly Ala Lys Ile Ser
305                 310                 315                 320

Ser Leu Pro Gln Ala Val Cys Asp Gln Leu Pro Asn Leu Gln Val Leu
            325                 330                 335

Asp Leu Ser Tyr Asn Leu Leu Glu Asp Leu Pro Ser Leu Ser Gly Cys
        340                 345                 350

Gln Lys Leu Gln Lys Ile Asp Leu Arg His Asn Glu Ile Tyr Glu Ile
    355                 360                 365

Lys Gly Ser Thr Phe Gln Gln Leu Phe Asn Leu Arg Ser Leu Asn Leu
370                 375                 380

Ala Trp Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
            405                 410                 415

Pro Val Thr Gly Leu His Gly Leu Thr His Leu Lys Leu Thr Gly Asn
        420                 425                 430

Arg Ala Leu Gln Ser Leu Ile Pro Ser Ala Asn Phe Pro Glu Leu Lys
    435                 440                 445

Ile Ile Glu Met Pro Ser Ala Tyr Gln Cys Cys Ala Phe Gly Gly Cys
450                 455                 460

Glu Asn Val Tyr Lys Ile Ser Asn Gln Trp Asn Lys Asp Asp Gly Asn
465                 470                 475                 480

Ser Val Asp Asp Leu His Lys Lys Asp Ala Gly Leu Phe Gln Val Gln
            485                 490                 495

Asp Glu Arg Asp Leu Glu Asp Phe Leu Leu Asp Phe Glu Glu Asp Leu
        500                 505                 510

Lys Ala Leu His Ser Val Gln Cys Ser Pro Ser Pro Gly Pro Phe Lys
    515                 520                 525

Pro Cys Glu His Leu Phe Gly Ser Trp Leu Ile Arg Ile Gly Val Trp
530                 535                 540

Thr Thr Ala Val Leu Ala Leu Ser Cys Asn Ala Leu Val Ala Leu Thr
545                 550                 555                 560
```

```
Val Phe Arg Thr Pro Leu Tyr Ile Ser Ser Ile Lys Leu Leu Ile Gly
                565                 570                 575

Val Ile Ala Val Val Asp Ile Leu Met Gly Val Ser Ser Ala Val Leu
        580                 585                 590

Ala Ala Val Asp Ala Phe Thr Phe Gly Arg Phe Ala Gln His Gly Ala
        595                 600                 605

Trp Trp Glu Asp Gly Ile Gly Cys Gln Ile Val Gly Phe Leu Ser Ile
        610                 615                 620

Phe Ala Ser Glu Ser Ser Ile Phe Leu Leu Thr Leu Ala Ala Leu Glu
625                 630                 635                 640

Arg Gly Phe Ser Val Lys Cys Ser Ser Lys Phe Glu Val Lys Ala Pro
                645                 650                 655

Leu Phe Ser Leu Arg Ala Ile Val Leu Leu Cys Val Leu Leu Ala Leu
                660                 665                 670

Thr Ile Ala Thr Ile Pro Leu Leu Gly Gly Ser Lys Tyr Asn Ala Ser
                675                 680                 685

Pro Leu Cys Leu Pro Leu Pro Phe Gly Glu Pro Ser Thr Thr Gly Tyr
                690                 695                 700

Met Val Ala Leu Val Leu Leu Asn Ser Leu Cys Phe Leu Ile Met Thr
705                 710                 715                 720

Ile Ala Tyr Thr Lys Leu Tyr Cys Ser Leu Glu Lys Gly Glu Leu Glu
                725                 730                 735

Asn Leu Trp Asp Cys Ser Met Val Lys His Ile Ala Leu Leu Leu Phe
                740                 745                 750

Ala Asn Cys Ile Leu Tyr Cys Pro Val Ala Phe Leu Ser Phe Ser Ser
                755                 760                 765

Leu Leu Asn Leu Thr Phe Ile Ser Pro Asp Val Ile Lys Phe Ile Leu
770                 775                 780

Leu Val Ile Val Pro Leu Pro Ser Cys Leu Asn Pro Leu Leu Tyr Ile
785                 790                 795                 800

Val Phe Asn Pro His Phe Lys Glu Asp Met Gly Ser Leu Gly Lys His
                805                 810                 815

Thr Arg Phe Trp Met Arg Ser Lys His Ala Ser Leu Leu Ser Ile Asn
                820                 825                 830

Ser Asp Asp Val Glu Lys Arg Ser Cys Glu Ser Thr Gln Ala Leu Val
                835                 840                 845

Ser Phe Thr His Ala Ser Ile Ala Tyr Asp Leu Pro Ser Thr Ser Gly
                850                 855                 860

Ala Ser Pro Ala Tyr Pro Met Thr Glu Ser Cys His Leu Ser Ser Val
865                 870                 875                 880

Ala Phe Val Pro Cys Leu
                885

<210> SEQ ID NO 28
<211> LENGTH: 112
<212> TYPE: PRT
<213> ORGANISM: Mus musculus

<400> SEQUENCE: 28

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
                20                  25                  30

Gly Asn Ser Phe Met His Trp Tyr Gln Gln Lys Pro Gly Gln Pro Pro
            35                  40                  45
```

Lys Leu Leu Ile Tyr Leu Ala Ser Asn Leu Glu Ser Gly Val Pro Ala
             50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Tyr
                 85                  90                  95

Glu Asp Pro Phe Thr Phe Gly Ser Gly Thr Lys Val Glu Ile Lys Arg
            100                 105                 110

<210> SEQ ID NO 29
<211> LENGTH: 118
<212> TYPE: PRT
<213> ORGANISM: Mus musculus

<400> SEQUENCE: 29

Gln Val Gln Leu Gln Gln Ser Gly Thr Glu Leu Met Lys Pro Gly Ala
 1               5                  10                  15

Ser Val Lys Ile Ser Cys Lys Ala Thr Gly Tyr Thr Phe Ser Ala Tyr
                 20                  25                  30

Trp Ile Glu Trp Ile Lys Gln Arg Pro Gly His Gly Leu Glu Trp Ile
             35                  40                  45

Gly Glu Ile Leu Pro Gly Ser Asp Ser Thr Asp Tyr Asn Glu Lys Phe
         50                  55                  60

Lys Val Lys Ala Thr Phe Ser Ser Asp Thr Ser Ser Asn Thr Val Tyr
 65                  70                  75                  80

Ile Gln Leu Asn Ser Leu Thr Tyr Glu Asp Ser Ala Val Tyr Tyr Cys
                 85                  90                  95

Ala Arg Gly Gly His Tyr Gly Ser Leu Asp Tyr Trp Gly Gln Gly Thr
            100                 105                 110

Thr Leu Lys Val Ser Ser
            115

<210> SEQ ID NO 30
<211> LENGTH: 112
<212> TYPE: PRT
<213> ORGANISM: Artificial Sequence
<220> FEATURE:
<223> OTHER INFORMATION: hu8E11.v1 light chain variable region

<400> SEQUENCE: 30

Asp Ile Val Met Thr Gln Ser Pro Asp Ser Leu Ala Val Ser Leu Gly
 1               5                  10                  15

Glu Arg Ala Thr Ile Asn Cys Arg Ala Ser Glu Ser Val Asp Asn Tyr
                 20                  25                  30

Gly Asn Ser Phe Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Asp
         50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Tyr
                 85                  90                  95

Glu Asp Pro Phe Thr Phe Gly Gln Gly Thr Lys Val Glu Ile Lys Arg
            100                 105                 110

<210> SEQ ID NO 31
<211> LENGTH: 118

<212> TYPE: PRT
<213> ORGANISM: Artificial Sequences
<220> FEATURE:
<223> OTHER INFORMATION: hu8E11.v1 heavy chain variable region

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
                20                  25                  30

Trp Ile Glu Trp Val Arg Gln Ala Pro Gly Gln Gly Leu Glu Trp Ile
            35                  40                  45

Gly Glu Ile Leu Pro Gly Ser Asp Ser Thr Asp Tyr Asn Glu Lys Phe
    50                  55                  60

Lys Val Arg Val Thr Ile Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
            115

<210> SEQ ID NO 32
<211> LENGTH: 112
<212> TYPE: PRT
<213> ORGANISM: Artificial Sequence
<220> FEATURE:
<223> OTHER INFORMATION: hu8E11.v2 light chain variable region

<400> SEQUENCE: 32

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

<210> SEQ ID NO 33
<211> LENGTH: 118
<212> TYPE: PRT
<213> ORGANISM: Artificial Sequence
<220> FEATURE:
<223> OTHER INFORMATION: hu8E11.v2 heavy chain variable region

<400> SEQUENCE: 33

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
                20                  25                  30

Trp Ile Glu Trp Val Arg Gln Ala Pro Gly Gln Gly Leu Glu Trp Ile

```
            35                  40                  45
Gly Glu Ile Leu Pro Gly Ser Asp Ser Thr Asp Tyr Asn Glu Lys Phe
        50                  55                  60

Lys Val Arg Ala Thr Phe Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
            115

<210> SEQ ID NO 34
<211> LENGTH: 112
<212> TYPE: PRT
<213> ORGANISM: Artificial Sequence
<220> FEATURE:
<223> OTHER INFORMATION: hu8E11.v3 light chain variable region

<400> SEQUENCE: 34

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

<210> SEQ ID NO 35
<211> LENGTH: 118
<212> TYPE: PRT
<213> ORGANISM: Artificial Sequence
<220> FEATURE:
<223> OTHER INFORMATION: hu8E11.v3 heavy chain variable region

<400> SEQUENCE: 35

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Val Thr Ile Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110
```

```
Leu Val Thr Val Ser Ser
        115

<210> SEQ ID NO 36
<211> LENGTH: 112
<212> TYPE: PRT
<213> ORGANISM: Artificial Sequence
<220> FEATURE:
<223> OTHER INFORMATION: hu8E11.v4 light chain variable region

<400> SEQUENCE: 36

Asp Ile Val Met Thr Gln Ser Pro Asp Ser Leu Ala Val Ser Leu Gly
1               5                   10                  15

Glu Arg Ala Thr Ile Asn Cys Arg Ala Ser Gln Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

<210> SEQ ID NO 37
<211> LENGTH: 118
<212> TYPE: PRT
<213> ORGANISM: Artificial Sequence
<220> FEATURE:
<223> OTHER INFORMATION: hu8E11.v4 heavy chain variable region

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Ala Thr Phe Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115

<210> SEQ ID NO 38
<211> LENGTH: 112
<212> TYPE: PRT
<213> ORGANISM: Artificial Sequence
<220> FEATURE:
<223> OTHER INFORMATION: hu8E11.v5 light chain variable region

<400> SEQUENCE: 38

Asp Ile Val Met Thr Gln Ser Pro Asp Ser Leu Ala Val Ser Leu Gly
```

```
                1               5                   10                  15
            Glu Arg Ala Thr Ile Asn Cys Arg Ala Ser Glu Ser Val Asp Asn Tyr
                            20                  25                  30

Gly Asn Ser Phe Met His Trp Tyr Gln Gln Lys Pro Gly Gln Pro Pro
                        35                  40                  45

Lys Leu Leu Ile Tyr Leu Ala Ser Asn Leu Glu Ser Gly Val Pro Asp
                    50                  55                  60

Arg Phe Ser Gly Ser Gly Ser Gly Thr Asp Phe Thr Leu Thr Ile Ser
            65                  70                  75                  80

Ser Leu Gln Ala Glu Asp Val Ala Val Tyr Tyr Cys Gln Gln Asn Tyr
                            85                  90                  95

Glu Asp Pro Phe Thr Phe Gly Gln Gly Thr Lys Val Glu Ile Lys Arg
                            100                 105                 110
```

<210> SEQ ID NO 39
<211> LENGTH: 118
<212> TYPE: PRT
<213> ORGANISM: Artificial Sequence
<220> FEATURE:
<223> OTHER INFORMATION: hu8E11.v5 heavy chain variable region

<400> SEQUENCE: 39

```
            Glu Val Gln Leu Val Gln Ser Gly Ala Glu Val Lys Lys Pro Gly Ala
            1               5                   10                  15

Ser Val Lys Val Ser Cys Lys Ala Ser Gly Tyr Thr Phe Ser Ala Tyr
                            20                  25                  30

Trp Ile Glu Trp Val Arg Gln Ala Pro Gly Gln Gly Leu Glu Trp Ile
                        35                  40                  45

Gly Glu Ile Leu Pro Gly Ser Asp Ser Thr Asp Tyr Asn Glu Lys Phe
                    50                  55                  60

Lys Val Arg Val Thr Ile Thr Arg Asp Thr Ser Thr Ser Thr Ala Tyr
            65                  70                  75                  80

Leu Glu Leu Ser Ser Leu Arg Ser Glu Asp Thr Ala Val Tyr Tyr Cys
                            85                  90                  95

Ala Arg Gly Gly His Tyr Gly Ser Leu Asp Tyr Trp Gly Gln Gly Thr
                            100                 105                 110

Leu Val Thr Val Ser Ser
                    115
```

<210> SEQ ID NO 40
<211> LENGTH: 112
<212> TYPE: PRT
<213> ORGANISM: Artificial Sequence
<220> FEATURE:
<223> OTHER INFORMATION: hu8E11.v6 light chain variable region

<400> SEQUENCE: 40

```
            Asp Ile Val Met Thr Gln Ser Pro Asp Ser Leu Ala Val Ser Leu Gly
            1               5                   10                  15

Glu Arg Ala Thr Ile Asn Cys Arg Ala Ser Glu Ser Val Asp Asn Tyr
                            20                  25                  30

Gly Asn Ser Phe Met His Trp Tyr Gln Gln Lys Pro Gly Gln Pro Pro
                        35                  40                  45

Lys Leu Leu Ile Tyr Leu Ala Ser Asn Leu Glu Ser Gly Val Pro Asp
                    50                  55                  60

Arg Phe Ser Gly Ser Gly Ser Gly Thr Asp Phe Thr Leu Thr Ile Ser
            65                  70                  75                  80
```

```
Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110
```

<210> SEQ ID NO 41
<211> LENGTH: 118
<212> TYPE: PRT
<213> ORGANISM: Artificial Sequence
<220> FEATURE:
<223> OTHER INFORMATION: hu8E11.v6 heavy chain variable region

<400> SEQUENCE: 41

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
                20                  25                  30

Trp Ile Glu Trp Val Arg Gln Ala Pro Gly Gln Gly Leu Glu Trp Ile
            35                  40                  45

Gly Glu Ile Leu Pro Gly Ser Asp Ser Thr Asp Tyr Asn Glu Lys Phe
        50                  55                  60

Lys Val Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115
```

<210> SEQ ID NO 42
<211> LENGTH: 112
<212> TYPE: PRT
<213> ORGANISM: Artificial Sequence
<220> FEATURE:
<223> OTHER INFORMATION: hu8E11.v7 light chain variable region

<400> SEQUENCE: 42

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
        50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110
```

<210> SEQ ID NO 43
<211> LENGTH: 118
<212> TYPE: PRT
<213> ORGANISM: Artificial Sequence
<220> FEATURE:
<223> OTHER INFORMATION: hu8E11.v7 heavy chain variable region -continued

```
<400> SEQUENCE: 43

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
50                  55                  60

Lys Val Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115

<210> SEQ ID NO 44
<211> LENGTH: 112
<212> TYPE: PRT
<213> ORGANISM: Artificial Sequence
<220> FEATURE:
<223> OTHER INFORMATION: hu8E11.v8 light chain variable region

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

<210> SEQ ID NO 45
<211> LENGTH: 118
<212> TYPE: PRT
<213> ORGANISM: Artificial Sequence
<220> FEATURE:
<223> OTHER INFORMATION: hu8E11.v9 heavy chain variable region

<400> SEQUENCE: 45

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
50                  55                  60
```

```
Lys Val Arg Val Thr Ile Thr Ala Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Ala Arg Gly Gly His Tyr Gly Ser Leu Asp Tyr Trp Gly Gln Gly Thr
            100                 105                 110

Leu Val Thr Val Ser Ser
            115

<210> SEQ ID NO 46
<211> LENGTH: 113
<212> TYPE: PRT
<213> ORGANISM: Mus musculus

<400> SEQUENCE: 46

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Ile Tyr Phe Cys Ser Gln Ser
                 85                  90                  95

Thr His Phe Pro Tyr Thr Phe Gly Gly Gly Thr Lys Leu Glu Ile Lys
            100                 105                 110

Arg

<210> SEQ ID NO 47
<211> LENGTH: 115
<212> TYPE: PRT
<213> ORGANISM: Mus musculus

<400> SEQUENCE: 47

Gln Val Gln Leu Gln Gln Pro Gly Ala Glu Met Val Lys Pro Gly Ala
 1               5                  10                  15

Ser Val Lys Leu Ser Cys Lys Ala Ser Val Asp Thr Phe Asn Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Ile Glu Lys Phe
 50                  55                  60

Lys Asn Arg Ala Thr Val Thr Val Asp Lys Ser Ser Ser Thr Ala Phe
 65                  70                  75                  80

Met Gln Leu Ser Ser Leu Thr Ser Glu Asp Ser Ala Val Tyr Tyr Cys
                 85                  90                  95

Ala Thr Gly Trp Tyr Phe Asp Val Trp Gly Ala Gly Thr Thr Val Thr
            100                 105                 110

Val Ser Ser
        115

<210> SEQ ID NO 48
<211> LENGTH: 114
<212> TYPE: PRT
```

<213> ORGANISM: Mus musculus

<400> SEQUENCE: 48

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Phe Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Asn Val Gln Ala Glu Asp Leu Ala Val Tyr Tyr Cys Gln Asn
                85                  90                  95

Asp Tyr Ser Phe Pro Phe Thr Phe Gly Gln Gly Thr Lys Val Glu Ile
            100                 105                 110

Lys Arg

<210> SEQ ID NO 49
<211> LENGTH: 121
<212> TYPE: PRT
<213> ORGANISM: Mus musculus

<400> SEQUENCE: 49

Glu Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Lys Asn Gly Leu Glu Trp Ile
        35                  40                  45

Gly Leu Ile Asn Cys Tyr Asn Gly Gly Thr Asn Tyr Asn Gln Lys Phe
50                  55                  60

Lys Gly Lys Ala Thr Leu Thr Val Asp Lys Ser Ser Ser Thr Ala Phe
65                  70                  75                  80

Met Glu Leu Leu Ser Leu Thr Ser Glu Asp Ser Ala Val Tyr Tyr Cys
                85                  90                  95

Ala Arg Gly Gly Ser Thr Met Ile Thr Pro Arg Phe Ala Tyr Trp Gly
            100                 105                 110

Gln Gly Thr Leu Val Thr Val Ser Ser
        115                 120

<210> SEQ ID NO 50
<211> LENGTH: 108
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Thr Thr Pro Pro
                 85                  90                  95

Thr Phe Gly Gln Gly Thr Lys Val Glu Ile Lys Arg
            100                 105

<210> SEQ ID NO 51
<211> LENGTH: 116
<212> TYPE: PRT
<213> ORGANISM: Homo sapiens

<400> SEQUENCE: 51

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Ser Tyr
                 20                  25                  30

Ser Ile Ser Trp Val Arg Gln Ala Pro Gly Lys Gly Leu Glu Trp Val
             35                  40                  45

Ala Glu Ile Tyr Pro Pro Gly Gly Tyr Thr Asp Tyr Ala Asp Ser Val
         50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Lys Ala Arg Leu Phe Phe Asp Tyr Trp Gly Gln Gly Thr Leu Val
            100                 105                 110

Thr Val Ser Ser
        115

<210> SEQ ID NO 52
<211> LENGTH: 15
<212> TYPE: PRT
<213> ORGANISM: Mus musculus

<400> SEQUENCE: 52

Arg Ala Ser Glu Ser Val Asp Asn Tyr Gly Asn Ser Phe Met His
  1               5                  10                  15

<210> SEQ ID NO 53
<211> LENGTH: 7
<212> TYPE: PRT
<213> ORGANISM: Mus musculus

<400> SEQUENCE: 53

Leu Ala Ser Asn Leu Glu Ser
  1               5

<210> SEQ ID NO 54
<211> LENGTH: 9
<212> TYPE: PRT
<213> ORGANISM: Mus musculus

<400> SEQUENCE: 54

Gln Gln Asn Tyr Glu Asp Pro Phe Thr
  1               5

<210> SEQ ID NO 55
<211> LENGTH: 10
<212> TYPE: PRT
<213> ORGANISM: Mus musculus
```

```
<400> SEQUENCE: 55

Gly Tyr Thr Phe Ser Ala Tyr Trp Ile Glu
1               5                   10

<210> SEQ ID NO 56
<211> LENGTH: 17
<212> TYPE: PRT
<213> ORGANISM: Mus musculus

<400> SEQUENCE: 56

Glu Ile Leu Pro Gly Ser Asp Ser Thr Asp Tyr Asn Glu Lys Phe Lys
1               5                   10                  15

Val

<210> SEQ ID NO 57
<211> LENGTH: 9
<212> TYPE: PRT
<213> ORGANISM: Mus musculus

<400> SEQUENCE: 57

Gly Gly His Tyr Gly Ser Leu Asp Tyr
1               5

<210> SEQ ID NO 58
<211> LENGTH: 23
<212> TYPE: PRT
<213> ORGANISM: Artificial Sequence
<220> FEATURE:
<223> OTHER INFORMATION: Hu8E11 light chain (LC) framework 1 (FR1)

<400> SEQUENCE: 58

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 59
<211> LENGTH: 15
<212> TYPE: PRT
<213> ORGANISM: Artificial Sequence
<220> FEATURE:
<223> OTHER INFORMATION: Hu8E11 LC FR2

<400> SEQUENCE: 59

Trp Tyr Gln Gln Lys Pro Gly Gln Pro Pro Lys Leu Leu Ile Tyr
1               5                   10                  15

<210> SEQ ID NO 60
<211> LENGTH: 32
<212> TYPE: PRT
<213> ORGANISM: Artificial Sequence
<220> FEATURE:
<223> OTHER INFORMATION: Hu8E11.v1 LC FR3; Hu8E11.v2 LC FR3; Hu8E11.v5
      LC FR3; Hu8E11.v6 LC FR3

<400> SEQUENCE: 60

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 61
<211> LENGTH: 32
```

```
<212> TYPE: PRT
<213> ORGANISM: Artificial Sequence
<220> FEATURE:
<223> OTHER INFORMATION: Hu8E11.v3 LC FR3; Hu8E11.v4 LC FR3; Hu8E11.v7
      LC FR3; Hu8E11.v8 LC FR3

<400> SEQUENCE: 61

Gly Val Pro Asp Arg Phe Ser Gly Ser Gly Ser Arg Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 62
<211> LENGTH: 11
<212> TYPE: PRT
<213> ORGANISM: Artificial Sequence
<220> FEATURE:
<223> OTHER INFORMATION: Hu8E11 LC FR4

<400> SEQUENCE: 62

Phe Gly Gln Gly Thr Lys Val Glu Ile Lys Arg
1               5                   10

<210> SEQ ID NO 63
<211> LENGTH: 25
<212> TYPE: PRT
<213> ORGANISM: Artificial Sequence
<220> FEATURE:
<223> OTHER INFORMATION: Hu8E11 heavy chain (HC) framework1 (FR1)

<400> SEQUENCE: 63

Glu Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 64
<211> LENGTH: 14
<212> TYPE: PRT
<213> ORGANISM: Artificial Sequence
<220> FEATURE:
<223> OTHER INFORMATION: Hu8E11 HC FR2

<400> SEQUENCE: 64

Trp Val Arg Gln Ala Pro Gly Gln Gly Leu Glu Trp Ile Gly
1               5                   10

<210> SEQ ID NO 65
<211> LENGTH: 32
<212> TYPE: PRT
<213> ORGANISM: Artificial Sequence
<220> FEATURE:
<223> OTHER INFORMATION: Hu8E11.v1 HC FR3; Hu8E11.v3 HC FR3

<400> SEQUENCE: 65

Arg Val Thr Ile Thr Ser Asp Thr Ser Thr Ser Thr Val Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Hu8E11.v2 HC FR3; Hu8E11.v4 HC FR3
```

<400> SEQUENCE: 66

Arg Ala Thr Phe Thr Ser Asp Thr Ser Thr Thr Val Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 67
<211> LENGTH: 32
<212> TYPE: PRT
<213> ORGANISM: Artificial Sequence
<220> FEATURE:
<223> OTHER INFORMATION: Hu8E11.v5 HC FR3; Hu8E11.v7 HC FR3

<400> SEQUENCE: 67

Arg Val Thr Ile Thr Arg Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 68
<211> LENGTH: 32
<212> TYPE: PRT
<213> ORGANISM: Artificial Sequence
<220> FEATURE:
<223> OTHER INFORMATION: Hu8E11.v6 HC FR3; Hu8E11.v8 HC FR3

<400> SEQUENCE: 68

Arg Val Thr Ile Thr Ala Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 69
<211> LENGTH: 11
<212> TYPE: PRT
<213> ORGANISM: Artificial Sequence
<220> FEATURE:
<223> OTHER INFORMATION: Hu8E11 HC FR4

<400> SEQUENCE: 69

Trp Gly Gln Gly Thr Leu Val Thr Val Ser Ser
1               5                   10

<210> SEQ ID NO 70
<211> LENGTH: 16
<212> TYPE: PRT
<213> ORGANISM: Mus musculus

<400> SEQUENCE: 70

Arg Ser Ser Gln Ser Leu Val His Ser Asn Gly Asn Thr Tyr Leu Gln
1               5                   10                  15

<210> SEQ ID NO 71
<211> LENGTH: 7
<212> TYPE: PRT
<213> ORGANISM: Mus musculus

<400> SEQUENCE: 71

Lys Val Ser Asn Arg Phe Ser
1               5

<210> SEQ ID NO 72
<211> LENGTH: 9

-continued

```
<212> TYPE: PRT
<213> ORGANISM: Mus musculus

<400> SEQUENCE: 72

Ser Gln Ser Thr His Phe Pro Tyr Thr
1               5

<210> SEQ ID NO 73
<211> LENGTH: 10
<212> TYPE: PRT
<213> ORGANISM: Mus musculus

<400> SEQUENCE: 73

Val Asp Thr Phe Asn Ser Tyr Trp Met His
1               5                   10

<210> SEQ ID NO 74
<211> LENGTH: 17
<212> TYPE: PRT
<213> ORGANISM: Mus musculus

<400> SEQUENCE: 74

Glu Ile Asn Pro Ser Asn Gly Arg Thr Asn Tyr Ile Glu Lys Phe Lys
1               5                   10                  15

Asn

<210> SEQ ID NO 75
<211> LENGTH: 6
<212> TYPE: PRT
<213> ORGANISM: Mus musculus

<400> SEQUENCE: 75

Gly Trp Tyr Phe Asp Val
1               5

<210> SEQ ID NO 76
<211> LENGTH: 17
<212> TYPE: PRT
<213> ORGANISM: Mus musculus

<400> SEQUENCE: 76

Lys Ser Ser Gln Ser Leu Leu Asn Ser Gly Asn Gln Lys Asn Tyr Leu
1               5                   10                  15

Thr

<210> SEQ ID NO 77
<211> LENGTH: 7
<212> TYPE: PRT
<213> ORGANISM: Mus musculus

<400> SEQUENCE: 77

Trp Ala Ser Thr Arg Glu Ser
1               5

<210> SEQ ID NO 78
<211> LENGTH: 9
<212> TYPE: PRT
<213> ORGANISM: Mus musculus

<400> SEQUENCE: 78

Gln Asn Asp Tyr Ser Phe Pro Phe Thr
1               5
```

```
<210> SEQ ID NO 79
<211> LENGTH: 10
<212> TYPE: PRT
<213> ORGANISM: Mus musculus

<400> SEQUENCE: 79

Gly Tyr Ser Phe Thr Gly Tyr Thr Met Asn
1               5                   10

<210> SEQ ID NO 80
<211> LENGTH: 17
<212> TYPE: PRT
<213> ORGANISM: Mus musculus

<400> SEQUENCE: 80

Leu Ile Asn Cys Tyr Asn Gly Gly Thr Asn Tyr Asn Gln Lys Phe Lys
1               5                   10                  15

Gly

<210> SEQ ID NO 81
<211> LENGTH: 12
<212> TYPE: PRT
<213> ORGANISM: Mus musculus

<400> SEQUENCE: 81

Gly Gly Ser Thr Met Ile Thr Pro Arg Phe Ala Tyr
1               5                   10

<210> SEQ ID NO 82
<211> LENGTH: 11
<212> TYPE: PRT
<213> ORGANISM: Homo sapiens

<400> SEQUENCE: 82

Arg Ala Ser Gln Asp Val Ser Thr Ala Val Ala
1               5                   10

<210> SEQ ID NO 83
<211> LENGTH: 7
<212> TYPE: PRT
<213> ORGANISM: Homo sapiens

<400> SEQUENCE: 83

Ser Ala Ser Phe Leu Tyr Ser
1               5

<210> SEQ ID NO 84
<211> LENGTH: 9
<212> TYPE: PRT
<213> ORGANISM: Homo sapiens

<400> SEQUENCE: 84

Gln Gln Ser Tyr Thr Thr Pro Pro Thr
1               5

<210> SEQ ID NO 85
<211> LENGTH: 10
<212> TYPE: PRT
<213> ORGANISM: Homo sapiens

<400> SEQUENCE: 85

Gly Phe Thr Phe Thr Ser Tyr Ser Ile Ser
1               5                   10
```

-continued

```
<210> SEQ ID NO 86
<211> LENGTH: 17
<212> TYPE: PRT
<213> ORGANISM: Homo sapiens

<400> SEQUENCE: 86

Glu Ile Tyr Pro Pro Gly Gly Tyr Thr Asp Tyr Ala Asp Ser Val Lys
1               5                   10                  15

Gly

<210> SEQ ID NO 87
<211> LENGTH: 7
<212> TYPE: PRT
<213> ORGANISM: Homo sapiens

<400> SEQUENCE: 87

Ala Arg Leu Phe Phe Asp Tyr
1               5

<210> SEQ ID NO 88
<211> LENGTH: 218
<212> TYPE: PRT
<213> ORGANISM: Artificial Sequence
<220> FEATURE:
<223> OTHER INFORMATION: hu8E11.v2 light chain

<400> SEQUENCE: 88

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 89
<211> LENGTH: 448
<212> TYPE: PRT
```

<213> ORGANISM: Artificial Sequence
<220> FEATURE:
<223> OTHER INFORMATION: hu8E11.v2 heavy chain

<400> SEQUENCE: 89

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Ala Thr Phe Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
        405                 410                 415

Leu His Asn His Tyr Thr Gln Lys Ser Leu Ser Leu Ser Pro Gly Lys
            420                 425                 430

435                 440                 445

<210> SEQ ID NO 90
<211> LENGTH: 214
<212> TYPE: PRT
<213> ORGANISM: Homo sapiens

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 91
<211> LENGTH: 446
<212> TYPE: PRT
<213> ORGANISM: Homo sapiens

<400> SEQUENCE: 91

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Ile Ser Trp Val Arg Gln Ala Pro Gly Lys Gly Leu Glu Trp Val
        35                  40                  45

Ala Glu Ile Tyr Pro Pro Gly Gly Tyr Thr Asp Tyr Ala Asp Ser Val

```
            50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                     85                  90                  95

Ala Lys Ala Arg Leu Phe Phe Asp Tyr Trp Gly Gln Gly Thr Leu Val
                    100                 105                 110

Thr Val Ser Ser Ala Ser Thr Lys Gly Pro Ser Val Phe Pro Leu Ala
                    115                 120                 125

Pro Ser Ser Lys Ser Thr Ser Gly Gly Thr Ala Ala Leu Gly Cys Leu
                    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                    165                 170                 175

Gly Leu Tyr Ser Leu Ser Ser Val Val Thr Val Pro Ser Ser Ser Leu
                    180                 185                 190

Gly Thr Gln Thr Tyr Ile Cys Asn Val Asn His Lys Pro Ser Asn Thr
                    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                    245                 250                 255

Glu Val Thr Cys Val Val Val Asp Val Ser His Glu Asp Pro Glu Val
                    260                 265                 270

Lys Phe Asn Trp Tyr Val Asp Gly Val Glu Val His Asn Ala Lys Thr
                    275                 280                 285

Lys Pro Arg Glu Glu Gln Tyr Asn Ser Thr Tyr Arg Val Val Ser Val
                    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                    325                 330                 335

Lys Ala Lys Gly Gln Pro Arg Glu Pro Gln Val Tyr Thr Leu Pro Pro
                    340                 345                 350

Ser Arg Glu Glu Met Thr Lys Asn Gln Val Ser Leu Thr Cys Leu Val
                    355                 360                 365

Lys Gly Phe Tyr Pro Ser Asp Ile Ala Val Glu Trp Glu Ser Asn Gly
                    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                    405                 410                 415

Gln Gln Gly Asn Val Phe Ser Cys Ser Val Met His Glu Ala Leu His
                    420                 425                 430

Asn His Tyr Thr Gln Lys Ser Leu Ser Leu Ser Pro Gly Lys
                    435                 440                 445

<210> SEQ ID NO 92
<211> LENGTH: 20
<212> TYPE: DNA
<213> ORGANISM: Artificial Sequence
```

```
<220> FEATURE:
<223> OTHER INFORMATION: Antisense forward primer

<400> SEQUENCE: 92
accaactgca tcctaaactg                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense reverse primer

<400> SEQUENCE: 93
accgagtttc acctcagctc                                              20

<210> SEQ ID NO 94
<211> LENGTH: 40
<212> TYPE: DNA
<213> ORGANISM: Artificial Sequence
<220> FEATURE:
<223> OTHER INFORMATION: Sense forward primer

<400> SEQUENCE: 94
acattgccct gttgctcttc acattgccct gttgctcttc                        40

<210> SEQ ID NO 95
<211> LENGTH: 21
<212> TYPE: DNA
<213> ORGANISM: Artificial Sequence
<220> FEATURE:
<223> OTHER INFORMATION: Sense reverse primer

<400> SEQUENCE: 95
actgctctga tatactcaat c                                            21

<210> SEQ ID NO 96
<211> LENGTH: 770
<212> TYPE: PRT
<213> ORGANISM: Artificial Sequence
<220> FEATURE:
<223> OTHER INFORMATION: LgR5 ECD huFc (1 to 537 are LgR5 ECD)

<400> SEQUENCE: 96
```

Gly Ser Ser Pro Arg Ser Gly Val Leu Leu Arg Gly Cys Pro Thr His
1               5                   10                  15

Cys His Cys Glu Pro Asp Gly Arg Met Leu Leu Arg Val Asp Cys Ser
            20                  25                  30

Asp Leu Gly Leu Ser Glu Leu Pro Ser Asn Leu Ser Val Phe Thr Ser
        35                  40                  45

Tyr Leu Asp Leu Ser Met Asn Asn Ile Ser Gln Leu Pro Asn Pro
    50                  55                  60

Leu Pro Ser Leu Arg Phe Leu Glu Glu Leu Arg Leu Ala Gly Asn Ala
65                  70                  75                  80

Leu Thr Tyr Ile Pro Lys Gly Ala Phe Thr Gly Leu Tyr Ser Leu Lys
                85                  90                  95

Val Leu Met Leu Gln Asn Asn Gln Leu Arg His Val Pro Thr Glu Ala
            100                 105                 110

Leu Gln Asn Leu Arg Ser Leu Gln Ser Leu Arg Leu Asp Ala Asn His
        115                 120                 125

Ile Ser Tyr Val Pro Pro Ser Cys Phe Ser Gly Leu His Ser Leu Arg
    130                 135                 140

```
His Leu Trp Leu Asp Asp Asn Ala Leu Thr Glu Ile Pro Val Gln Ala
145                 150                 155                 160

Phe Arg Ser Leu Ser Ala Leu Gln Ala Met Thr Leu Ala Leu Asn Lys
            165                 170                 175

Ile His His Ile Pro Asp Tyr Ala Phe Gly Asn Leu Ser Ser Leu Val
        180                 185                 190

Val Leu His Leu His Asn Asn Arg Ile His Ser Leu Gly Lys Lys Cys
            195                 200                 205

Phe Asp Gly Leu His Ser Leu Glu Thr Leu Asp Leu Asn Tyr Asn Asn
        210                 215                 220

Leu Asp Glu Phe Pro Thr Ala Ile Arg Thr Leu Ser Asn Leu Lys Glu
225                 230                 235                 240

Leu Gly Phe His Ser Asn Asn Ile Arg Ser Ile Pro Glu Lys Ala Phe
            245                 250                 255

Val Gly Asn Pro Ser Leu Ile Thr Ile His Phe Tyr Asp Asn Pro Ile
            260                 265                 270

Gln Phe Val Gly Arg Ser Ala Phe Gln His Leu Pro Glu Leu Arg Thr
        275                 280                 285

Leu Thr Leu Asn Gly Ala Ser Gln Ile Thr Glu Phe Pro Asp Leu Thr
        290                 295                 300

Gly Thr Ala Asn Leu Glu Ser Leu Thr Leu Thr Gly Ala Gln Ile Ser
305                 310                 315                 320

Ser Leu Pro Gln Thr Val Cys Asn Gln Leu Pro Asn Leu Gln Val Leu
            325                 330                 335

Asp Leu Ser Tyr Asn Leu Leu Glu Asp Leu Pro Ser Phe Ser Val Cys
            340                 345                 350

Gln Lys Leu Gln Lys Ile Asp Leu Arg His Asn Glu Ile Tyr Glu Ile
            355                 360                 365

Lys Val Asp Thr Phe Gln Gln Leu Leu Ser Leu Arg Ser Leu Asn Leu
            370                 375                 380

Ala Trp Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
            405                 410                 415

Pro Ile Thr Gly Leu His Gly Leu Thr His Leu Lys Leu Thr Gly Asn
            420                 425                 430

His Ala Leu Gln Ser Leu Ile Ser Ser Glu Asn Phe Pro Glu Leu Lys
            435                 440                 445

Val Ile Glu Met Pro Tyr Ala Tyr Gln Cys Cys Ala Phe Gly Val Cys
            450                 455                 460

Glu Asn Ala Tyr Lys Ile Ser Asn Gln Trp Asn Lys Gly Asp Asn Ser
465                 470                 475                 480

Ser Met Asp Asp Leu His Lys Lys Asp Ala Gly Met Phe Gln Ala Gln
            485                 490                 495

Asp Glu Arg Asp Leu Glu Asp Phe Leu Leu Asp Phe Glu Glu Asp Leu
            500                 505                 510

Lys Ala Leu His Ser Val Gln Cys Ser Pro Ser Pro Gly Pro Phe Lys
            515                 520                 525

Pro Cys Glu His Leu Leu Asp Gly Trp Gly Arg Ala Gln Val Thr Asp
            530                 535                 540

Lys Thr His Thr Cys Pro Pro Cys Pro Ala Pro Glu Leu Leu Gly Gly
545                 550                 555                 560
```

```
Pro Ser Val Phe Leu Phe Pro Pro Lys Pro Lys Asp Thr Leu Met Ile
            565             570             575

Ser Arg Thr Pro Glu Val Thr Cys Val Val Asp Val Ser His Glu
        580             585             590

Asp Pro Glu Val Lys Phe Asn Trp Tyr Val Asp Gly Val Glu Val His
        595             600             605

Asn Ala Lys Thr Lys Pro Arg Glu Glu Gln Tyr Asn Ser Thr Tyr Arg
    610             615             620

Val Val Ser Val Leu Thr Val Leu His Gln Asp Trp Leu Asn Gly Lys
625             630             635             640

Glu Tyr Lys Cys Lys Val Ser Asn Lys Ala Leu Pro Ala Pro Ile Glu
            645             650             655

Lys Thr Ile Ser Lys Ala Lys Gly Gln Pro Arg Glu Pro Gln Val Tyr
            660             665             670

Thr Leu Pro Pro Ser Arg Glu Glu Met Thr Lys Asn Gln Val Ser Leu
            675             680             685

Thr Cys Leu Val Lys Gly Phe Tyr Pro Ser Asp Ile Ala Val Glu Trp
        690             695             700

Glu Ser Asn Gly Gln Pro Glu Asn Asn Tyr Lys Thr Thr Pro Pro Val
705             710             715             720

Leu Asp Ser Asp Gly Ser Phe Phe Leu Tyr Ser Lys Leu Thr Val Asp
                725             730             735

Lys Ser Arg Trp Gln Gln Gly Asn Val Phe Ser Cys Ser Val Met His
            740             745             750

Glu Ala Leu His Asn His Tyr Thr Gln Lys Ser Leu Ser Leu Ser Pro
        755             760             765

Gly Lys
770
```

ANTI-LGR5 ANTIBODIES AND USES THEREOF

This application is a continuation of International Application No. PCT/US2015/035111, filed Jun. 10, 2015, which claims the benefit of U.S. Provisional Application No. 62/010,637, filed Jun. 11, 2014, each of which is incorporated by reference herein in its entirety for any purpose.

SEQUENCE LISTING

The present application is filed with a Sequence Listing in electronic format. The Sequence Listing is provided as a file entitled "2016-11-29_01146-0035-00US_SequenceListing.txt" created on Nov. 28, 2016, which is 125,306 bytes in size. The information in the electronic format of the sequence listing is incorporated herein by reference in its entirety.

FIELD OF THE INVENTION

The present invention relates to anti-LgR5 antibodies and methods of using the same.

BACKGROUND

The cancer stem cell hypothesis posits that similar to normal tissue, a distinct subset of specialized cells has the capacity to self-renew and continuously populates the tumor. Cancer stem cells (CSCs) are implicated in tumor initiation, progression, metastasis and relapse making them desirable targets for therapeutic intervention.

One of the most well-characterized tissue stem cell populations is the leucine-rich repeat-containing G protein-coupled receptor 5 (Lgr5) crypt cells in the gastrointestinal tract which give rise to all the differentiated cell types within the homeostatic intestinal epithelia. LgR5 is a seven-transmembrane protein found on the surface of actively cycling intestinal stem cells (ISCs). Human LgR5 is a 907 amino acid protein, of which ~540 amino acids are predicted to be in the extracellular space following cleavage of the amino-terminal signal sequence. LgR5 comprises 17 imperfect leucine-rich repeat motifs in the ectodomain, and a cysteine-rich region located between the leucine-rich repeats and the first transmembrane domain.

LgR5-expressing ISCs are sensitive to Wnt modulation and are primarily responsible for homeostatic regeneration of the intestinal epithelium. Elimination of LgR5-expressing cells in mice does not affect homeostasis of intestinal epithelium, however, suggesting that other cell types can compensate for loss of this cell population. Tian et al., Nature 478: 255-259 (2011). R-spondins enhance WNT signaling by WNT3A, and all four R-spondins, RSPO1, RSPO2, RSPO3, and RSPO4, are able to bind to LgR5. Lau et al., Nature 476: 293-297 (2011).

LgR5+ cells are proposed also to serve as the cells of origin for intestinal cancers and act as CSCs suggesting that elimination of the LgR5+ cells could have a profound impact on tumor growth and maintenance.

Lineage tracing of APC mutant tumors from LgR5+ cells demonstrates that multiple cell types in intestinal tumors are derived from an LgR5+ progenitor. Moreover LgR5+ cells are proposed to initiate and continuously contribute progeny to the tumor mass, suggesting that elimination of the LgR5+ cells could have a profound impact on tumor growth and maintenance. However, a long-standing issue in determining the expression of LgR5 has been the lack of a quality Immunohistochemistry (IHC) reactive antibody.

There is a need in the art for agents that target LgR5 for the diagnosis and treatment of LgR5-associated conditions, such as cancer. The invention fulfills that need and provides other benefits.

SUMMARY

Anti-LgR5 antibodies and immunoconjugates and methods of using the same are provided. Anti-LgR5 antibodies useful for immunohistochemistry are provided.

In some embodiments, an isolated antibody that binds to LgR5 is provided. In some embodiments, the antibody comprises: (a) HVR-H3 comprising the amino acid sequence of SEQ ID NO: 14, HVR-L3 comprising the amino acid sequence of SEQ ID NO: 11, and HVR-H2 comprising the amino acid sequence of SEQ ID NO: 13; or (b) HVR-H3 comprising the amino acid sequence of SEQ ID NO: 20, HVR-L3 comprising the amino acid sequence of SEQ ID NO: 17, and HVR-H2 comprising the amino acid sequence of SEQ ID NO: 19. In some embodiments, the antibody comprises: (a) HVR-H1 comprising the amino acid sequence of SEQ ID NO: 12, HVR-H2 comprising the amino acid sequence of SEQ ID NO: 13, and HVR-H3 comprising the amino acid sequence of SEQ ID NO: 14; or (b) HVR-H1 comprising the amino acid sequence of SEQ ID NO: 18, HVR-H2 comprising the amino acid sequence of SEQ ID NO: 19, and HVR-H3 comprising the amino acid sequence of SEQ ID NO: 20. In some embodiments, the antibody comprises: (a) HVR-L1 comprising the amino acid sequence of SEQ ID NO: 9, HVR-L2 comprising the amino acid sequence of SEQ ID NO: 10, and HVR-L3 comprising the amino acid sequence of SEQ ID NO: 11; or (b) HVR-L1 comprising the amino acid sequence of SEQ ID NO: 15, HVR-L2 comprising the amino acid sequence of SEQ ID NO: 16, and HVR-L3 comprising the amino acid sequence of SEQ ID NO: 17.

In some embodiments, the antibody comprises: (a) HVR-H1 comprising the amino acid sequence of SEQ ID NO: 12, HVR-H2 comprising the amino acid sequence of SEQ ID NO: 13, HVR-H3 comprising the amino acid sequence of SEQ ID NO: 14, HVR-L1 comprising the amino acid sequence of SEQ ID NO: 9, HVR-L2 comprising the amino acid sequence of SEQ ID NO: 10, and HVR-L3 comprising the amino acid sequence of SEQ ID NO: 11; or (b) HVR-H1 comprising the amino acid sequence of SEQ ID NO: 18, HVR-H2 comprising the amino acid sequence of SEQ ID NO: 19, HVR-H3 comprising the amino acid sequence of SEQ ID NO: 20, HVR-L1 comprising the amino acid sequence of SEQ ID NO: 15, HVR-L2 comprising the amino acid sequence of SEQ ID NO: 16, and HVR-L3 comprising the amino acid sequence of SEQ ID NO: 17.

In some embodiments, the antibody comprises: (a)(i) a VH sequence having at least 95% sequence identity to the amino acid sequence of SEQ ID NO: 6; (ii) a VL sequence having at least 95% sequence identity to the amino acid sequence of SEQ ID NO: 5; or (iii) a VH sequence as in (i) and a VL sequence as in (ii); or (b)(i) a VH sequence having at least 95% sequence identity to the amino acid sequence of SEQ ID NO: 8; (ii) a VL sequence having at least 95% sequence identity to the amino acid sequence of SEQ ID NO: 7; or (iii) a VH sequence as in (i) and a VL sequence as in (ii).

In some embodiments, the antibody comprises a VH sequence of SEQ ID NO: 6 or SEQ ID NO: 8. In some embodiments, the antibody comprises a VL sequence of SEQ ID NO: 7 or SEQ ID NO: 9.

In some embodiments, the antibody is a monoclonal antibody. In some embodiments, the antibody is a mouse, rabbit, human, humanized, or chimeric antibody. In some embodiments, the antibody is an IgG selected from IgG1, IgG2a, IgG2b, IgG3, and IgG4.

In some embodiments, nucleic acids encoding an antibody described herein are provided. In some embodiments, a host cell comprising a nucleic acid encoding an antibody described herein is provided. In some embodiments, methods of producing antibodies are provided, comprising culturing a host cell comprising a nucleic acid encoding an antibody described herein.

In some embodiments, an immunoconjugate is provided comprising an antibody described herein and a cytotoxic agent. In some embodiments, a pharmaceutical formulation is provided comprising an immunoconjugate comprising an antibody described herein and a cytotoxic agent and a pharmaceutically acceptable carrier.

In some embodiments, an antibody described herein conjugated to a label is provided. In some embodiments, the label is a positron emitter. In some embodiments, the positron emitter is $^{89}$Zr.

In some embodiments, a method of detecting human LgR5 in a biological sample is provided. In some embodiments, the method comprises contacting the biological sample with an anti-LgR5 antibody described herein under conditions permissive for binding of the anti-LgR5 antibody to human LgR5. In some embodiments, the method further comprises detecting whether a complex is formed between the anti-LgR5 antibody and human LgR5 in the biological sample. In some embodiments, the biological sample is a colon cancer sample, a colorectal cancer sample, small intestine cancer sample, endometrial cancer sample, pancreatic cancer sample, or ovarian cancer sample.

In some embodiments, methods for detecting a LgR5-positive cancer are provided. In some embodiments, a method comprises (i) administering a labeled anti-LgR5 antibody to a subject having or suspected of having a LgR5-positive cancer, wherein the labeled anti-LgR5 antibody comprises an anti-LgR5 antibody described herein, and (ii) detecting the labeled anti-LgR5 antibody in the subject, wherein detection of the labeled anti-LgR5 antibody indicates a LgR5-positive cancer in the subject. In some embodiments, the labeled anti-LgR5 antibody comprises an anti-LgR5 antibody conjugated to a positron emitter. In some embodiments, the positron emitter is $^{89}$Zr.

In some embodiments, methods of identifying a cancer patient as having a LgR5-positive cancer are provided. In some embodiments, the method comprises contacting a cancer sample from the patient with an anti-LgR5 antibody described herein under conditions permissive for binding of the anti-LgR5 antibody to human LgR5. In some embodiments, the method further comprises detecting whether a complex is formed between the anti-LgR5 antibody and human LgR5 in the cancer sample. In some embodiments, the cancer patient is identified as having a LgR5-positive cancer if a complex is between the anti-LgR5 antibody and human LgR5 in the cancer sample is detected. In some embodiments, the cancer sample is a colon cancer sample, a colorectal cancer sample, small intestine cancer sample, endometrial cancer sample, pancreatic cancer sample, or ovarian cancer sample.

In some embodiments, methods of selecting cancer patients for treatment with an immunoconjugate comprising an anti-LgR5 antibody are provided. In some embodiments, a method comprises determining the level of LgR5 expression in a cancer sample from the patient using immunohistochemistry (IHC). In some embodiments, an elevated level of LgR5 expression indicates that the cancer patient is more likely to benefit from treatment with an immunoconjugate comprising an anti-LgR5 antibody. In some embodiments, an elevated level of LgR5 expression is 2+ or 3+ staining by IHC. In some embodiments, an elevated level of LgR5 expression is 3+ staining by IHC. In some embodiments, IHC is performed using an antibody described herein. In some embodiments, the cancer sample is a colon cancer sample, a colorectal cancer sample, small intestine cancer sample, endometrial cancer sample, pancreatic cancer sample, or ovarian cancer sample.

In some embodiments, a method of selecting a cancer patient for treatment with an immunoconjugate comprising an anti-LgR5 antibody are provided, wherein the method comprises contacting a cancer sample from the patient with an anti-LgR5 antibody described herein under conditions permissive for binding of the anti-LgR5 antibody to human LgR5, and detecting whether a complex is formed between the anti-LgR5 antibody and human LgR5 in the cancer sample. In some embodiments, the cancer patient is selected if a complex is between the anti-LgR5 antibody and human LgR5 in the cancer sample is detected. In some embodiments, the cancer sample is a colon cancer sample, a colorectal cancer sample, small intestine cancer sample, endometrial cancer sample, pancreatic cancer sample, or ovarian cancer sample.

In some embodiments, methods of treating cancer patients are provided, comprising administering to the patient a therapeutically effective amount of an immunoconjugate comprising an anti-LgR5 antibody, wherein a cancer sample from the patient has been determined to have an elevated level of LgR5 expression using immunohistochemistry (IHC). In some embodiments, an elevated level of LgR5 expression is 2+ or 3+ staining by IHC. In some embodiments, an elevated level of LgR5 expression is 3+ staining by IHC. In some embodiments, IHC is performed using an antibody described herein. In some embodiments, the cancer sample is a colon cancer sample, a colorectal cancer sample, small intestine cancer sample, endometrial cancer sample, pancreatic cancer sample, or ovarian cancer sample.

In some embodiments, the immunoconjugate comprises an anti-LgR5 antibody comprising: (a) HVR-H1 comprising the amino acid sequence of SEQ ID NO: 55, HVR-H2 comprising the amino acid sequence of SEQ ID NO: 56, HVR-H3 comprising the amino acid sequence of SEQ ID NO: 57, HVR-L1 comprising the amino acid sequence of SEQ ID NO: 52; HVR-L2 comprising the amino acid sequence of SEQ ID NO: 53; and HVR-L3 comprising the amino acid sequence of SEQ ID NO: 54; or (b) HVR-H1 comprising the amino acid sequence of SEQ ID NO: 73, HVR-H2 comprising the amino acid sequence of SEQ ID NO: 74, HVR-H3 comprising the amino acid sequence of SEQ ID NO: 75, HVR-L1 comprising the amino acid sequence of SEQ ID NO: 70; HVR-L2 comprising the amino acid sequence of SEQ ID NO: 71; and HVR-L3 comprising the amino acid sequence of SEQ ID NO: 72; or (c) HVR-H1 comprising the amino acid sequence of SEQ ID NO: 79, HVR-H2 comprising the amino acid sequence of SEQ ID NO: 80, HVR-H3 comprising the amino acid sequence of SEQ ID NO: 81, HVR-L1 comprising the amino acid sequence of SEQ ID NO: 76; HVR-L2 comprising the amino acid sequence of SEQ ID NO: 77; and HVR-L3 comprising the amino acid sequence of SEQ ID NO: 78; or (d) HVR-H1 comprising the amino acid sequence of SEQ ID NO: 85, HVR-H2 comprising the amino acid sequence of SEQ ID NO: 86, HVR-H3 comprising the amino acid sequence of SEQ ID NO: 87, HVR-L1 comprising the amino acid sequence of SEQ ID NO: 82; HVR-L2 comprising the amino acid sequence of SEQ ID NO: 83; and HVR-L3 comprising the amino acid sequence of SEQ ID NO: 84. In some embodiments, the immunoconjugate comprises an anti-LgR5 antibody comprising (a) a VH sequence of SEQ ID NO: 33 and a VL sequence of SEQ ID NO: 32; or (b) a VH sequence of SEQ ID NO: 51 and a VL sequence of SEQ ID NO: 50. In some embodiments, the immunoconjugate comprises an anti-LgR5 antibody conjugated to a cytotoxic agent.

BRIEF DESCRIPTION OF THE FIGURES

FIGS. 4A and 4B show an alignment of the (A) light chain and (B) heavy chain of antibody LGR5.1-12 ((A) SEQ ID NO: 5 and (B) SEQ ID NO: 6) and antibody LGR5.26-1 ((A) SEQ ID NO: 7 and (B) SEQ ID NO: 8). The contact region, Chothia, and Kabat complementarity determining regions (CDRs, also referred to as hypervariable regions, or HVRs) are indicated. The Kabat HVRs are underlined.

FIGS. 6A, 6B, 6C, and 6D show detection of LgR5 on the surface of (A) LoVo X 1.1 xenograft tumor cells and (B) D5124 xenograft tumor cells by FACS using antibody YW353, and staining of (C) LoVo X 1.1 xenograft tumors and (D) D5124 xenograft tumors by immunohistochemistry, using antibody LGR5.1-12, as described in Example F.

FIGS. 7A, 7B, 7C, and 7D show exemplary 0, 1+, 2+, and 3+ staining of colon tumors using antibody LGR5.1-12, as described in Example G.

FIGS. 8A and 8B show staining of a CXF233 xenograft tumor sample using (A) antibody LGR5.1-12 and (B) antibody LGR5.26-1, as described in Example H.

DETAILED DESCRIPTION OF EMBODIMENTS OF THE INVENTION

I. Definitions

Figure 1:
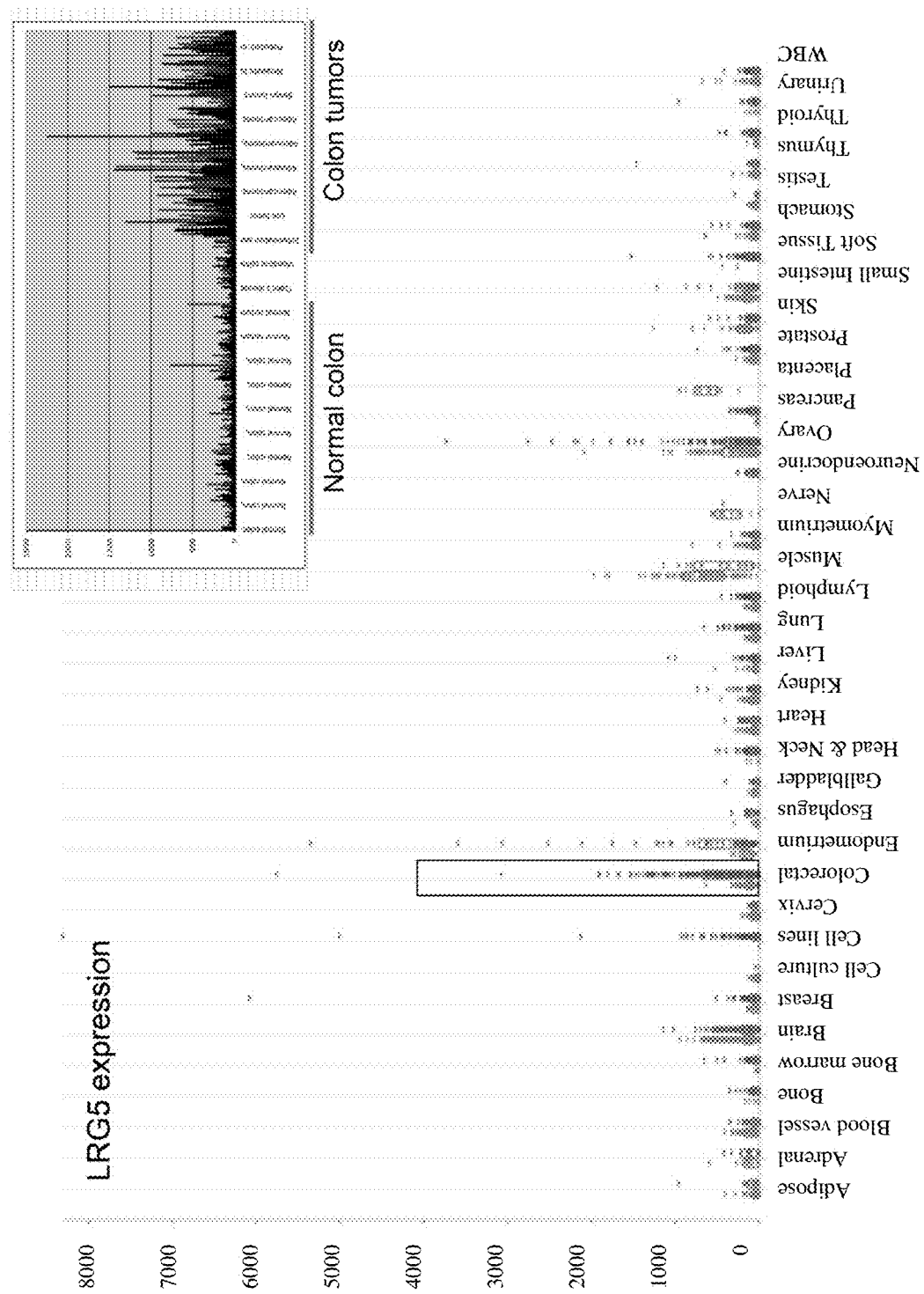
FIG. 1 shows a graphic representation of the levels of human LgR5 gene expression in various tissues, as described in Example A. The inset in FIG. 1 shows a graphic representation of the levels of human LgR5 gene expression in normal colon tissues and colon tumors, as described in Example A.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-LgR5 antibody" and "an antibody that binds to LgR5" refer to an antibody that is capable of binding LgR5 with sufficient affinity such that the antibody is useful as a diagnostic and/or therapeutic agent in targeting LgR5. In one embodiment, the extent of binding of an anti-LgR5 antibody to an unrelated, non-LgR5 protein is less than about 10% of the binding of the antibody to LgR5 as measured, e.g., by a radioimmunoassay (RIA) or by scatchard analysis or by surface plasmon resonance, such as, for example, Biacore. In certain embodiments, an antibody that binds to LgR5 has a dissociation constant (Kd) of ≤1 µM, ≤100 nM, ≤10 nM, ≤5 Nm, ≤4 nM, ≤3 nM, ≤2 nM, ≤1 nM, ≤0.1 nM, ≤0.01 nM, or ≤0.001 nM (e.g., $10^{-8}$ M or less, e.g. from $10^{-8}$ M to $10^{-13}$ M, e.g., from $10^{-9}$ M to $10^{-13}$ M). In certain embodiments, an anti-LgR5 antibody binds to an epitope of LgR5 that is conserved among LgR5 from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "antibody drug conjugate" (ADC) as used herein is equivalent to the term "immunoconjugate".

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "glycosylated forms of LgR5" refers to naturally occurring forms of LgR5 that are post-translationally modified by the addition of carbohydrate residues.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "rabbit antibody" is one which possesses an amino acid sequence which corresponds to that of an antibody produced by a rabbit or a rabbit cell or derived from a non-rabbit source that utilizes rabbit antibody repertoires or other rabbit antibody-encoding sequences.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda, Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent. An immunoconjugate is equivalent to the term "antibody drug conjugate" (ADC).

An "individual" or "patient" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-LgR5 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "LgR5," as used herein, refers to any native, mature LgR5 which results from processing of an LgR5 precursor protein in a cell. The term includes LgR5 from any vertebrate source, including mammals such as primates (e.g. humans and cynomolgus or rhesus monkeys) and rodents (e.g., mice and rats), unless otherwise indicated. The term also includes naturally occurring variants of LgR5, e.g., splice variants or allelic variants. The amino acid sequence of an exemplary human LgR5 precursor protein, with signal sequence (amino acids 1-21) is shown in SEQ ID NO: 21. The amino acid sequence of an exemplary mature human LgR5 is shown in SEQ ID NO: 22. The predicted sequence for amino acids 33 to 907 of an exemplary cynomolgus monkey LgR5 is shown in SEQ ID NO: 23. The amino acid sequences for exemplary rat LgR5 precursor (with signal sequence, amino acids 1-21) and mature sequences are shown in SEQ ID NOs: 24 and 25, respectively. The amino acid sequences for exemplary mouse LgR5 precursor (with signal sequence, amino acids 1-21) and mature sequences are shown in SEQ ID NOs: 26 and 27, respectively.

The term "LgR5-positive cancer" refers to a cancer comprising cells that express LgR5 on their surface. For the purposes of determining whether a cell expresses LgR5 on the surface, LgR5 mRNA expression is considered to correlate to LgR5 expression on the cell surface. In some embodiments, expression of LgR5 mRNA is determined by a method selected from in situ hybridization and RT-PCR (including quantitative RT-PCR). Alternatively, expression of LgR5 on the cell surface can be determined, for example, using antibodies to LgR5 in a method such as immunohistochemistry, FACS, etc.

The term "LgR5-positive cancer cell" refers to a cancer cell that expresses LgR5 on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A "platinum complex" as used herein refers to anti-cancer chemotherapy drugs such as, for example, but not limited to, cisplatin, oxaliplatin, carboplatin, iproplatin, satraplatin, CI-973, AZ0473, DWA2114R, nedaplatin, and sprioplatin, which exert efficacy against tumors based on their ability to covalently bind to DNA.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, anti-LgR5 antibodies are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on antibodies that bind to LgR5 and immunoconjugates comprising such antibodies. Antibodies and immunoconjugates of the invention are useful, e.g., for the diagnosis or treatment of LgR5-positive cancers.

A. Exemplary Anti-LgR5 Antibodies

In some embodiments, the invention provides isolated antibodies that bind to LgR5. LgR5 is a seven-transmembrane protein found, for example, on the surface of actively cycling intestinal stem cells. LgR5 is expressed in about 77% of colon tumor sections examined See, e.g., PCT Publication No. WO 2013/149159. An exemplary naturally occurring human LgR5 precursor protein sequence, with signal sequence (amino acids 1-21) is provided in SEQ ID NO: 21, and the corresponding mature LgR5 protein sequence is shown in SEQ ID NO: 22 (corresponding to amino acids 22-907 of SEQ ID NO: 21).

In some embodiments, the invention provides isolated antibodies that bind to an epitope within amino acids 22 to 322 of human LgR5. In some embodiments, the invention provides isolated antibodies that bind to an epitope within the human LgR5 extracellular domain that is outside of amino acids 22 to 322. In some embodiments, the invention provides isolated antibodies that bind to an epitope within amino acids 323 to 558 of human LgR5.

Antibody αLgR5.1-12 and Other Embodiments

In one aspect, the invention provides an anti-LgR5 antibody comprising at least one, two, three, four, five, or six HVRs selected from (a) HVR-H1 comprising the amino acid sequence of SEQ ID NO:12; (b) HVR-H2 comprising the amino acid sequence of SEQ ID NO:13; (c) HVR-H3 comprising the amino acid sequence of SEQ ID NO:14; (d) HVR-L1 comprising the amino acid sequence of SEQ ID NO:9; (e) HVR-L2 comprising the amino acid sequence of SEQ ID NO:10; and (f) HVR-L3 comprising the amino acid sequence of SEQ ID NO:11.

In one aspect, the invention provides an antibody comprising at least one, at least two, or all three VH HVR sequences selected from (a) HVR-H1 comprising the amino acid sequence of SEQ ID NO:12; (b) HVR-H2 comprising the amino acid sequence of SEQ ID NO:13; and (c) HVR-H3 comprising the amino acid sequence of SEQ ID NO:14. In one embodiment, the antibody comprises HVR-H3 comprising the amino acid sequence of SEQ ID NO:14. In another embodiment, the antibody comprises HVR-H3 comprising the amino acid sequence of SEQ ID NO:14 and HVR-L3 comprising the amino acid sequence of SEQ ID NO:11. In a further embodiment, the antibody comprises HVR-H3 comprising the amino acid sequence of SEQ ID NO:14, HVR-L3 comprising the amino acid sequence of SEQ ID NO:11, and HVR-H2 comprising the amino acid sequence of SEQ ID NO:13. In a further embodiment, the antibody comprises (a) HVR-H1 comprising the amino acid sequence of SEQ ID NO:12; (b) HVR-H2 comprising the amino acid sequence of SEQ ID NO:13; and (c) HVR-H3 comprising the amino acid sequence of SEQ ID NO:14.

In another aspect, the invention provides an antibody comprising at least one, at least two, or all three VL HVR sequences selected from (a) HVR-L1 comprising the amino acid sequence of SEQ ID NO:9; (b) HVR-L2 comprising the amino acid sequence of SEQ ID NO:10; and (c) HVR-L3 comprising the amino acid sequence of SEQ ID NO:11. In one embodiment, the antibody comprises (a) HVR-L1 comprising the amino acid sequence of SEQ ID NO:9; (b) HVR-L2 comprising the amino acid sequence of SEQ ID NO:10; and (c) HVR-L3 comprising the amino acid sequence of SEQ ID NO:11.

In another aspect, an antibody of the invention comprises (a) a VH domain comprising at least one, at least two, or all three VH HVR sequences selected from (i) HVR-H1 comprising the amino acid sequence of SEQ ID NO:12, (ii) HVR-H2 comprising the amino acid sequence of SEQ ID NO:13, and (iii) HVR-H3 comprising an amino acid sequence selected from SEQ ID NO:14; and (b) a VL domain comprising at least one, at least two, or all three VL HVR sequences selected from (i) HVR-L1 comprising the amino acid sequence of SEQ ID NO:9, (ii) HVR-L2 comprising the amino acid sequence of SEQ ID NO:10, and (c) HVR-L3 comprising the amino acid sequence of SEQ ID NO:11.

In another aspect, the invention provides an antibody comprising (a) HVR-H1 comprising the amino acid sequence of SEQ ID NO:12; (b) HVR-H2 comprising the amino acid sequence of SEQ ID NO:13; (c) HVR-H3 comprising the amino acid sequence of SEQ ID NO:14; (d) HVR-L1 comprising the amino acid sequence of SEQ ID NO:9; (e) HVR-L2 comprising the amino acid sequence of SEQ ID NO:10; and (f) HVR-L3 comprising the amino acid sequence of SEQ ID NO:11.

In any of the above embodiments, an anti-LgR5 antibody is humanized. In one embodiment, an anti-LgR5 antibody comprises HVRs as in any of the above embodiments, and further comprises a human acceptor framework, e.g. a human immunoglobulin framework or a human consensus framework. In some embodiments, an anti-LgR5 antibody comprises the HVRs described above and rabbit framework regions.

In another aspect, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:6. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in SEQ ID NO:6. In certain embodiments, substitutions, insertions, or deletions occur in regions outside the HVRs (i.e., in the FRs). Optionally, the anti-LgR5 antibody comprises the VH sequence of SEQ ID NO:6, including post-translational modifications of that sequence. In a particular embodiment, the VH comprises one, two or three HVRs selected from: (a) HVR-H1 comprising the amino acid sequence of SEQ ID NO:12, (b) HVR-H2 comprising the amino acid sequence of SEQ ID NO:13, and (c) HVR-H3 comprising the amino acid sequence of SEQ ID NO:14.

In another aspect, an anti-LgR5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:5. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in SEQ ID NO:5. In certain embodiments, the substitutions, insertions, or deletions occur in regions outside the HVRs (i.e., in the FRs). Optionally, the anti-LgR5 antibody comprises the VL sequence of SEQ ID NO:5, including post-translational modifications of that sequence. In a particular embodiment, the VL comprises one, two or three HVRs selected from (a) HVR-L1 comprising the amino acid sequence of SEQ ID NO:9; (b) HVR-L2 comprising the amino acid sequence of SEQ ID NO:10; and (c) HVR-L3 comprising the amino acid sequence of SEQ ID NO:11.

In another aspect, an anti-LgR5 antibody is provided, wherein the antibody comprises a VH as in any of the embodiments provided above, and a VL as in any of the embodiments provided above. In one embodiment, the antibody comprises the VH and VL sequences in SEQ ID NO:6 and SEQ ID NO:5, respectively, including post-translational modifications of those sequences.

In a further aspect, the invention provides an antibody that binds to the same epitope as an anti-LgR5 antibody provided herein. For example, in certain embodiments, an antibody is provided that binds to the same epitope as an anti-LgR5 antibody comprising a VH sequence of SEQ ID NO:6 and a VL sequence of SEQ ID NO:5. In some embodiments, an antibody that competes with an anti-LgR5 antibody comprising a VH sequence of SEQ ID NO:6 and a VL sequence of SEQ ID NO:5 for binding to human LgR5 is provided. In some embodiments, an antibody that competes with an anti-LgR5 antibody comprising a VH sequence of SEQ ID NO:6 and a VL sequence of SEQ ID NO:5 for binding to human LgR5 is provided. In some embodiments, an antibody that binds an epitope within the LgR5 extracellular domain that is outside of amino acids 22 to 322 is provided. In some embodiments, an antibody that does not compete for binding to human LgR5 with antibody either huYW353 or 8E11. In some embodiments, an antibody that binds to an epitope within amino acids 323 to 558 of human LgR5 is provided.

In a further aspect of the invention, an anti-LgR5 antibody according to any of the above embodiments is a monoclonal antibody, including a chimeric, humanized or human antibody. In one embodiment, an anti-LgR5 antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In a further aspect, an anti-LgR5 antibody according to any of the above embodiments may incorporate any of the features, singly or in combination, as described in Sections 1-7 below:

Antibody αLgR5.26-1 and Other Embodiments

In one aspect, the invention provides an anti-LgR5 antibody comprising at least one, two, three, four, five, or six HVRs selected from (a) HVR-H1 comprising the amino acid sequence of SEQ ID NO:18; (b) HVR-H2 comprising the amino acid sequence of SEQ ID NO:19; (c) HVR-H3 comprising the amino acid sequence of SEQ ID NO:20; (d) HVR-L1 comprising the amino acid sequence of SEQ ID NO:15; (e) HVR-L2 comprising the amino acid sequence of SEQ ID NO:16; and (f) HVR-L3 comprising the amino acid sequence of SEQ ID NO:17.

In one aspect, the invention provides an antibody comprising at least one, at least two, or all three VH HVR sequences selected from (a) HVR-H1 comprising the amino acid sequence of SEQ ID NO:18; (b) HVR-H2 comprising the amino acid sequence of SEQ ID NO:19; and (c) HVR-H3 comprising the amino acid sequence of SEQ ID NO:20. In one embodiment, the antibody comprises HVR-H3 comprising the amino acid sequence of SEQ ID NO:20. In another embodiment, the antibody comprises HVR-H3 comprising the amino acid sequence of SEQ ID NO:20, and HVR-L3 comprising the amino acid sequence of SEQ ID NO:17. In a further embodiment, the antibody comprises HVR-H3 comprising the amino acid sequence of SEQ ID NO:20, HVR-L3 comprising the amino acid sequence of SEQ ID NO:17, and HVR-H2 comprising the amino acid sequence of SEQ ID NO:19. In a further embodiment, the antibody comprises (a) HVR-H1 comprising the amino acid sequence of SEQ ID NO:18; (b) HVR-H2 comprising the amino acid sequence of SEQ ID NO:19; and (c) HVR-H3 comprising the amino acid sequence of SEQ ID NO:20.

In another aspect, the invention provides an antibody comprising at least one, at least two, or all three VL HVR sequences selected from (a) HVR-L1 comprising the amino acid sequence of SEQ ID NO:15; (b) HVR-L2 comprising the amino acid sequence of SEQ ID NO:16; and (c) HVR-L3 comprising the amino acid sequence of SEQ ID NO:17. In one embodiment, the antibody comprises (a) HVR-L1 comprising the amino acid sequence of SEQ ID NO:15; (b) HVR-L2 comprising the amino acid sequence of SEQ ID NO:16; and (c) HVR-L3 comprising the amino acid sequence of SEQ ID NO:17.

In another aspect, an antibody of the invention comprises (a) a VH domain comprising at least one, at least two, or all three VH HVR sequences selected from (i) HVR-H1 comprising the amino acid sequence of SEQ ID NO:18, (ii) HVR-H2 comprising the amino acid sequence of SEQ ID NO:19, and (iii) HVR-H3 comprising the amino acid sequence of SEQ ID NO:20; and (b) a VL domain comprising at least one, at least two, or all three VL HVR sequences selected from (i) HVR-L1 comprising the amino acid sequence of SEQ ID NO:15, (ii) HVR-L2 comprising the amino acid sequence of SEQ ID NO:16, and (c) HVR-L3 comprising the amino acid sequence of SEQ ID NO:17.

In another aspect, the invention provides an antibody comprising (a) HVR-H1 comprising the amino acid sequence of SEQ ID NO:18; (b) HVR-H2 comprising the amino acid sequence of SEQ ID NO:19; (c) HVR-H3 comprising the amino acid sequence of SEQ ID NO:20; (d) HVR-L1 comprising the amino acid sequence of SEQ ID NO:15; (e) HVR-L2 comprising the amino acid sequence of SEQ ID NO:16; and (f) HVR-L3 comprising an amino acid sequence selected from SEQ ID NO:17.

In any of the above embodiments, an anti-LgR5 antibody is humanized. In one embodiment, an anti-LgR5 antibody comprises HVRs as in any of the above embodiments, and further comprises an acceptor human framework, e.g. a human immunoglobulin framework or a human consensus framework. In some embodiments, an anti-LgR5 antibody comprises the HVRs described above and rabbit framework regions.

In another aspect, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:8. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in SEQ ID NO:8. In certain embodiments, substitutions, insertions, or deletions occur in regions outside the HVRs (i.e., in the FRs). Optionally, the anti-LgR5 antibody comprises the VH sequence of SEQ ID NO:8, including post-translational modifications of that sequence. In a particular embodiment, the VH comprises one, two or three HVRs selected from: (a) HVR-H1 comprising the amino acid sequence of SEQ ID NO:18, (b) HVR-H2 comprising the amino acid sequence of SEQ ID NO:19, and (c) HVR-H3 comprising the amino acid sequence of SEQ ID NO:20.

In another aspect, an anti-LgR5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:7. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in SEQ ID NO:7. In certain embodiments, the substitutions, insertions, or deletions occur in regions outside the HVRs (i.e., in the FRs). Optionally, the anti-LgR5 antibody comprises the VL sequence of SEQ ID NO:7, including post-translational modifications of that sequence. In a particular embodiment, the VL comprises one, two or three HVRs selected from (a) HVR-L1 comprising the amino acid sequence of SEQ ID NO:15; (b) HVR-L2 comprising the amino acid sequence of SEQ ID NO:8; and (c) HVR-L3 comprising the amino acid sequence of SEQ ID NO:17.

In another aspect, an anti-LgR5 antibody is provided, wherein the antibody comprises a VH as in any of the embodiments provided above, and a VL as in any of the embodiments provided above. In one embodiment, the antibody comprises the VH and VL sequences in SEQ ID NO:8 and SEQ ID NO:7, respectively, including post-translational modifications of those sequences.

In a further aspect, the invention provides an antibody that binds to the same epitope as an anti-LgR5 antibody provided herein. For example, in certain embodiments, an antibody is provided that binds to the same epitope as an anti-LgR5 antibody comprising a VH sequence of SEQ ID NO:8 and a VL sequence of SEQ ID NO:7. In some embodiments, an antibody that competes with an anti-LgR5 antibody comprising a VH sequence of SEQ ID NO:8 and a VL sequence of SEQ ID NO:7 for binding to human LgR5 is provided. In some embodiments, an antibody that competes with an anti-LgR5 antibody comprising a VH sequence of SEQ ID NO:8 and a VL sequence of SEQ ID NO:7 for binding to an epitope within amino acids 22 to 322 of human LgR5 is provided.

In a further aspect of the invention, an anti-LgR5 antibody according to any of the above embodiments is a monoclonal antibody, including a chimeric, humanized or human antibody. In one embodiment, an anti-LgR5 antibody is an antibody fragment, e.g., a Fv, Fab, Fab', scFv, diabody, or F(ab')$_2$ fragment. In another embodiment, the antibody is a substantially full length antibody, e.g., an IgG2a antibody or other antibody class or isotype as defined herein.

In a further aspect, an anti-LgR5 antibody according to any of the above embodiments may incorporate any of the features, singly or in combination, as described in Sections 1-7 below:

Antibody 8E11 and Other Embodiments

In some embodiments, the invention provides an anti-LgR5 antibody comprising at least one, two, three, four, five, or six HVRs selected from (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54.

In another aspect, the invention provides an antibody comprising (a) HVR-H1 comprising the amino acid sequence of SEQ ID NO: 55; (b) HVR-H2 comprising the amino acid sequence of SEQ ID NO: 56; (c) HVR-H3 comprising the amino acid sequence of SEQ ID NO: 57; (d) HVR-L1 comprising the amino acid sequence of SEQ ID NO: 52; (e) HVR-L2 comprising the amino acid sequence of SEQ ID NO: 53; and (f) HVR-L3 comprising the amino acid sequence of SEQ ID NO: 54.

In any of the above embodiments, an anti-LgR5 antibody is humanized. In one embodiment, an anti-LgR5 antibody comprises HVRs as in any of the above embodiments, and further comprises a human acceptor framework, e.g. a human immunoglobulin framework or a human consensus framework. In certain embodiments, the human acceptor framework is the human VL kappa IV consensus (VL$_{KIV}$) framework and/or the VH framework VH$_1$. In certain embodiments, the human acceptor framework is the human VL kappa IV consensus (VL$_{KIV}$) framework and/or the VH framework VH$_1$ comprising an R71S mutation and an A78V mutation in heavy chain framework region FR3.

In some embodiments, an anti-LgR5 antibody comprises HVRs as in any of the above embodiments, and further comprises a heavy chain framework FR3 sequence selected from SEQ ID NOs: 65 to 68. In some embodiments, an anti-LgR5 antibody comprises HVRs as in any of the above embodiments, and further comprises a heavy chain framework FR3 sequence of SEQ ID NO: 66. In some such embodiments, the heavy chain variable domain framework is a modified human VH$_1$ framework having an FR3 sequence selected from SEQ ID NOs: 65 to 68. In some such embodiments, the heavy chain variable domain framework is a modified human VH$_1$ framework having an FR3 sequence of SEQ ID NO: 66.

In some embodiments, an anti-LgR5 antibody comprises HVRs as in any of the above embodiments, and further comprises a light chain framework FR3 sequence of SEQ ID NO: 61. In some such embodiments, the heavy chain variable domain framework is a modified VL kappa IV consensus (VL$_{KIV}$) framework having an FR3 sequence of SEQ ID NO: 61.

In another aspect, an anti-LgR5 antibody comprises a heavy chain variable domain (VH) sequence having at least 90%, 91%, 92%, 93%, 94%, 95%, 96%, 97%, 98%, 99%, or 100% sequence identity to an amino acid sequence selected from SEQ ID NOs: 31, 33, 35, 37, 39, 41, 43, and 45. In certain embodiments, a VH sequence having at least 90%, 91%, 92%, 93%, 94%, 95%, 96%, 97%, 98%, or 99% identity to an amino acid sequence selected from SEQ ID NOs: 31, 33, 35, 37, 39, 41, 43, and 45 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in a sequence selected from SEQ ID NOs: 31, 33, 35, 37, 39, 41, 43, and 45. In certain embodiments, a total of 1 to 5 amino acids have been substituted, inserted and/or deleted in a sequence selected from SEQ ID NOs: 31, 33, 35, 37, 39, 41, 43, and 45. In certain embodiments, substitutions, insertions, or deletions occur in regions outside the HVRs (i.e., in the FRs).

In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 31. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 33. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 35. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 37. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 39. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 41. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 43. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 45.

Optionally, the anti-LgR5 antibody comprises the VH sequence selected from SEQ ID NOs: 31, 33, 35, 37, 39, 41, 43, and 45, including post-translational modifications of that sequence. In a particular embodiment, the VH comprises one, two or three HVRs selected from: (a) HVR-H1 comprising the amino acid sequence of SEQ ID NO: 55, (b) HVR-H2 comprising the amino acid sequence of SEQ ID NO: 56, and (c) HVR-H3 comprising the amino acid sequence of SEQ ID NO: 57.

In another aspect, an anti-LgR5 antibody is provided, wherein the antibody comprises a light chain variable domain (VL) having at least 90%, 91%, 92%, 93%, 94%, 95%, 96%, 97%, 98%, 99%, or 100% sequence identity to an amino acid sequence selected from SEQ ID NOs: 30, 32, 34, 36, 38, 40, 42, and 44. In certain embodiments, a VL sequence having at least 90%, 91%, 92%, 93%, 94%, 95%, 96%, 97%, 98%, or 99% identity to an amino acid sequence selected from SEQ ID NOs: 30, 32, 34, 36, 38, 40, 42, and 44 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in an amino acid sequence selected from SEQ ID NOs: 30, 32, 34, 36, 38, 40, 42, and 44. In certain embodiments, a total of 1 to 5 amino acids have been substituted, inserted and/or deleted in an amino acid sequence selected from SEQ ID NOs: 30, 32, 34, 36, 38, 40, 42, and 44. In certain embodiments, the substitutions, insertions, or deletions occur in regions outside the HVRs (i.e., in the FRs).

In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 30. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 32. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 34. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 36. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 38. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 40. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 42. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 44.

Optionally, the anti-LgR5 antibody comprises the VL sequence of an amino acid sequence selected from SEQ ID NOs: 30, 32, 34, 36, 38, 40, 42, and 44, including post-translational modifications of that sequence. In a particular embodiment, the VL comprises one, two or three HVRs selected from (a) HVR-L1 comprising the amino acid sequence of SEQ ID NO: 52; (b) HVR-L2 comprising the amino acid sequence of SEQ ID NO: 53; and (c) HVR-L3 comprising the amino acid sequence of SEQ ID NO: 54.

In another aspect, an anti-LgR5 antibody is provided, wherein the antibody comprises a VH as in any of the embodiments provided above, and a VL as in any of the embodiments provided above. In one embodiment, the antibody comprises the VH and VL sequences in SEQ ID NO: 31 and SEQ ID NO: 30, respectively, including post-translational modifications of those sequences. In one embodiment, the antibody comprises the VH and VL sequences in SEQ ID NO: 33 and SEQ ID NO: 32, respectively, including post-translational modifications of those sequences. In one embodiment, the antibody comprises the VH and VL sequences in SEQ ID NO: 35 and SEQ ID NO: 34, respectively, including post-translational modifications of those sequences. In one embodiment, the antibody comprises the VH and VL sequences in SEQ ID NO: 37 and SEQ ID NO: 36, respectively, including post-translational modifications of those sequences. In one embodiment, the antibody comprises the VH and VL sequences in SEQ ID NO: 39 and SEQ ID NO: 39, respectively, including post-translational modifications of those sequences. In one embodiment, the antibody comprises the VH and VL sequences in SEQ ID NO: 41 and SEQ ID NO: 40, respectively, including post-translational modifications of those sequences. In one embodiment, the antibody comprises the VH and VL sequences in SEQ ID NO: 43 and SEQ ID NO: 42, respectively, including post-translational modifications of those sequences. In one embodiment, the antibody comprises the VH and VL sequences in SEQ ID NO: 45 and SEQ ID NO: 44, respectively, including post-translational modifications of those sequences.

In a further aspect, the invention provides an antibody that binds to the same epitope as an anti-LgR5 antibody provided herein. For example, in certain embodiments, an antibody is provided that binds to the same epitope as an anti-LgR5 antibody comprising a VH sequence of SEQ ID NO: 33 and a VL sequence of SEQ ID NO: 32. In certain embodiments, an antibody is provided that binds to an epitope of SEQ ID NO: 21 from, within, or overlapping amino acids 22-323. In some embodiments, an antibody is provided that binds to an epitope of SEQ ID NO: 22 from, within, or overlapping amino acids 1-312.

In a further aspect of the invention, an anti-LgR5 antibody according to any of the above embodiments is a monoclonal antibody, including a chimeric, humanized or human antibody. In one embodiment, an anti-LgR5 antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In a further aspect, an anti-LgR5 antibody according to any of the above embodiments may incorporate any of the features, singly or in combination, as described in Sections 1-7 below.

Antibody YW353 and Other Embodiments

In one aspect, the invention provides an anti-LgR5 antibody comprising at least one, two, three, four, five, or six HVRs selected from (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 82; (e) HVR-L2 comprising the amino acid sequence of SEQ ID NO: 83; and (f) HVR-L3 comprising the amino acid sequence of SEQ ID NO: 84.

In another aspect, the invention provides an antibody comprising (a) HVR-H1 comprising the amino acid sequence of SEQ ID NO: 85; (b) HVR-H2 comprising the amino acid sequence of SEQ ID NO: 86; (c) HVR-H3 comprising the amino acid sequence of SEQ ID NO: 87; (d) HVR-L1 comprising the amino acid sequence of SEQ ID NO: 82; (e) HVR-L2 comprising the amino acid sequence of SEQ ID NO: 83; and (f) HVR-L3 comprising an amino acid sequence selected from SEQ ID NO: 84.

In any of the above embodiments, an anti-LgR5 antibody is a human antibody.

In another aspect, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 26. In certain embodiments, a VH sequence having at least 90%, 91%, 92%, 93%, 94%, 95%, 96%, 97%, 98%, or 99% identity to the amino acid sequence of SEQ ID NO: 51 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in SEQ ID NO: 51. In certain embodiments, a total of 1 to 5 amino acids have been substituted, inserted and/or deleted in SEQ ID NO: 51. In certain embodiments, substitutions, insertions, or deletions occur in regions outside the HVRs (i.e., in the FRs). Optionally, the anti-LgR5 antibody comprises the VH sequence of SEQ ID NO: 51, including post-translational modifications of that sequence. In a particular embodiment, the VH comprises one, two or three HVRs selected from: (a) HVR-H1 comprising the amino acid sequence of SEQ ID NO: 85, (b) HVR-H2 comprising the amino acid sequence of SEQ ID NO: 86, and (c) HVR-H3 comprising the amino acid sequence of SEQ ID NO: 87.

In another aspect, an anti-LgR5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 50. In certain embodiments, a VL sequence having at least 90%, 91%, 92%, 93%, 94%, 95%, 96%, 97%, 98%, or 99% identity to the amino acid sequence of SEQ ID NO: 50 contains substitutions (e.g., conservative substitutions), insertions, or deletions relative to the reference sequence, but an anti-LgR5 antibody comprising that sequence retains the ability to bind to LgR5. In certain embodiments, a total of 1 to 5 amino acids have been substituted, inserted and/or deleted in SEQ ID NO: 50. In certain embodiments, a total of 1 to 10 amino acids have been substituted, inserted and/or deleted in SEQ ID NO: 50. In certain embodiments, the substitutions, insertions, or deletions occur in regions outside the HVRs (i.e., in the FRs). Optionally, the anti-LgR5 antibody comprises the VL sequence of SEQ ID NO: 50, including post-translational modifications of that sequence. In a particular embodiment, the VL comprises one, two or three HVRs selected from (a) HVR-L1 comprising the amino acid sequence of SEQ ID NO: 82; (b) HVR-L2 comprising the amino acid sequence of SEQ ID NO: 83; and (c) HVR-L3 comprising the amino acid sequence of SEQ ID NO: 84.

In another aspect, an anti-LgR5 antibody is provided, wherein the antibody comprises a VH as in any of the embodiments provided above, and a VL as in any of the embodiments provided above. In one embodiment, the antibody comprises the VH and VL sequences in SEQ ID NO: 51 and SEQ ID NO: 50, respectively, including post-translational modifications of those sequences.

In a further aspect, the invention provides an antibody that binds to the same epitope as an anti-LgR5 antibody provided herein. For example, in certain embodiments, an antibody is provided that binds to the same epitope as an anti-LgR5 antibody comprising a VH sequence of SEQ ID NO: 51 and a VL sequence of SEQ ID NO: 50. In certain embodiments, an antibody is provided that binds to an epitope of SEQ ID NO: 21 from, within, or overlapping amino acids 22-123. In certain embodiments, an antibody is provided that binds to an epitope of SEQ ID NO: 22 from, within, or overlapping amino acids 1-102.

In a further aspect of the invention, an anti-LgR5 antibody according to any of the above embodiments is a monoclonal antibody, including a human antibody. In one embodiment, an anti-LgR5 antibody is an antibody fragment, e.g., a Fv, Fab, Fab', scFv, diabody, or F(ab')$_2$ fragment. In another embodiment, the antibody is a substantially full length antibody, e.g., an IgG2a antibody or other antibody class or isotype as defined herein.

In a further aspect, an anti-LgR5 antibody according to any of the above embodiments may incorporate any of the features, singly or in combination, as described in Sections 1-7 below.

Antibody 3G12 and Other Embodiments

In some embodiments, the invention provides an anti-LgR5 antibody comprising at least one, two, three, four, five, or six HVRs selected from (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72.

In another aspect, the invention provides an antibody comprising (a) HVR-H1 comprising the amino acid sequence of SEQ ID NO: 73; (b) HVR-H2 comprising the amino acid sequence of SEQ ID NO: 74; (c) HVR-H3 comprising the amino acid sequence of SEQ ID NO: 75; (d) HVR-L1 comprising the amino acid sequence of SEQ ID NO: 70; (e) HVR-L2 comprising the amino acid sequence of SEQ ID NO: 71; and (f) HVR-L3 comprising the amino acid sequence of SEQ ID NO: 72.

In any of the above embodiments, an anti-LgR5 antibody is humanized. In one embodiment, an anti-LgR5 antibody comprises HVRs as in any of the above embodiments, and further comprises a human acceptor framework, e.g. a human immunoglobulin framework or a human consensus framework. In certain embodiments, the human acceptor framework is the human VL kappa consensus ($VL_K$) framework and/or the human VH subgroup 3 consensus ($VH_3$) framework.

In another aspect, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 47. In certain embodiments, a VH sequence having at least 90%, 91%, 92%, 93%, 94%, 95%, 96%, 97%, 98%, or 99% identity to the amino acid sequence of SEQ ID NO: 47 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in the amino acid sequence of SEQ ID NO: 47. In certain embodiments, a total of 1 to 5 amino acids have been substituted, inserted and/or deleted in the amino acid sequence of SEQ ID NO: 47. In certain embodiments, substitutions, insertions, or deletions occur in regions outside the HVRs (i.e., in the FRs).

Optionally, the anti-LgR5 antibody comprises the VH sequence of SEQ ID NO: 47, including post-translational modifications of that sequence. In a particular embodiment, the VH comprises one, two or three HVRs selected from: (a) HVR-H1 comprising the amino acid sequence of SEQ ID NO: 73, (b) HVR-H2 comprising the amino acid sequence of SEQ ID NO: 74, and (c) HVR-H3 comprising the amino acid sequence of SEQ ID NO: 75.

In another aspect, an anti-LgR5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 46. In certain embodiments, a VL sequence having at least 90%, 91%, 92%, 93%, 94%, 95%, 96%, 97%, 98%, or 99% identity to the amino acid sequence of SEQ ID NO: 46 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in the amino acid sequence of SEQ ID NO: 46. In certain embodiments, a total of 1 to 5 amino acids have been substituted, inserted and/or deleted in the amino acid sequence of SEQ ID NO: 46. In certain embodiments, the substitutions, insertions, or deletions occur in regions outside the HVRs (i.e., in the FRs).

Optionally, the anti-LgR5 antibody comprises the VL sequence of SEQ ID NO: 46, including post-translational modifications of that sequence. In a particular embodiment, the VL comprises one, two or three HVRs selected from (a) HVR-L1 comprising the amino acid sequence of SEQ ID NO: 70; (b) HVR-L2 comprising the amino acid sequence of SEQ ID NO: 71; and (c) HVR-L3 comprising the amino acid sequence of SEQ ID NO: 72.

In another aspect, an anti-LgR5 antibody is provided, wherein the antibody comprises a VH as in any of the embodiments provided above, and a VL as in any of the embodiments provided above. In one embodiment, the antibody comprises the VH and VL sequences in SEQ ID NO: 47 and SEQ ID NO: 46, respectively, including post-translational modifications of those sequences.

In a further aspect, the invention provides an antibody that binds to the same epitope as an anti-LgR5 antibody provided herein. For example, in certain embodiments, an antibody is provided that binds to the same epitope as an anti-LgR5 antibody comprising a VH sequence of SEQ ID NO: 47 and a VL sequence of SEQ ID NO: 46. In certain embodiments, an antibody is provided that binds to an epitope of SEQ ID NO: 21 from, within, or overlapping amino acids 324-423. In some embodiments, an antibody is provided that binds to an epitope of SEQ ID NO: 22 from, within, or overlapping amino acids 303-402. In certain embodiments, an antibody is provided that binds to an epitope of SEQ ID NO: 21 from, within, or overlapping amino acids 324-555. In some embodiments, an antibody is provided that binds to an epitope of SEQ ID NO: 22 from, within, or overlapping amino acids 303-534.

In a further aspect of the invention, an anti-LgR5 antibody according to any of the above embodiments is a monoclonal antibody, including a chimeric, humanized or human antibody. In one embodiment, an anti-LgR5 antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In a further aspect, an anti-LgR5 antibody according to any of the above embodiments may incorporate any of the features, singly or in combination, as described in Sections 1-7 below.

Antibody 2H6 and Other Embodiments

In some embodiments, the invention provides an anti-LgR5 antibody comprising at least one, two, three, four, five, or six HVRs selected from (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78.

In another aspect, the invention provides an antibody comprising (a) HVR-H1 comprising the amino acid sequence of SEQ ID NO: 79; (b) HVR-H2 comprising the amino acid sequence of SEQ ID NO: 80; (c) HVR-H3 comprising the amino acid sequence of SEQ ID NO: 81; (d) HVR-L1 comprising the amino acid sequence of SEQ ID NO: 76; (e) HVR-L2 comprising the amino acid sequence of SEQ ID NO: 77; and (f) HVR-L3 comprising the amino acid sequence of SEQ ID NO: 78.

In any of the above embodiments, an anti-LgR5 antibody is humanized. In one embodiment, an anti-LgR5 antibody comprises HVRs as in any of the above embodiments, and further comprises a human acceptor framework, e.g. a human immunoglobulin framework or a human consensus framework. In certain embodiments, the human acceptor framework is the human VL kappa consensus ($VL_K$) framework and/or the human VH subgroup 3 ($VH_3$) framework.

In another aspect, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 49. In certain embodiments, a VH sequence having at least 90%, 91%, 92%, 93%, 94%, 95%, 96%, 97%, 98%, or 99% identity to the amino acid sequence of SEQ ID NO: 49 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in the amino acid sequence of SEQ ID NO: 49. In certain embodiments, a total of 1 to 5 amino acids have been substituted, inserted and/or deleted in the amino acid sequence of SEQ ID NO: 49. In certain embodiments, substitutions, insertions, or deletions occur in regions outside the HVRs (i.e., in the FRs).

Optionally, the anti-LgR5 antibody comprises the VH sequence of SEQ ID NO: 49, including post-translational modifications of that sequence. In a particular embodiment, the VH comprises one, two or three HVRs selected from: (a) HVR-H1 comprising the amino acid sequence of SEQ ID NO: 79, (b) HVR-H2 comprising the amino acid sequence of SEQ ID NO: 80, and (c) HVR-H3 comprising the amino acid sequence of SEQ ID NO: 81.

In another aspect, an anti-LgR5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 48. In certain embodiments, a VL sequence having at least 90%, 91%, 92%, 93%, 94%, 95%, 96%, 97%, 98%, or 99% identity to the amino acid sequence of SEQ ID NO: 48 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in the amino acid sequence of SEQ ID NO: 48. In certain embodiments, a total of 1 to 5 amino acids have been substituted, inserted and/or deleted in the amino acid sequence of SEQ ID NO: 48. In certain embodiments, the substitutions, insertions, or deletions occur in regions outside the HVRs (i.e., in the FRs).

Optionally, the anti-LgR5 antibody comprises the VL sequence of the amino acid sequence of SEQ ID NO: 48, including post-translational modifications of that sequence. In a particular embodiment, the VL comprises one, two or three HVRs selected from (a) HVR-L1 comprising the amino acid sequence of SEQ ID NO: 76; (b) HVR-L2 comprising the amino acid sequence of SEQ ID NO: 77; and (c) HVR-L3 comprising the amino acid sequence of SEQ ID NO: 78.

In another aspect, an anti-LgR5 antibody is provided, wherein the antibody comprises a VH as in any of the embodiments provided above, and a VL as in any of the embodiments provided above. In one embodiment, the antibody comprises the VH and VL sequences in SEQ ID NO: 49 and SEQ ID NO: 48, respectively, including post-translational modifications of those sequences.

In a further aspect, the invention provides an antibody that binds to the same epitope as an anti-LgR5 antibody provided herein. For example, in certain embodiments, an antibody is provided that binds to the same epitope as an anti-LgR5 antibody comprising a VH sequence of SEQ ID NO: 49 and a VL sequence of SEQ ID NO: 48. In certain embodiments, an antibody is provided that binds to an epitope of SEQ ID NO: 21 from, within, or overlapping amino acids 324-423. In some embodiments, an antibody is provided that binds to an epitope of SEQ ID NO: 22 from, within, or overlapping amino acids 303-402. In certain embodiments, an antibody is provided that binds to an epitope of SEQ ID NO: 21 from, within, or overlapping amino acids 324-555. In some embodiments, an antibody is provided that binds to an epitope of SEQ ID NO: 22 from, within, or overlapping amino acids 303-534.

In a further aspect of the invention, an anti-LgR5 antibody according to any of the above embodiments is a monoclonal antibody, including a chimeric, humanized or human antibody. In one embodiment, an anti-LgR5 antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In a further aspect, an anti-LgR5 antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

In some embodiments, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for LgR5 and the other is for any other antigen. In certain embodiments, bispecific antibodies may bind to two different epitopes of LgR5. Bispecific antibodies may also be used to localize cytotoxic agents to cells which express LgR5. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to LgR5 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, an antibody variant possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166: 1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.*

24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-LgR5 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-LgR5 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-LgR5 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-LgR5 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, FACS or Western blot.

In another aspect, competition assays may be used to identify an antibody that competes with any of the antibodies described herein for binding to LgR5. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized LgR5 is incubated in a solution comprising a first labeled antibody that binds to LgR5 (e.g., any of the antibodies described herein) and a second unlabeled antibody that is being tested for its ability to compete with the first antibody for binding to LgR5. The second antibody may be present in a hybridoma supernatant. As a control, immobilized LgR5 is incubated in a solution comprising the first labeled antibody but not the second unlabeled antibody. After incubation under conditions permissive for binding of the first antibody to LgR5, excess unbound antibody is removed, and the amount of label associated with immobilized LgR5 is measured. If the amount of label associated with immobilized LgR5 is substantially reduced in the test sample relative to the control sample, then that indicates that the second antibody is competing with the first antibody for binding to LgR5. See Harlow and Lane (1988) *Antibodies: A Laboratory Manual* ch. 14 (Cold Spring Harbor Laboratory, Cold Spring Harbor, N.Y.).

D. Immunoconjugates

The invention also provides immunoconjugates comprising an anti-LgR5 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity.

E. Methods and Compositions for Diagnostics and Detection

In certain embodiments, any of the anti-LgR5 antibodies provided herein is useful for detecting the presence of LgR5 in a biological sample. The term "detecting" as used herein encompasses quantitative or qualitative detection. A "biological sample" comprises, e.g., a cell or tissue (e.g., biopsy material, including cancerous or potentially cancerous colon, colorectal, small intestine, endometrial, pancreatic, or ovarian tissue).

In one embodiment, an anti-LgR5 antibody for use in a method of diagnosis or detection is provided. In a further aspect, a method of detecting the presence of LgR5 in a biological sample is provided. In certain embodiments, the method comprises contacting the biological sample with an anti-LgR5 antibody as described herein under conditions permissive for binding of the anti-LgR5 antibody to LgR5, and detecting whether a complex is formed between the anti-LgR5 antibody and LgR5 in the biological sample. Such method may be an in vitro or in vivo method. In one embodiment, an anti-LgR5 antibody is used to select subjects eligible for therapy with an anti-LgR5 antibody, e.g. where LgR5 is a biomarker for selection of patients. In a further embodiment, the biological sample is a cell or tissue (e.g., biopsy material, including cancerous or potentially cancerous colon, colorectal, small intestine, endometrial, pancreatic, or ovarian tissue).

In a further embodiment, an anti-LgR5 antibody is used in vivo to detect, e.g., by in vivo imaging, an LgR5-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting an LgR5-positive cancer in a subject, the method comprising administering a labeled anti-LgR5 antibody to a subject having or suspected of having an LgR5-positive cancer, and detecting the labeled anti-LgR5 antibody in the subject, wherein detection of the labeled anti-LgR5 antibody indicates an LgR5-positive cancer in the subject. In certain of such embodiments, the labeled anti-LgR5 antibody comprises an anti-LgR5 antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr. Nonlimiting exemplary methods of making and using $^{89}$Zr-labeled antibodies are described, e.g., in PCT Publication No. WO 2011/056983. In some embodiments, the labeled anti-LgR5 antibody is a cysteine engineered antibody conjugated to one or more zirconium complexes. See, e.g., WO 2011/056983.

In further embodiments, a method of diagnosis or detection comprises contacting a first anti-LgR5 antibody immobilized to a substrate with a biological sample to be tested for the presence of LgR5, exposing the substrate to a second anti-LgR5 antibody, and detecting whether the second anti-LgR5 is bound to a complex between the first anti-LgR5 antibody and LgR5 in the biological sample. A substrate may be any supportive medium, e.g., glass, metal, ceramic, polymeric beads, slides, chips, and other substrates. In certain embodiments, a biological sample comprises a cell or tissue (e.g., biopsy material, including cancerous or potentially cancerous colon, colorectal, small intestine, endometrial, pancreatic or ovarian tissue). In certain embodiments, the first or second anti-LgR5 antibody is any of the antibodies described herein. In such embodiments, the second anti-LgR5 antibody may be αLgR5.1-12 or antibodies derived from αLgR5.1-12 as described herein. In such embodiments, the second anti-LgR5 antibody may be αLgR5.26-1 or antibodies derived from αLgR5.26-1 as described herein.

Exemplary disorders that may be diagnosed or detected according to any of the above embodiments include LgR5-positive cancers, such as LgR5-positive colorectal cancer (including adenocarcinoma), LgR5-positive small intestine cancer (including adenocarcinoma, sarcoma (e.g., leiomyosarcoma), carcinoid tumors, gastrointestinal stromal tumor, and lymphoma) LgR5-positive ovarian cancer (including ovarian serous adenocarcinoma), LgR5-positive pancreatic cancer (including pancreatic ductal adenocarcinoma), and LgR5-positive endometrial cancer.

In some embodiments, an LgR5-positive cancer is a cancer that receives a LgR5 immunohistochemistry (IHC) score greater than "0," which corresponds to very weak or no staining, under the conditions described herein in the Examples (see, e.g., Examples F, H, and I). In another embodiment, a LgR5-positive cancer expresses LgR5 at a 1+, 2+ or 3+ level, as defined under the conditions described herein in the Examples (see, e.g., Examples F, H, and I). In some embodiments, one or more cell lines may be used as a control for staining level. For example, in some embodiments, a cell line shown in Table 4 in Example I may be used as a control for staining level. For example, in some embodiments, cell line SW480, RKO, COLO741, HCT-15, CX-1, HT-29, SW1116, HCA-7, and/or COLO-205 may be used as a control for 0 staining; cell line SW948, CACO-2, and/or C2BBel may be used as a control for 1+ staining; and/or cell line T84, SW1463, SK-CO-1, and/or LOVO may be used as a control for 2+ staining. In some embodiments, an LgR5-positive cancer is a cancer that receives an H score of 50 or greater, as defined under the conditions described herein in Example H (corresponding to an overall score of 1+, 2+ or 3+ using 50%+ criteria). In some embodiments, a LgR5-positive cancer is a cancer that receives an H score of 10 or greater, as defined under the conditions described herein in Example H (corresponding to an overall score of 1+, 2+, or 3+ using 10%+ criteria).

In some embodiments, an LgR5-positive cancer is a cancer that expresses LgR5 according to a reverse-transcriptase PCR (RT-PCR) assay that detects LgR5 mRNA. In some embodiments, the RT-PCR is quantitative RT-PCR.

In certain embodiments, labeled anti-LgR5 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-LgR5 antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other. For example, in some instances, it may be desirable to further provide Avastin® (bevacizumab), e.g., for the treatment of LgR5-positive cancer such as LgR5-positive colon cancer or LgR5-positive colorectal cancer.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-LgR5 antibodies or immunoconjugates provided herein may be used in methods, e.g., therapeutic methods.

In one aspect, an anti-LgR5 antibody or immunoconjugate provided herein is used in a method of inhibiting proliferation of a LgR5-positive cell, the method comprising exposing the cell to the anti-LgR5 antibody or immunoconjugate under conditions permissive for binding of the anti-LgR5 antibody or immunoconjugate to LgR5 on the surface of the cell, thereby inhibiting the proliferation of the cell. In certain embodiments, the method is an in vitro or an in vivo method. In further embodiments, the cell is a colon, colorectal, small intestine, ovarian, pancreatic, or endometrial cell.

In some embodiments, an anti-LgR5 antibody or immunoconjugate provided herein is used in a method of treating cancer that comprises a mutation in a Kras gene and/or a mutation in an adenomatous polyposis coli (APC) gene in at least a portion of the cells of the cancer. In various embodiments, the cancer is selected from colon, colorectal, small intestine, ovarian, pancreatic, and endometrial cancer. In some embodiments, an anti-LgR5 antibody or immunoconjugate provided herein is used in a method of treating a colon or colorectal cancer that comprises a mutation in a Kras gene and/or a mutation in an APC gene in at least a portion of the cells of the cancer. Nonlimiting exemplary Kras mutations found in cancers (including colon and colorectal cancers) include mutations at Kras codon 12 (e.g., G12D, G12V, G12R, G12C, G12S, and G12A), codon 13 (e.g., G13D and G13C), codon 61 (e.g., G61H, G61L, G61E, and G61K), and codon 146. See, e.g., Yokota, *Anticancer Agents Med. Chem.*, 12: 163-171 (2012); Wicki et al., *Swiss Med. Wkly*, 140: w13112 (2010). Nonlimiting exemplary APC mutations found in cancers include mutations in the mutation cluster region (MCR), such as stop codons and frameshift mutations that result in a truncated APC gene product. See, e.g., Chandra et al., *PLoS One*, 7: e34479 (2012); and Kohler et al., *Hum. Mol. Genet.*, 17: 1978-1987 (2008).

In some embodiments, a method of treating cancer comprises administering an anti-LgR5 antibody or immunoconjugate to a subject, wherein the subject has a cancer comprising a Kras mutation and/or an APC mutation in at least a portion of the cancer cells. In some embodiments, the cancer is selected from colon, colorectal, small intestine, ovarian, pancreatic, and endometrial cancer. In some embodiments, the cancer is colon and/or colorectal cancer. In some embodiments, the subject has previously been determined to have a cancer comprising a Kras mutation and/or an APC mutation in at least a portion of the cancer cells. In some embodiments, the cancer is LgR5-positive.

Presence of various biomarkers in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like, RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602,677. The assay may be conducted in 96- or 384-well format, making it amenable to automated high-throughput screening (HTS). See Cree et al. (1995) *AntiCancer Drugs* 6:398-404.

The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-LgR5 antibody or immunoconjugate for use as a medicament is provided. In further aspects, an anti-LgR5 antibody or immunoconjugate for use in a method of treatment is provided. In certain embodiments, an anti-LgR5 antibody or immunoconjugate for use in treating LgR5-positive cancer is provided. In certain embodiments, the invention provides an anti-LgR5 antibody or immunoconjugate for use in a method of treating an individual having a LgR5-positive cancer, the method comprising administering to the individual an effective amount of the anti-LgR5 antibody or immunoconjugate. In one such embodiment, the method further comprises administering to the individual an effective amount of at least one additional therapeutic agent, e.g., as described below.

In a further aspect, the invention provides for the use of an anti-LgR5 antibody or immunoconjugate in the manufacture or preparation of a medicament. In one embodiment, the medicament is for treatment of LgR5-positive cancer. In a further embodiment, the medicament is for use in a method of treating LgR5-positive cancer, the method comprising administering to an individual having LgR5-positive cancer an effective amount of the medicament. In one such embodiment, the method further comprises administering to the individual an effective amount of at least one additional therapeutic agent, e.g., as described below.

In a further aspect, the invention provides a method for treating LgR5-positive cancer. In one embodiment, the method comprises administering to an individual having such LgR5-positive cancer an effective amount of an anti-LgR5 antibody or immunoconjugate. In one such embodiment, the method further comprises administering to the individual an effective amount of at least one additional therapeutic agent, as described below.

An LgR5-positive cancer according to any of the above embodiments may be, e.g., LgR5-positive colon or colorectal cancer (including adenocarcinoma), LgR5-positive small intestine cancer (including adenocarcinoma, sarcoma (e.g., leiomyosarcoma), carcinoid tumors, gastrointestinal stromal tumor, and lymphoma), LgR5-positive ovarian cancer (including ovarian serous adenocarcinoma), LgR5-positive pancreatic cancer (including pancreatic ductal adenocarcinoma), and LgR5-positive endometrial cancer.

In some embodiments, an LgR5-positive cancer is a cancer that receives a LgR5 immunohistochemistry (IHC) score greater than "0," which corresponds to very weak or no staining, under the conditions described herein in the Examples (see, e.g., Examples F, H, and I). In another embodiment, a LgR5-positive cancer expresses LgR5 at a 1+, 2+ or 3+ level, as defined under the conditions described herein in the Examples (see, e.g., Examples F, H, and I). In some embodiments, one or more cell lines may be used as a control for staining level. For example, in some embodiments, a cell line shown in Table 4 in Example I may be used as a control for staining level. For example, in some embodiments, cell line SW480, RKO, COLO741, HCT-15, CX-1, HT-29, SW1116, HCA-7, and/or COLO-205 may be used as a control for 0 staining; cell line SW948, CACO-2, and/or C2BBel may be used as a control for 1+ staining; and/or cell line T84, SW1463, SK-CO-1, and/or LOVO may be used as a control for 2+ staining. In some embodiments, an LgR5-positive cancer is a cancer that receives an H score of 50 or greater, as defined under the conditions described herein in Example H (corresponding to an overall score of 1+, 2+ or 3+ using 50%+ criteria). In some embodiments, a LgR5-positive cancer is a cancer that receives an H score of 10 or greater, as defined under the conditions described herein in Example H (corresponding to an overall score of 1+, 2+, or 3+ using 10%+ criteria).

In some embodiments, an LgR5-positive cancer is a cancer that expresses LgR5 according to a reverse-transcriptase PCR (RT-PCR) assay that detects LgR5 mRNA. In some embodiments, the RT-PCR is quantitative RT-PCR.

An "individual" according to any of the above embodiments may be a human.

In a further aspect, the invention provides pharmaceutical formulations comprising any of the anti-LgR5 antibodies or immunoconjugate provided herein, e.g., for use in any of the above therapeutic methods. In one embodiment, a pharmaceutical formulation comprises any of the anti-LgR5 antibodies or immunoconjugates provided herein and a pharmaceutically acceptable carrier. In another embodiment, a pharmaceutical formulation comprises any of the anti-LgR5 antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent. In certain embodiments, an additional therapeutic agent is Avastin® (bevacizumab), e.g., for the treatment of LgR5-positive cancer such as LgR5-positive colon cancer or LgR5-positive colorectal cancer.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 μg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate and an anti-LgR5 antibody.

H. Articles of Manufacture

In another aspect, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an anti-LgR5 antibody or immunoconjugate. The label or package insert indicates that the composition is used for treating the condition of choice. Moreover, the article of manufacture may comprise (a) a first container with a composition contained therein, wherein the composition comprises an antibody or immunoconjugate; and (b) a second container with a composition contained therein, wherein the composition comprises a further cytotoxic or otherwise therapeutic agent. The article of manufacture in this embodiment may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

A. Human LgR5 Gene Expression

Human LgR5 gene expression was analyzed using a proprietary database containing gene expression information (GeneExpress®, Gene Logic Inc., Gaithersburg, Md.). Graphical analysis of the GeneExpress® database was conducted using a microarray profile viewer. FIG. 1 is a graphic representation of human LgR5 gene expression in various tissues. The scale on the y-axis indicates gene expression levels based on hybridization signal intensity. Dots appear both to the left and to the right of the line extending from the name of each listed tissue. The dots appearing to the left of the line represent gene expression in normal tissue, and the dots appearing to the right of the line represent gene expression in tumor and diseased tissue. FIG. 1 shows increased LgR5 gene expression in certain tumor or diseased tissues relative to their normal counterparts. In particular, LgR5 is substantially overexpressed in colorectal, endometrial, and ovarian tumors. FIG. 1, inset, shows that LgR5 is overexpressed in at least the following colon tumors: adenocarcinoma, benign tumors, and metastatic colon tumors, and also in tissue with a colon tumor content of less than 50% ("low tumor" in FIG. 1 inset); but is not overexpressed in normal colon, Crohn's disease, or ulcerative colitis. Human LgR5 expression is much lower in normal tissues, with low levels of expression in normal brain, muscle, ovarian, and placental tissues.

B. Prevalence of Human LgR5 in Colon Tumors

To evaluate the expression of LgR5 in colorectal cancer, 57 primary colorectal adenocarcinomas were acquired from multiple sources (Asterand, Detroit, Mich.; Bio-Options, Fullerton, Calif.; University of Michigan, Ann Arbor, Mich.; Cytomyx, Rockville, Md.; Cooperative Human Tissue Network, Nashville, Tenn.; Indivumed, Hamburg, Germany; ProteoGenex, Culver City, Calif.). Forty-four percent of samples were from men, and the average age of the patients was 66 years (range 31 to 93 years). Tissue microarrays (TMAs) were assembled using duplicate cores as described in Bubendorf L, et al., *J Pathol.* 2001 September; 195(1): 72-9, and included five normal colorectal mucosa samples from matched cases.

LgR5 expression was determined by in situ hybridization using the oligonucleotide probes shown in Table 2. See, e.g., Jubb A M, et al., *Methods Mol Biol* 2006; 326:255-64. ISH for β-actin was used to confirm mRNA integrity in colorectal cancer tissues prior to analysis.

TABLE 2

Primer sequences for isotopic in situ hybridization probes.

| Gene | Genbank Accession | Nucleotides Complementary to Probe | Antisense (AS) or Sense (S) | Forward Primer (5' to 3') | Reverse Primer (5' to 3') |
|---|---|---|---|---|---|
| Lgr5 | NM_003667 | 508 | AS | ACCAACT GCATCCT AAACTG (SEQ ID NO: 92) | ACCGAGT TTCACCT CAGCTC (SEQ ID NO: 93) |
| Lgr5 | NM_003667 | 496 | S | ACATTGC CCTGTTG CTCTTC (SEQ ID NO: 94) | ACTGCTC TGATATA CTCAATC (SEQ ID NO: 95) |

LgR5 hybridization intensity was scored by a trained pathologist according to the scheme below, taking into account the intensity (silver grains) as well as breadth of staining
  0 (negative): very weak or no hybridization in >90% of tumor cells
  1+ (mild): predominant hybridization pattern is weak
  2+ (moderate): predominant hybridization pattern is moderately strong in the majority (>50%) of neoplastic cells
  3+ (strong): predominant hybridization pattern is strong in the majority (>50%) of neoplastic cells
Sense probes were used to control for the specificity of hybridization.

Figure 2:
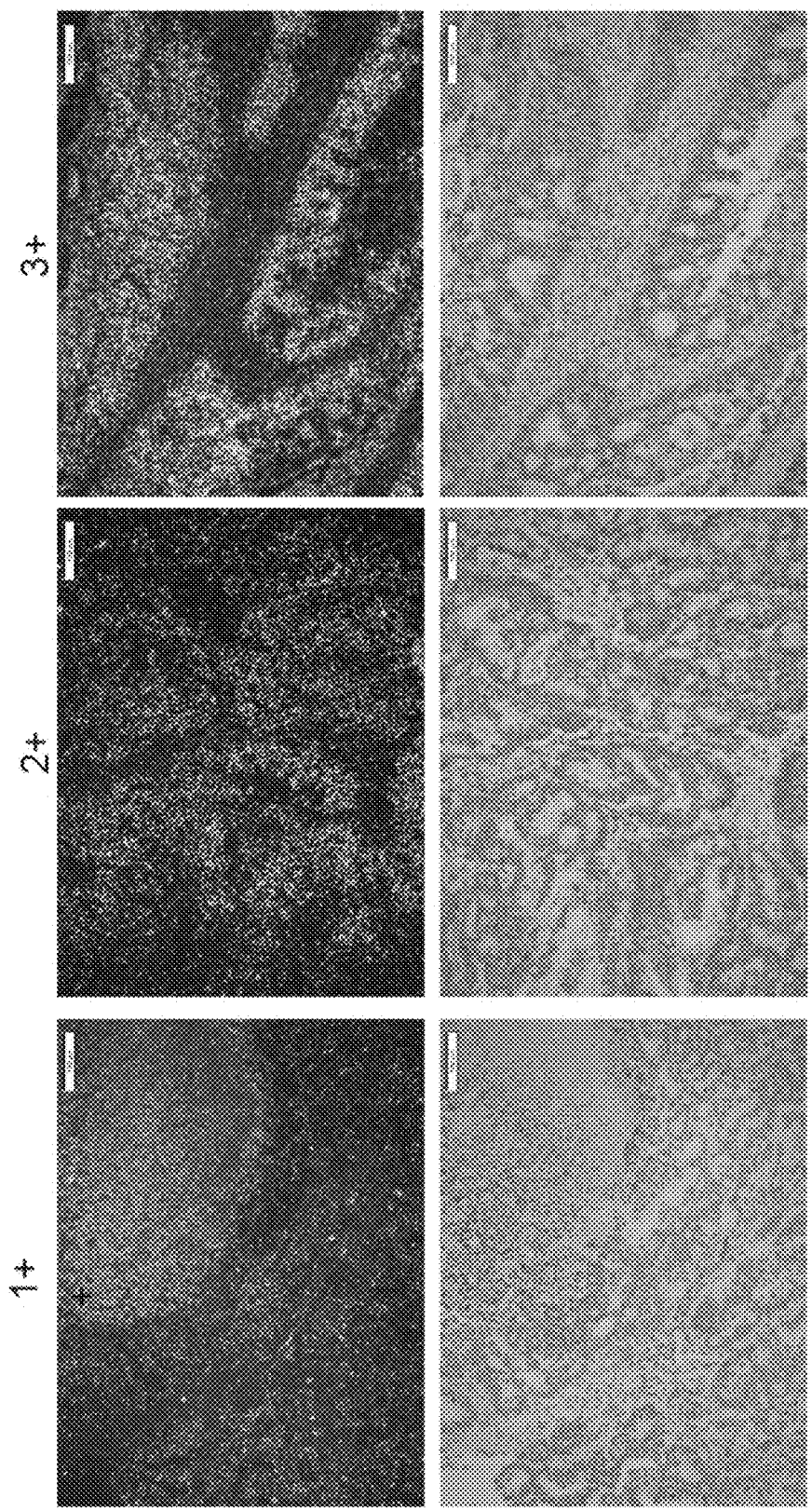
FIG. 2 shows expression of LgR5 in colon tumors by in situ hybridization, as described in Example B.

FIG. 2 shows exemplary colon tumor sections with 1+, 2+, and 3+ levels of staining. The top panels show dark field images and the bottom panels show bright field images. The deposition of silver grains in the dark field images indicates hybridization of the probe and expression of LgR5 mRNA. ~77% ($^{41}/_{53}$) of colon tumor sections analyzed were LgR5 positive, showing staining at the 1+, 2+, or 3+ levels, with 34% ($^{18}/_{53}$) showing 2+ or 3+ staining. Four of the 57 samples analyzed were noninformative for LgR5 expression.

To evaluate the significance of Lgr5 expression in colon tumors, a population-based series of patients who had undergone surgical resections for colorectal adenocarcinoma was compiled retrospectively from the pathology archives at St James' University Hospital (Leeds, UK) from 1988 to 2003. Tissue microarrays (TMAs) were constructed with one core of normal mucosa and three cores of adenocarcinoma per patient as described in Bubendorf L, et al., *J Pathol.* 2001 September; 195(1):72-9. ISH was performed and scored as described above. The heterogeneity of expression across three cores from the same tumor was also determined, and is expressed as the proportion of tumors that showed a particular level of discordance in one of the three cores. For example, if three cores had scores of +1, +3, and +3, one of the three cores from that tumor is discordant by 2.

Figure 3A:
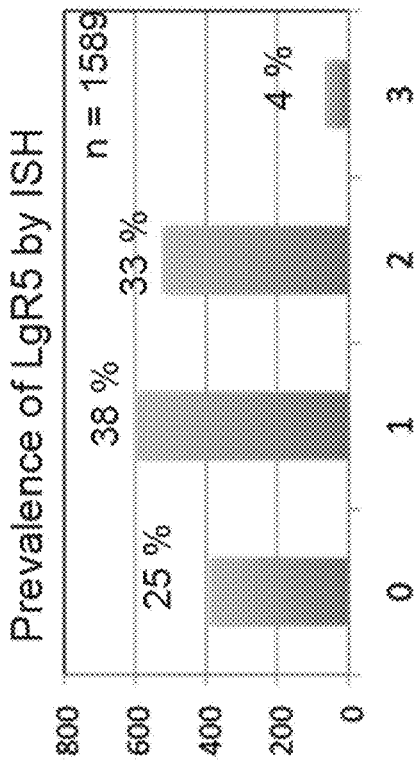
FIGS. 3A and 3B show (A) the prevalence of various levels of LgR5 expression in a colon tumor tissue microarray, and (B) the heterogeneity of LgR5 expression in three cores from each colorectal adenocarcinoma sample, both determined by in situ hybridization, as described in Example B.
Figure 3B:
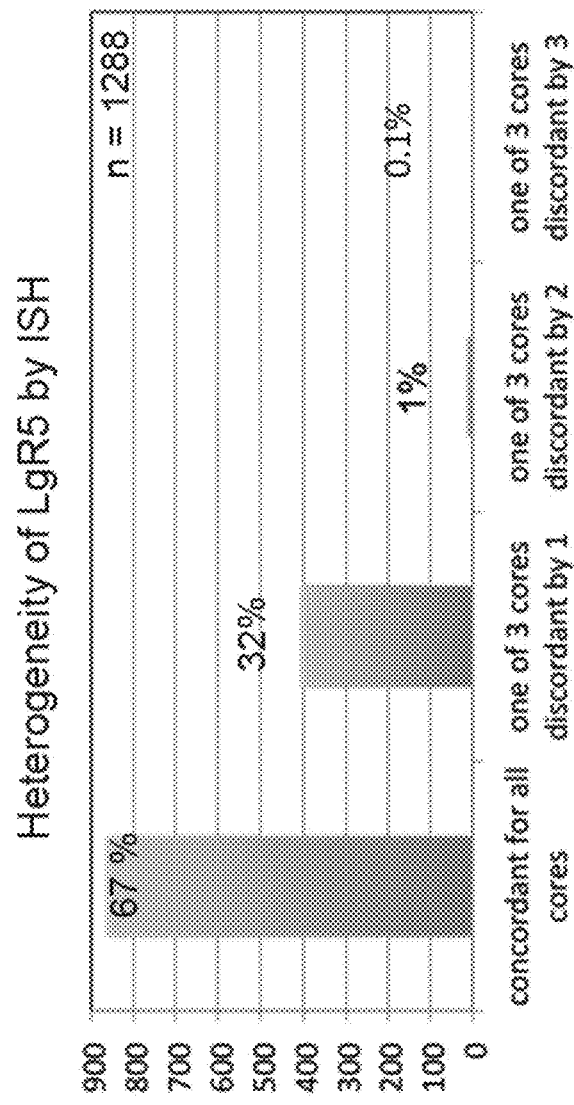

FIG. 3A shows the prevalence of 0, 1+, 2+, and 3+ levels of LgR5 staining in the colon tumor tissue microarray, measured by in situ hybridization. 75% of the colon tumor tissues showed staining at the 1+, 2+, or 3+ levels, with 37% showing 2+ or 3+ staining. FIG. 3B shows the heterogeneity of LgR5 expression. 67% of tumors showed no heterogeneity across the three cores. 32% shows a discordance of 1 in one of the three cores, and only 1% showed a discordance greater than 1.

C. Commercially Available Antibodies not Suitable for Immunohistochemistry

A long-standing issue in determining the expression of Lgr5 was the lack of a quality Immunohistochemistry (IHC) reactive antibody. RNA expression of Lgr5 has been limitedly examined previously; however, there is little data about the normal tissue expression pattern in humans outside of the stomach, colon, and hair follicle.

Six different commercial antibodies that are marketed as IHC antibodies were tested for suitability as antibodies for immunohistochemistry. Rabbit polyclonal antibody MC-1235 (MBL International Corp., Woburn, Mass.) was tested for binding to LgR5 expressed on the surface of 293 cells, and no LgR5 detection was observed. Rabbit polyclonal antibody MC-1236 (MBL International Corp., Woburn, Mass.) was able to stain LgR5 when it was overexpressed on 293 cells, but no specific LgR5 staining was observed on LoVo colon cancer cells, compared to 293 cells transfected with vector only. Further, brain tissue stained with MC-1236 showed a high level of staining within blood vessels, suggesting possible background staining of serum.

Rabbit monoclonal antibody 2495-1 (Epitomics, Burlingame, Calif.) was found to specifically stain LgR5 expressed on the surface of 293 cells. LoVo and D5124 colon cancer cells showed weak cytoplasmic staining, and some SW116 colon cancer cells showed very weak staining Human colon and small intestine tissues showed weak staining in the epithelial compartment, characterized as broadly diffuse cytoplasmic staining throughout the intestinal crypt. No specific staining in the basal portion of the crypt was noted, however, and no membrane-specific staining was observed in any of the cell lines or tissues tested.

Three additional commercial antibodies were tested for specific LgR5 staining: rabbit polyclonal antibody HPA012530 (Sigma-Aldrich, St. Louis, Mo.), rabbit monoclonal antibody LS-C105455 (LifeSpan BioSciences, Inc., Seattle, Wash.), and mouse monoclonal antibody TA503316 (OriGene, Rockville, Md.). None of the antibodies showed specific membranous staining of normal human small intestine and/or colon tissue samples, nor was LgR5 detected in the crypt base in those tissues.

D. Rabbit Monoclonal Antibody Generation

After several failed attempts to develop IHC reactive antibodies in mice, we generated an IHC reactive antibody in rabbits. Rabbits were immunized with an LgR5 extracellular domain (ECD) huFc (SEQ ID NO: 96) fusion protein, which was produced in CHO cells. Serum titers against LgR5 using test bleeds were evaluated using standard protocols. Two rabbits were found to have a good immune response, and were chosen as the candidate for splenectomy and monoclonal fusion.

Splenectomies were performed, splenocytes were isolated, and $200 \times 10^6$ lymphocyte cells were fused with $100 \times 10^6$ fusion partner cells and plated onto 96-well plates (Epitomics, Burlingame, Calif.). The plates were cultured under standard conditions.

Plates were screened using a standard ELISA protocol, with plates coated with LgR5 extracellular domain (ECD)-huFc fusion. Three clones were selected and expanded into 24-well plates. Thirty-six of the expanded clones were tested by ELISA and immunohistochemistry (IHC) using 293 cells expressing human or mouse LgR5.

After further testing, including determining whether the clones produced antibodies that recognized LgR5 on human intestine crypt base columnar cells, antibodies 1-12 and 26-1 were selected for cloning. Briefly, mRNA from hybridoma cells was isolated using TuboCapture Kit (Qiagen: Catalog

Figure 4A:
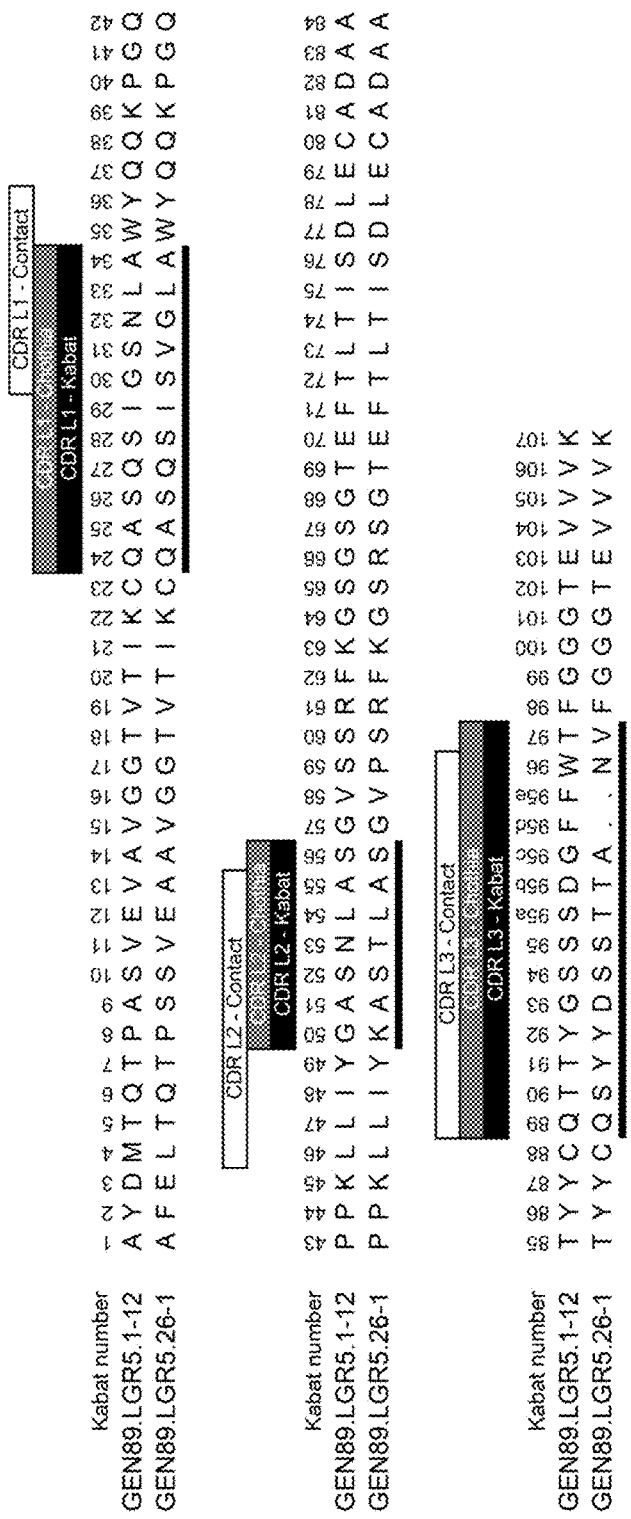

72232) following the manufacturer's instructions and then reverse transcribed into cDNA using oligo-dT primer. The variable region of the heavy chain (VH) was PCR amplified. The entire light chain (LC) was PCR. The PCR-amplified VH region was digested using restriction enzymes HindIII and Kpnl. The PCR-amplified LC was digested using restriction enzymes HindIII and NotI. Digested products were purified using Qiagen QIAquick PCR Purification Kit (catalog #28014). After purification, the VH and LC were ligated into heavy or light chain expression vectors and transformed into DH5α cells (MC Lab, catalog #DA-100). Transformed colonies were picked and inserts were confirmed by expected size using the corresponding restriction enzymes. Plasmids with inserts of the expected size were sequenced using TT5 primer. The sequences of the heavy chain variable region and the light chain variable region are shown in FIG. 4, and in SEQ ID NOs: 6 and 5, respectively, for antibody 1-12; and in FIG. 4, and in SEQ ID NOs: 8 and 7, respectively, for antibody 26-1.

Light chain and heavy chain expression vectors were co-transfected into CHO cells and purified from the cell culture supernatants using Protein A.

E. Antibody Epitope Determination

A FACS competition assay was used to map the epitopes recognized by antibodies 1-12 and 26-1. Briefly, human LgR5 was expressed in 293 cells and competition assays were performed using antibody huYW353 (heavy chain and light chain sequences shown in SEQ ID NOs: 90 and 91, respectively), which has previously been shown to bind to an epitope on LgR5 comprising amino acids 22 to 122, and antibody 8E11 (heavy and light chain variable regions shown in SEQ ID NOs: 29 and 28, respectively), which has previously been shown to bind to an epitope on LgR5 comprising amino acids 22 to 322.

Antibody 26-1 was found to compete for LgR5 binding with huYW353 and 8E11, while antibodies 1-12 did not compete for LgR5 binding with either huYW353 or 8E11. (Data not shown.) Thus, it appears that antibody 26-1 binds an epitope in the region of amino acids 22 to 322 of human LgR5, while antibody 1-12 binds an epitope outside of that region.

F. Detection of LgR5 on Normal Tissues

Antibody LGR5.1-12 was used to detect expression of LgR5 on normal human tissues Immunohistochemistry (IHC) for Lgr5 was performed on a Dako Universal Autostainer (Dako, Carpinteria, Calif.). Briefly, formalin-fixed, paraffin-embedded whole tissue and tissue microarray sections were deparaffinized and antigen unmasking was performed in a PT Module (Thermo Scientific, Kalamazoo, Mich.) with Target Retrieval pH 6 (Dako) at 99° C. for 20 minutes. Endogenous peroxidase was inhibited with treatment of 3% $H_2O_2$ in PBS for 4 minutes and endogenous biotin was blocked using the Avidin/Biotin blocking kit (Vector Labs, Burlingame, Calif.). Endogenous IgGs were blocked using 10% donkey serum in 3% BSA/PBS and primary antibody to Lgr5 (LGR5.1-12) was incubated at 4 µg/ml for 60 minutes at room temperature. Biotinylated donkey anti-rabbit IgG (Jackson Immunoresearch, West Grove, Pa.) was incubated for 30 minutes at room temperature followed by treatment with Vectastain ABC Elite-HRP (Vector Labs) for 30 minutes at room temperature. Antibody binding was detected with Metal enhanced DAB (Pierce Rockford, Ill.) for 5 minutes at room temperature and sections were counterstained with Mayer's Hematoxylin (Rowley Biochemical, Danvers, Mass.).

Figure 5A:
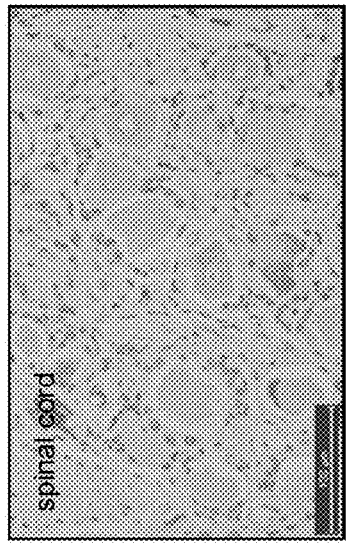
FIGS. 5A, 5B, and 5C show staining of (A) colon tissue, (B) hair follicle, and (C) spinal cord with antibody LGR5.1-12, as described in Example E.
Figure 5B:
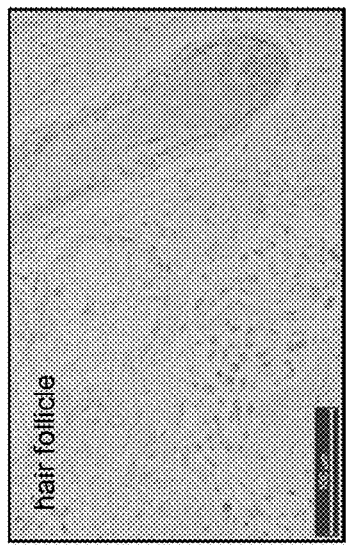
Figure 5C:
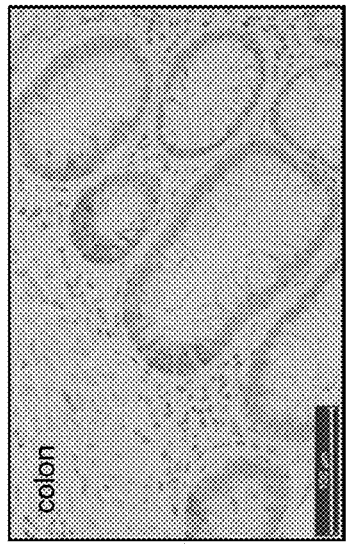

Antibody LGR5.1-12 stained normal intestinal crypts in the expected pattern. See FIG. 5A. Moderate staining was also observed in hair follicle (FIG. 5B), and weak staining was observed in fallopian tube, endometrium, adrenal gland, and spinal cord (FIG. 5C).

G. Detection of LgR5 on Xenograft Tumors

Tumors isolated from LoVo X 1.1 and D5124 xenograft model mice were analyzed by flow cytometry to determine surface expression of LgR5 using antibody YW353. Briefly, Lovo1.1 or D5124 tumors were harvested and treated with 1% bovine serum albumin (BSA) in phosphate-buffered saline (PBS) with a collagenase enzyme mixture. Tumors were incubated for 15 minutes at 37° C., and cells were washed in PBS with 1% BSA. Cells were spun down and resuspended in ammonium chloride-potassium lysis buffer to lyse the red blood cells. Cells were washed in PBS with 1% BSA and RRMI 1640 media with 10% fetal bovin serum (FBS). Cells were resuspended in fluorescence-activated cell sorting buffer (PBS with 1% BSA) and incubated for 45 minutes with anti-LgR5 antibody, followed by a 30 minute incubation with anti human secondary antibody conjugated to PE. Analysis was performed with a FACSCalibur™ flow cytometer (BD Biosciences).

FIG. 6 shows the results of that experiment. LgR5 on the surface of (A) LoVo X 1.1 xenograft tumor cells and (B) D5124 xenograft tumor cells was detectable by FACS using antibody YW353. By immunohistochemistry, expression of LgR5 was 2+ for both (C) LoVo X 1.1 xenograft tumors and (D) D5124 xenograft tumors, using antibody LGR5.1-12. At the top of the panels shown in (C) are the percentages of cells in the field showing each level of staining.

H. Prevalence of LgR5 on Colon Tumors by Immunohistochemistry

To determine the prevalence of LgR5 in colon tumors, immunohistochemistry was performed on a tissue microarray containing cores from 143 different colon tumors, using antibody LGR5.1-12, as described above in Example (E).

Forty percent of the colon tumors were positive for LgR5, with 29% (41/143) scoring 1+, 9% (13/143) scoring 2+, and 2% (3/143) scoring 3+, using the following criteria:

0=no staining,

1+=weak staining,

2+=moderate staining, and

3+=strong staining.

The remaining colon tumors (86/143) scored 0 by IHC using antibody LGR5.1-12. FIG. 7A to D shows exemplary 0, 1+, 2+, and 3+ staining of colon tumors using antibody LGR5.1-12.

Substantial heterogeneity in IHC staining was observed. IHC was therefore performed on 19 colon cancer tumor sections using antibody LGR5.1-12. Three of the sections were negative for LgR5 expression; in two sections, greater than 50% of the cells were positive for LgR5; the remaining sections showed between 0 and 50% staining Table 3 shows the percentage of cells in each section that stained at each level, and the overall score using a 50% criteria (i.e., 50% or more of the cells are positive for LgR5) or a 10% criteria (i.e., 10% of the cells are positive for LgR5). For comparison, the staining observed in the D5124 and LoVo xengraft tumors described above are also included. H score is equal to (% cells staining at 1+)+(% cells staining at 2+)×2+(% cells staining at 3+)×3. H score takes into consideration the percentage of cells at each staining intensity.

TABLE 3

Immunohistochemistry of colon tumor sections using antibody LGR5.1-12

| Sample | 0 | +1 | +2 | +3 | H-score | Overall score (50% + criteria) | Overall score (10% + criteria) |
|---|---|---|---|---|---|---|---|
| HP-2889 | 40 | 45 | 15 | 0 | 75 | 1+ | 1+ |
| HP-9328 | 80 | 17 | 3 | 0 | 23 | 0 | 1+ |
| HP-11394 | 85 | 10 | 5 | 0 | 20 | 0 | 1+ |
| HP-19862 | 85 | 0 | 15 | 0 | 30 | 0 | 2+ |
| HP-19882 | 75 | 25 | 0 | 0 | 25 | 0 | 1+ |
| HP-20531 | 60 | 40 | 0 | 0 | 40 | 0 | 1+ |
| HP-21638 | 25 | 65 | 10 | 0 | 85 | 1+ | 1+ |
| HP-23099 | 85 | 15 | 0 | 0 | 15 | 0 | 1+ |
| HP-23301 | 15 | 20 | 65 | 0 | 150 | 2+ | 2+ |
| HP-23302 | 50 | 45 | 5 | 0 | 55 | 1+ | 1+ |
| HP-23433 | 55 | 5 | 35 | 5 | 90 | 0 | 2+ |
| HP-23451 | 95 | 5 | 0 | 0 | 5 | 0 | 0 |
| HP-24574 | 75 | 10 | 15 | 0 | 40 | 0 | 2+ |
| HP-24583 | 100 | 0 | 0 | 0 | 0 | 0 | 0 |
| HP-24586 | 85 | 10 | 5 | 0 | 20 | 0 | 1+ |
| HP-24589 | 100 | 0 | 0 | 0 | 0 | 0 | 0 |
| HP-24592 | 90 | 10 | 0 | 0 | 10 | 0 | 1+ |
| HP-24671 | 100 | 0 | 0 | 0 | 0 | 0 | 0 |
| HP-24672 | 95 | 5 | 0 | 0 | 5 | 0 | 0 |
| D5124 xeno model | 10 | 20 | 70 | 0 | 160 | 2+ | 2+ |
| LOVO xeno model | 45 | 20 | 25 | 10 | 100 | 2+ | 2+ |

These results demonstrate that antibody LGR5.1-12 is able to detect LgR5 expression in colon tumors. In summary, Lgr5 RNA and protein expression is observed within multiple normal tissue compartments and although heterogeneous, Lgr5 is expressed in colon tumors.

I. Immunohistochemistry with Antibody LGR5.26-1

Staining with antibody LGR5.26-1 was compared to staining with antibody LGR5.1-12 in CXF233 (human colon tumor model; Oncotest) xenograft tumors and in various colon cancer cell lines Immunohistochemistry (IHC) for Lgr5 was performed on a Dako Universal Autostainer (Dako, Carpinteria, Calif.). Briefly, formalin-fixed, paraffin-embedded tumor tissue were deparaffinized and antigen unmasking was performed in a PT Module (Thermo Scientific, Kalamazoo, Mich.) with Target Retrieval pH 6 (Dako) at 99° C. for 20 minutes. Endogenous peroxidase was inhibited with treatment of 3% $H_2O_2$ in PBS for 4 minutes and endogenous biotin was blocked using the Avidin/Biotin blocking kit (Vector Labs, Burlingame, Calif.). Endogenous IgGs were blocked using 10% donkey serum in 3% BSA/PBS and primary antibody to Lgr5 (LGR5.1-12 or 26-1) was incubated at 4 µg/ml for 60 minutes at room temperature. Biotinylated donkey anti-rabbit IgG (Jackson Immunoresearch, West Grove, Pa.) was incubated for 30 minutes at room temperature followed by treatment with Vectastain ABC Elite-HRP (Vector Labs) for 30 minutes at room temperature. Antibody binding was detected with Metal enhanced DAB (Pierce Rockford, Ill.) for 5 minutes at room temperature and sections were counterstained with Mayer's Hematoxylin (Rowley Biochemical, Danvers, Mass.).

As shown in FIG. 8, antibody LGR5.1-12 (A) and antibody LGR5.26-1 (B) shows similar staining patterns in a CXF233 xenograft tumor sample.

Each cell line was also characterized by lgr5 gene expression using RNAseq data into the following levels of expression: none, very low, low, moderate, and high. In addition, LgR5 levels were determined in the cell lines by IHC, substantially as described above. The results of that experiment are shown in Table 4.

TABLE 4

IHC staining of colon cancer cell lines using antibodies LGR5.1-12 and LGR5.26-1

| RNAseq expression | Cell Line | FACS | Ab1-12 | Ab26-1 |
|---|---|---|---|---|
| None | SW480 | | 0 | 0 |
| None | RKO | | 0 | 0 |
| None | COLO741 | | 0 | 0 |
| Very low | HCT-15 | | 0 | 0 |
| Very low | CX-1 | | 0 | 0 |
| Very low | HT-29 | | 0 | 0 |
| Very low | SW403 | | 2 + (60%) | 1 + (65%) |
| Low | SW1116 | | 0 | 0 |
| Low | HCA-7 | | 0 | 0 |
| Low | COLO-205 | | 0 | 0 |
| Low | LS180 | – | 0 | 1 + (10%) |
| Low | SW948 | | 1 + (15%) | 1 + (10%) |
| Moderate | CACO-2 | | 1 + (15%) | 1 + (15%) |
| Moderate | T84 | | 2 + (40%) | 2 + (40%) |
| Moderate | KM-12 | | 2 + (25%) | 1 + (60%) |
| Moderate | C2BBe1 | | 1 + (10%) | 1 + (15%) |
| High | DLD-1 | – | 0 | 1 + (10%) |
| High | SW620 | – | 0 | 1 + (20%) |
| High | SW1463 | +/– | 2 + (50%) | 2 + (25%) |
| High | SK-CO-1 | +/– | 2 + (80%) | 2 + (85%) |
| High | LS174T | – | 0 | 0 |
| High | LOVO | ++ | 2 + (50%) | 2 + (50%) |

Both antibody LGR5.1-12 and antibody LGR5.26-1 were able to detect LgR5 on the surface of many different colon cancer cell lines.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

| | TABLE OF SEQUENCES | | |
|---|---|---|---|
| SEQ ID NO | Description | | Sequence |
| 1 | αLgR5.1-12 light chain | | AYDMTQTPAS VEVAVGGTVT IKCQASQSIG SNLAWYQQKP GQPPKKLLIYG ASNLASGVSS RFKGSGSGTE FTLTISDLEC ADAATYYCQT TYGSSSDGFF WTFGGGTEVV VKGDPVAPTV LIFPPAADQV ATGTVTIVCV ANKYFPDVTV TWEVDGTTQT TGIENSKTPQ NSADCTYNLS STLTLTSTQY NSHKEYTCKV TQGTTSVVQS FNRGDC |
| 2 | αLgR5.1-12 heavy chain | | QSLEESGGGL VQPEGSLTLT CTASGFSFSR TYWICWDRQA PGKGLEWIAC IYAGGSDNTY YASWAKGRFT ISKTSSTTVT LQVTSLTAAD TATYFCARYY AGSSEYFNLW GPGTLVTVSS ASTKGPSVFP LAPCCGDTPS STVTLGCLVK GYLPEPVTVT WNSGTLTNGV RTFPSVRQSS GLYSLSSVVS VTSSSQPVTC |

-continued

| SEQ ID NO | Description | Sequence |
|---|---|---|
| | | NVAHPATNTK VDKTVAPSTC SKPTCPPPEL LGGPSVFIFP PKPKDTLMIS RTPEVTCVVV DVSQDDPEVQ FTWYINNEQV RTARPPLREQ QFNSTIRVVS TLPIAHQDWL RGKEFKCKVH NKALPAPIEK TISKARGQPL EPKVYTMGPP REELSSRSVS LTCMINGFYP SDISVEWEKN GKAEDNYKTT PAVLDSDGSY FLYSKLSVPT SEWQRGDVFT CSVMHEALHN HYTQKSISRS PGK |
| 3 | αLgR5.26-1 light chain | AFELTQTPSS VEAAVGGTVT IKCQASQSIS VGLAWYQQKP GQPPKLLIYK ASTLASGVPS RFKGSRSGTE FTLTISDLEC ADAATYYCQS YYDSSTTANV FGGGTEVVVK GDPVAPTVLI FPPAADQVAT GTVTIVCVAN KYFPDVTVTW EVDGTTQTTG IENSKTPQNS ADCTYNLSST LTLTSTQYNS HKEYTCKVTQ GTTSVVQSFN RGDC |
| 4 | αLgR5.26-1 heavy chain | QSLEESGGDL VKPGGTLTLT CTASGIDFSY YSYMCWVRQA PGKGLEWIAC IYAGTSGSTY YASWAKGRFT ISKTSSTTVT LQMISLTAAD TATYFCARSY YTFGVNGYAW DLWGPGTLVT VSSASTKGPS VFPLAPCCGD TPSSTVTLGC LVKGYLPEPV TVTWNSGTLT NGVRTFPSVR QSSGLYSLSS VVSVTSSSQP VTCNVAHPAT NTKVDKTVAP STCSKPTCPP PELLGGPSVF IFPPKPKDTL MISRTPEVTC VVVDVSQDDP EVQFTWYINN EQVRTARPPL REQQFNSTIR VVSTLPIAHQ DWLRGKEFKC KVHNKALPAP IEKTISKARG QPLEPKVYTM GPPREELSSR SVSLTCMING FYPSDISVEW EKNGKAEDNY KTTPAVLDSD GSYFLYSKLS VPTSEWQRGD VFTCSVMHEA LHNHYTQKSI SRSPGK |
| 5 | αLgR5.1-12 light chain variable region | AYDMTQTPAS VEVAVGGTVT IKCQASQSIG SNLAWYQQKP GQPPKLLIYG ASNLASGVSS RFKGSGSGTE FTLTISDLEC ADAATYYCQT TYGSSSDGFF WTFGGGTEVV VK |
| 6 | αLgR5.1-12 heavy chain variable region | QSLEESGGGL VQPEGSLTLT CTASGFSFSR TYWICWDRQA PGKGLEWIAC IYAGGSDNTY YASWAKGRFT ISKTSSTTVT LQVTSLTAAD TATYFCARYY AGSSEYFNLW GPGTLVTVSS |
| 7 | αLgR5.26-1 light chain variable region | AFELTQTPSS VEAAVGGTVT IKCQASQSIS VGLAWYQQKP GQPPKLLIYK ASTLASGVPS RFKGSRSGTE FTLTISDLEC ADAATYYCQS YYDSSTTANV FGGGTEVVVK |
| 8 | αLgR5.26-1 heavy chain variable region | QSLEESGGDL VKPGGTLTLT CTASGIDFSY YSYMCWVRQA PGKGLEWIAC IYAGTSGSTY YASWAKGRFT ISKTSSTTVT LQMISLTAAD TATYFCARSY YTFGVNGYAW DLWGPGTLVT VSS |
| 9 | αLgR5.1-12 HVR-L1 | QASQSIGSNL A |
| 10 | αLgR5.1-12 HVR-L2 | GASNLAS |
| 11 | αLgR5.1-12 HVR-L3 | QTTYGSSSDG FFWT |
| 12 | αLgR5.1-12 HVR-H1 | RTYWIC |
| 13 | αLgR5.1-12 HVR-H2 | CIYAGGSDNT YYASWAK |
| 14 | αLgR5.1-12 HVR-H3 | YYAGSSEYFN L |
| 15 | αLgR5.26-1 HVR-L1 | QASQSISVGL A |
| 16 | αLgR5.26-1 HVR-L2 | KASTLAS |
| 17 | αLgR5.26-1 HVR-L3 | QSYYDSSTTA NV |
| 18 | αLgR5.26-1 HVR-H1 | YYSYMC |

TABLE OF SEQUENCES

| SEQ ID NO | Description | Sequence |
|---|---|---|
| 19 | αLgR5.26-1 HVR-H2 | CIYAGTSGST YYASWAK |
| 20 | αLgR5.26-1 HVR-H3 | SYYTFGVNGY AWDL |
| 21 | Human LgR5 precursor; LGR5_human NP_003658 signal sequence = amino acids 1-21; 22 to 558 are extracellular domain (ECD) | MDTSRLGVLL SLPVLLQLAT GGSSPRSGVL LRGCPTHCHC EPDGRMLLRV DCSDLGLSEL PSNLSVFTSY LDLSMNNISQ LLPNPLPSLR FLEELRLAGN ALTYIPKGAF TGLYSLKVLM LQNNQLRHVP TEALQNLRSL QSLRLDANHI SYVPPSCFSG LHSLRHLWLD DNALTEIPVQ AFRSLSALQA MTLALNKIHH IPDYAFGNLS SLVVLHLHNN RIHSLGKKCF DGLHSLETLD LNYNNLDEFP TAIRTLSNLK ELGFHSNNIR SIPEKAFVGN PSLITIHFYD NPIQFVGRSA FQHLPELRTL TLNGASQITE FPDLTGTANL ESLTLTGAQI SSLPQTVCNQ LPNLQVDLS YNLLEDLPSF SVCQKLQKID LRHNEIYEIK VDTFQQLLSL RSLNLAWNKI AIIHPNAFST LPSLIKLDLS SNLLSSFPIT GLHGLTHLKL TGNHALQSLI SSENFPELKV IEMPYAYQCC AFGVCENAYK ISNQWNKGDN SSMDDLHKKD AGMFQAQDER DLEDFLLDFE EDLKALHSVQ CSPSPGPFKP CEHLLDGWLI RIGVWTIAVL ALTCNALVTS TVFRSPLYIS PIKLLIGVIA AVNMLTGVSS AVLAGVDAFT FGSFARHGAW WENGVGCHVI GFLSIFASES SVFLLTLAAL ERGFSVKYSA KFETKAPFSS LKVIILLCAL LALTMAAVPL LGGSKYGASP LCLPLPFGEP STMGYMVALI LLNSLCFLMM TIAYTKLYCN LDKGDLENIW DCSMVKHIAL LLFTNCILNC PVAFLSFSSL INLTFISPEV IKFILLVVVP LPACLNPLLY ILFNPHFKED LVSLRKQTYV WTRSKHPSLM SINSDDVEKQ SCDSTQALVT FTSSSITYDL PPSSVPSPAY PVTESCHLSS VAFVPCL |
| 22 | Human LgR5 mature, without signal sequence; amino acids 22 to 907 | GSSPRSGVL LRGCPTHCHC EPDGRMLLRV DCSDLGLSEL PSNLSVFTSY LDLSMNNISQ LLPNPLPSLR FLEELRLAGN ALTYIPKGAF TGLYSLKVLM LQNNQLRHVP TEALQNLRSL QSLRLDANHI SYVPPSCFSG LHSLRHLWLD DNALTEIPVQ AFRSLSALQA MTLALNKIHH IPDYAFGNLS SLVVLHLHNN RIHSLGKKCF DGLHSLETLD LNYNNLDEFP TAIRTLSNLK ELGFHSNNIR SIPEKAFVGN PSLITIHFYD NPIQFVGRSA FQHLPELRTL TLNGASQITE FPDLTGTANL ESLTLTGAQI SSLPQTVCNQ LPNLQVDLS YNLLEDLPSF SVCQKLQKID LRHNEIYEIK VDTFQQLLSL RSLNLAWNKI AIIHPNAFST LPSLIKLDLS SNLLSSFPIT GLHGLTHLKL TGNHALQSLI SSENFPELKV IEMPYAYQCC AFGVCENAYK ISNQWNKGDN SSMDDLHKKD AGMFQAQDER DLEDFLLDFE EDLKALHSVQ CSPSPGPFKP CEHLLDGWLI RIGVWTIAVL ALTCNALVTS TVFRSPLYIS PIKLLIGVIA AVNMLTGVSS AVLAGVDAFT FGSFARHGAW WENGVGCHVI GFLSIFASES SVFLLTLAAL ERGFSVKYSA KFETKAPFSS LKVIILLCAL LALTMAAVPL LGGSKYGASP LCLPLPFGEP STMGYMVALI LLNSLCFLMM TIAYTKLYCN LDKGDLENIW DCSMVKHIAL LLFTNCILNC PVAFLSFSSL INLTFISPEV IKFILLVVVP LPACLNPLLY ILFNPHFKED LVSLRKQTYV WTRSKHPSLM SINSDDVEKQ SCDSTQALVT FTSSSITYDL PPSSVPSPAY PVTESCHLSS VAFVPCL |
| 23 | Cynomolgus monkey LgR5 partial sequence, predicted; predicted to correspond to amino acids 33 to 907 of full-length precursor | GCPTHCHCEP DGRMLLRVDC SDLGLSELPS NLSVFTSYLD LSMNNISQLL PNPLPSLRFL EELRLAGNAL TYIPKGAFTG LYSLKVLMLQ NNQLRQVPTE ALQNLRSLQS LRLDANHISY VPPSCFSGLH SLRHLWLDDN ALTEIPVQAF RSLSALQAMT LALNKIHHIP DYAFGNLSSL VVLHLHNNRI HSLGKKCFDG LHSLETLDLN YNNLDEFPTA IRTLSNLKEL GFHSNNIRSI PEKAFVGNPS LITIHFYDNP IQFVGRSAFQ HLPELRILTL NGASQITEFP DLTGTANLES LTLIGAQISS LPQTVCNQLP NLQVDLSYN LLEDLPSFSV CQKLQKIDLR HNEIYEIKVD TFQQLLSRS LNLAWNKIAI IHPNAFSTLP SLIKLDLSSN LLSSFPVTGL HGLTHLKLTG NHALQSLISS ENFPELKIIE MPYAYQCCAF GVCENAYKIS NQWNKGDNSS MDDLHKKDAG MFQVQDERDL EDFLLDFEED LKALHSVQCS PSPGPFKPCE HLLDGWLIRI GVWTIAVLAL TCNALVTSTV FRSPLYISPI KLLIGVIAVV NMLTGVSSAV LAGVDAFTFG SFARHGAWWE NGVGCQVIGF LSIFASESSV FLLTLAALER GFSVKCSAKF ETKAPFSSLK VIILLCALLA LTMAAVPLLG GSEYGASPLC LPLPFGEPST TGYMVALILL NSLCFLMMTI AYTKLYCNLD KGDLENIWDC SMVKHIALLL FTNCILYCPV AFLSFSSLLN LTFISPEVIK FILLVIVPLP ACLNPLLYIL FNPHFKEDLV |

| SEQ ID NO | Description | Sequence |
|---|---|---|
| | | SLGKQTYFWT RSKHPSLMSI NSDDVEKQSC DSTQALVTFT SSSIAYDLPP SSVPSPAYPV TESCHLSSVA FVPCL |
| 24 | Rat LgR5 precursor; LGR5_rat NP_001100254; signal sequence = amino acids 1-21 | MDTSRVRMLL SLLALLQLVA AGSPPRPDTM PRGCPSYCHC ELDGRMLLRV DCSDLGLSEL PSNLSVFTSY LDLSMNNISQ LPASLLHRLR FLEELRLAGN ALTHIPKGAF AGLHSLKVLM LQNNQLRQVP EEALQNLRSL QSLRLDANHI SYVPPSCFSG LHSLRHLWLD DNALTDVPVQ AFRSLSALQA MTLALNKIHH IADHAFGNLS SLVVLHLHNN RIHSLGKKCF DGLHSLETLD LNYNNLDEFP TAIKTLSNLK ELGFHSNNIR SIPERAFVGN PSLITIHFYD NPIQFVGISA FQHLPELRTL TLNGASQITE FPDLTGTATL ESLILTGAKI SSLPQTVCDQ LPNLQVLDLS YNLLEDLPSL SGCQKLQKID LRHNEIYEIK GGTFQQLFNL RSLNLARNKI AIIHPNAFST LPSLIKLDLS SNLLSSFPVT GLHGLTHLKL TGNRALQSLI PSANFPELKI IEMPYAYQCC AFGGCENVYK IPNQWNKDDS SSVDDLRKKD AGLFQVQDER DLEDFLLDFE EDLKVLHSVQ CSPPPGPFKP CEHLFGSWLI RIGVWTTAVL ALSCNALVAF TVFRTPLYIS SIKLLIGVIA VVDILMGVSS AILAVVDTFT FGSFAQHGAW WEGGIGCQIV GFLSIFASES SVFLLTLAAL ERGFSVKCSS KFEMKAPLSS LKAIILLCVL LALTIATVPL LGGSEYNASP LCLPLPFGEP STTGYMVALV LLNSLCFLIM TIAYTRLYCS LEKGELENLW DCSMVKHTAL LLFTNCILYC PVAFLSFSSL LNLTFISPEV IKFILLVIVP LPACLNPLLY IVFNPHFKED MGSLGKQTRF WTRAKHPSLL SINSDDVEKR SCDSTQALVS FTHASIAYDL PSDSGSSPAY PMTESCHLSS VAFVPCL |
| 25 | RatLgR5 mature, without signal sequence; amino acids 22 to 907 | GSPPRPDTM PRGCPSYCHC ELDGRMLLRV DCSDLGLSEL PSNLSVFTSY LDLSMNNISQ LPASLLHRLR FLEELRLAGN ALTHIPKGAF AGLHSLKVLM LQNNQLRQVP EEALQNLRSL QSLRLDANHI SYVPPSCFSG LHSLRHLWLD DNALTDVPVQ AFRSLSALQA MTLALNKIHH IADHAFGNLS SLVVLHLHNN RIHSLGKKCF DGLHSLETLD LNYNNLDEFP TAIKTLSNLK ELGFHSNNIR SIPERAFVGN PSLITIHFYD NPIQFVGISA FQHLPELRTL TLNGASQITE FPDLTGTATL ESLILTGAKI SSLPQTVCDQ LPNLQVLDLS YNLLEDLPSL SGCQKLQKID LRHNEIYEIK GGTFQQLFNL RSLNLARNKI AIIHPNAFST LPSLIKLDLS SNLLSSFPVT GLHGLTHLKL TGNRALQSLI PSANFPELKI IEMPYAYQCC AFGGCENVYK IPNQWNKDDS SSVDDLRKKD AGLFQVQDER DLEDFLLDFE EDLKVLHSVQ CSPPPGPFKP CEHLFGSWLI RIGVWTTAVL ALSCNALVAF TVFRTPLYIS SIKLLIGVIA VVDILMGVSS AILAVVDTFT FGSFAQHGAW WEGGIGCQIV GFLSIFASES SVFLLTLAAL ERGFSVKCSS KFEMKAPLSS LKAIILLCVL LALTIATVPL LGGSEYNASP LCLPLPFGEP STTGYMVALV LLNSLCFLIM TIAYTRLYCS LEKGELENLW DCSMVKHTAL LLFTNCILYC PVAFLSFSSL LNLTFISPEV IKFILLVIVP LPACLNPLLY IVFNPHFKED MGSLGKQTRF WTRAKHPSLL SINSDDVEKR SCDSTQALVS FTHASIAYDL PSDSGSSPAY PMTESCHLSS VAFVPCL |
| 26 | Mouse LgR5 precursor; LGR5_mouse NP_034325; signal sequence = amino acids 1-21 | MDTSCVHMLL SLLALLQLVA AGSSPGPDAI PRGCPSHCHC ELDGRMLLRV DCSDLGLSEL PSNLSVFTSY LDLSMNNISQ LPASLLHRLC FLEELRLAGN ALTHIPKGAF TGLHSLKVLM LQNNQLRQVP EEALQNLRSL QSLRLDANHI SYVPPSCFSG LHSLRHLWLD DNALTDVPVQ AFRSLSALQA MTLALNKIHH IADYAFGNLS SLVVLHLHNN RIHSLGKKCF DGLHSLETLD LNYNNLDEFP TAIKTLSNLK ELGFHSNNIR SIPERAFVGN PSLITIHFYD NPIQFVGVSA FQHLPELRTL TLNGASHITE FPHLIGTAIL ESLILTGAKI SSLPQAVCDQ LPNLQVLDLS YNLLEDLPSL SGCQKLQKID LRHNEIYEIK GSTFQQLFNL RSLNLAWNKI AIIHPNAFST LPSLIKLDLS SNLLSSFPVT GLHGLTHLKL TGNRALQSLI PSANFPELKI IEMPSAYQCC AFGGCENVYK ISNQWNKDDG NSVDDLHKKD AGLFQVQDER DLEDFLLDFE EDLKALHSVQ CSPSPGPFKP CEHLFGSWLI RIGVWTTAVL ALSCNALVAL TVFRTPLYIS SIKLLIGVIA VVDILMGVSS AVLAAVDAFT FGRFAQHGAW WEDGIGCQIV GFLSIFASES SIFLLTLAAL ERGFSVKCSS KFEVKAPLFS LRAIVLLCVL LALTIATIPL LGGSKYNASP LCLPLPFGEP STTGYMVALV LLNSLCFLIM TIAYTKLYCS LEKGELENLW DCSMVKHIAL LLFANCILYC PVAFLSFSSL LNLTFISPDV IKFILLVIVP LPSCLNPLLY IVFNPHFKED MGSLGKHTRF WMRSKHASLL SINSDDVEKR SCESTQALVS FTHASIAYDL PSTSGASPAY PMTESCHLSS VAFVPCL |

-continued

| SEQ ID NO | Description | Sequence |
|---|---|---|
| 27 | Mouse LgR5 mature, without signal sequence; amino acids 22 to 907 | GSSPGPDAI PRGCPSHCHC ELDGRMLLRV DCSDLGLSEL PSNLSVFTSY LDLSMNNISQ LPASLLHRLC FLEELRLAGN ALTHIPKGAF TGLHSLKVLM LQNNQLRQVP EEALQNLRSL QSLRLDANHI SYVPPSCFSG LHSLRHLWLD DNALTDVPVQ AFRSLSALQA MTLALNKIHH IADYAFGNLS SLVVLHLHNN RIHSLGKKCF DGLHSLETLD LNYNNLDEFP TAIKTLSNLK ELGFHSNNIR SIPERAFVGN PSLITIHFYD NPIQFVGVSA FQHLPELRTL TLNGASHITE FPHLIGTAIL ESLILTGAKI SSLPQAVCDQ LPNLQVLDLS YNLLEDLPSL SGCQKLQKID LRHNEIYEIK GSTFQQLFNL RSLNLAWNKI AIIHPNAFST LPSLIKLDLS SNLLSSFPVT GLHGLTHLKL TGNRALQSLI PSANFPELKI IEMPSAYQCC AFGGCENVYK ISNQWNKDDG NSVDDLHKKD AGLFQVQDER DLEDFLLDFE EDLKALHSVQ CSPSPGPFKP CEHLFGSWLI RIGVWTTAVL ALSCNALVAL TVFRTPLYIS SIKLLIGVIA VVDILMGVSS AVLAAVDAFT FGRFAQHGAW WEDGIGCQIV GFLSIFASES SIFLLTLAAL ERGFSVKCSS KFEVKAPLFS LRAIVLLCVL LALTIATIPL LGGSKYNASP LCLPLPFGEP STTGYMVALV LLNSLCFLIM TIAYTKLYCS LEKGELENLW DCSMVKHIAL LLFANCILYC PVAFLSFSSL LNLTFISPDV IKFILLVIVP LPSCLNPLLY IVFNPHFKED MGSLGKHTRF WMRSKHASLL SINSDDVEKR SCESTQALVS FTHASIAYDL PSTSGASPAY PMTESCHLSS VAFVPCL |
| 28 | mu8E11 light chain variable region | NIVLTQSPAS LAVSLGQRAT ISCRASESVD NYGNSFMHWY QQKPGQPPKL LIYLASNLES GVPARFSGSG SRTDFTLTID PVEADDAATY YCQQNYEDPF TFGSGTKVEI KR |
| 29 | mu8E11 heavy chain variable region | QVQLQQSGTE LMKPGASVKI SCKATGYTFS AYWIEWIKQR PGHGLEWIGE ILPGSDSTDY NEKFKVKATF SSDTSSNTVY IQLNSLTYED SAVYYCARGG HYGSLDYWGQ GTTLKVSS |
| 30 | hu8E11.v1 light chain variable region | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KR |
| 31 | hu8E11.v1 heavy chain variable region | EVQLVQSGAE VKKPGASVKV SCKASGYTFS AYWIEWVRQA PGQGLEWIGE ILPGSDSTDY NEKFKVRVTI TSDTSTSTVY LELSSLRSED TAVYYCARGG HYGSLDYWGQ GTLVTVSS |
| 32 | hu8E11.v2 light chain variable region | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KR |
| 33 | hu8E11.v2 heavy chain variable region | EVQLVQSGAE VKKPGASVKV SCKASGYTFS AYWIEWVRQA PGQGLEWIGE ILPGSDSTDY NEKFKVRATF TSDTSTSTVY LELSSLRSED TAVYYCARGG HYGSLDYWGQ GTLVTVSS |
| 34 | hu8E11.v3 light chain variable region | DIVMTQSPDS LAVSLGERAT INCRASESVD NYGNSFMHWY QQKPGQPPKL LIYLASNLES GVPDRFSGSG SRTDFTLTIS SLQAEDVAVY YCQQNYEDPF TFGQGTKVEI KR |
| 35 | hu8E11.v3 heavy chain variable region | EVQLVQSGAE VKKPGASVKV SCKASGYTFS AYWIEWVRQA PGQGLEWIGE ILPGSDSTDY NEKFKVRVTI TSDTSTSTVY LELSSLRSED TAVYYCARGG HYGSLDYWGQ GTLVTVSS |
| 36 | hu8E11.v4 light chain variable region | DIVMTQSPDS LAVSLGERAT INCRASESVD NYGNSFMHWY QQKPGQPPKL LIYLASNLES GVPDRFSGSG SRTDFTLTIS SLQAEDVAVY YCQQNYEDPF TFGQGTKVEI KR |
| 37 | hu8E11.v4 heavy chain variable region | EVQLVQSGAE VKKPGASVKV SCKASGYTFS AYWIEWVRQA PGQGLEWIGE ILPGSDSTDY NEKFKVRATF TSDTSTSTVY LELSSLRSED TAVYYCARGG HYGSLDYWGQ GTLVTVSS |
| 38 | hu8E11.v5 light chain variable region | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KR |
| 39 | hu8E11.v5 heavy chain variable region | EVQLVQSGAE VKKPGASVKV SCKASGYTFS AYWIEWVRQA PGQGLEWIGE ILPGSDSTDY NEKFKVRVTI TRDTSTSTAY LELSSLRSED TAVYYCARGG HYGSLDYWGQ GTLVTVSS |

-continued

| SEQ ID NO | Description | Sequence |
|---|---|---|
| 40 | hu8E11.v6 light chain variable region | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KR |
| 41 | hu8E11.v6 heavy chain variable region | EVQLVQSGAE VKKPGASVKV SCKASGYTFS AYWIEWVRQA PGQGLEWIGE ILPGSDSTDY NEKFKVRVTI TADTSTSTAY LELSSLRSED TAVYYCARGG HYGSLDYWGQ GTLVTVSS |
| 42 | hu8E11.v7 light chain variable region | DIVMTQSPDS LAVSLGERAT INCRASESVD NYGNSFMHWY QQKPGQPPKL LIYLASNLES GVPDRFSGSG SRTDFTLTIS SLQAEDVAVY YCQQNYEDPF TFGQGTKVEI KR |
| 43 | hu8E11.v7 heavy chain variable region | EVQLVQSGAE VKKPGASVKV SCKASGYTFS AYWIEWVRQA PGQGLEWIGE ILPGSDSTDY NEKFKVRVTI TRDTSTSTAY LELSSLRSED TAVYYCARGG HYGSLDYWGQ GTLVTVSS |
| 44 | hu8E11.v8 light chain variable region | DIVMTQSPDS LAVSLGERAT INCRASESVD NYGNSFMHWY QQKPGQPPKL LIYLASNLES GVPDRFSGSG SRTDFTLTIS SLQAEDVAVY YCQQNYEDPF TFGQGTKVEI KR |
| 45 | hu8E11.v8 heavy chain variable region | EVQLVQSGAE VKKPGASVKV SCKASGYTFS AYWIEWVRQA PGQGLEWIGE ILPGSDSTDY NEKFKVRVTI TADTSTSTAY LELSSLRSED TAVYYCARGG HYGSLDYWGQ GTLVTVSS |
| 46 | mu3G12 light chain variable region | DVVMTQTPLS LPVSLGDQAS ISCRSSQSLV HSNGNTYLQW YLQKPGQSPK LLIYKVSNRF SGVPDRFSGS GSGTDFTLKI SRVEAEDLGI YFCSQSTHFP YTFGGGTKLE IKR |
| 47 | mu3G12 heavy chain variable region | QVQLQQPGAE MVKPGASVKL SCKASVDTFN SYWMHWVKQR PGQGLEWIGE INPSNGRTNY IEKFKNRATV TVDKSSSTAF MQLSSLTSED SAVYYCATGW YFDVWGAGTT VTVSS |
| 48 | mu2H6 light chain variable region | DIVMTQSPSS LTVTAGEKVT MSCKSSQSLL NSGNQKNYLT WFQQKPGQPP KLLIYWASTR ESGVPDRFTG SGSGTDFTLT ISNVQAEDLA VYYCQNDYSF PFTFGQGTKV EIKR |
| 49 | mu2H6 heavy chain variable region | EVQLQQSGPE LVKPGTSMKI SCKASGYSFT GYTMNWVKQS HKNGLEWIGL INCYNGGTNY NQKFKGKATL TVDKSSSTAF MELLSLTSED SAVYYCARGG STMITPRFAY WGQGTLVTVS S |
| 50 | YW353 light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIKR |
| 51 | YW353 heavy chain variable region | EVQLVESGGG LVQPGGSLRL SCAASGFTFT SYSISWVRQA PGKGLEWVAE IYPPGGYTDY ADSVKGRFTI SADTSKNTAY LQMNSLRAED TAVYYCAKAR LFFDYWGQGT LVTVSS |
| 52 | mu8E11 HVR L1 | RASESVDNYG NSFMH |
| 53 | mu8E11 HVR L2 | LASNLES |
| 54 | mu8E11 HVR L3 | QQNYEDPFT |
| 55 | mu8E11 HVR H1 | GYTFSAYWIE |
| 56 | mu8E11 HVR H2 | EILPGSDSTD YNEKFKV |
| 57 | mu8E11 HVR H3 | GGHYGSLDY |
| 58 | Hu8E11 light chain (LC) framework 1 (FR1) | DIVMTQSPDS LAVSLGERAT INC |
| 59 | Hu8E11 LC FR2 | WYQQKPGQPP KLLIY |

TABLE OF SEQUENCES

| SEQ ID NO | Description | Sequence |
|---|---|---|
| 60 | Hu8E11.v1 LC FR3<br>Hu8E11.v2 LC FR3<br>Hu8E11.v5 LC FR3<br>Hu8E11.v6 LC FR3 | GVPDRFSGSG SGTDFTLTIS SLQAEDVAVY YC |
| 61 | Hu8E11.v3 LC FR3<br>Hu8E11.v4 LC FR3<br>Hu8E11.v7 LC FR3<br>Hu8E11.v8 LC FR3 | GVPDRFSGSG SRTDFTLTIS SLQAEDVAVY YC |
| 62 | Hu8E11 LC FR4 | FGQGTKVEIK R |
| 63 | Hu8E11 heavy chain (HC) framework1 (FR1) | EVQLVQSGAE VKKPGASVKV SCKAS |
| 64 | Hu8E11 HC FR2 | WVRQAPGQGL EWIG |
| 65 | Hu8E11.v1 HC FR3<br>Hu8E11.v3 HC FR3 | RVTITSDTST STVYLELSSL RSEDTAVYYC AR |
| 66 | Hu8E11.v2 HC FR3<br>Hu8E11.v4 HC FR3 | RATFTSDTST STVYLELSSL RSEDTAVYYC AR |
| 67 | Hu8E11.v5 HC FR3<br>Hu8E11.v7 HC FR3 | RVTITRDTST STAYLELSSL RSEDTAVYYC AR |
| 68 | Hu8E11.v6 HC FR3<br>Hu8E11.v8 HC FR3 | RVTITADTST STAYLELSSL RSEDTAVYYC AR |
| 69 | Hu8E11 HC FR4 | WGQGTLVTVS S |
| 70 | mu3G12 HVR L1 | RSSQSLVHSN GNTYLQ |
| 71 | mu3G12 HVR L2 | KVSNRFS |
| 72 | mu3G12 HVR L3 | SQSTHFPYT |
| 73 | mu3G12 HVR H1 | VDTFNSYWMH |
| 74 | mu3G12 HVR H2 | EINPSNGRTN YIEKFKN |
| 75 | mu3G12 HVR H3 | GWYFDV |
| 76 | mu2H6 HVR L1 | KSSQSLLNSG NQKNYLT |
| 77 | mu2H6 HVR L2 | WASTRES |
| 78 | mu2H6 HVR L3 | QNDYSFPFT |
| 79 | mu2H6 HVR H1 | GYSFTGYTMN |
| 80 | mu2H6 HVR H2 | LINCYNGGTN YNQKFKG |
| 81 | mu2H6 HVR H3 | GGSTMITPRF AY |
| 82 | YW353 HVR L1 | RASQDVSTAV A |

| SEQ ID NO | Description | Sequence |
|---|---|---|
| 83 | YW353 HVR L2 | SASFLYS |
| 84 | YW353 HVR L3 | QQSYTTPPT |
| 85 | YW353 HVR H1 | GFTFTSYSIS |
| 86 | YW353 HVR H2 | EIYPPGGYTD YADSVKG |
| 87 | YW353 HVR H3 | ARLFFDY |
| 88 | hu8E11.v2 light chain | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 89 | hu8E11.v2 heavy chain | EVQLVQSGAE VKKPGASVKV SCKASGYTFS AYWIEWVRQA PGQGLEWIGE ILPGSDSTDY NEKFKVRATF TSDTSTSTVY LELSSLRSED TAVYYCARGG HYGSLDYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 90 | YW353 light chain | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 91 | YW353 heavy chain | EVQLVESGGG LVQPGGSLRL SCAASGFTFT SYSISWVRQA PGKGLEWVAE IYPPGGYTDY ADSVKGRFTI SADTSKNTAY LQMNSLRAED TAVYYCAKAR LFFDYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 92 | Antisense forward primer | ACCAACTGCATCCTAAACTG |
| 93 | Antisense reverse primer | ACCGAGTTTCACCTCAGCTC |
| 94 | Sense forward primer | ACATTGCCCTGTTGCTCTTC |
| 95 | Sense reverse primer | ACTGCTCTGATATACTCAATC |
| 96 | LgR5 ECD huFc (1 to 537 are LgR5 ECD) | GSSPRSGVLL RGCPTHCHCE PDGRMLLRVD CSDLGLSELP SNLSVFTSYL DLSMNNISQL LPNPLPSLRF LEELRLAGNA LTYIPKGAFT GLYSLKVLML QNNQLRHVPT EALQNLRSLQ SLRLDANHIS YVPPSCFSGL HSLRHLWLDD NALTEIPVQA FRSLSALQAM TLALNKIHHI PDYAFGNLSS LVVLHLHNNR IHSLGKKCFD GLHSLETLDL NYNNLDEFPT AIRTLSNLKE LGFHSNNIRS IPEKAFVGNP SLITIHFYDN PIQFVGRSAF QHLPELRTLT LNGASQITEF PDLTGTANLE SLTLTGAQIS SLPQTVCNQL PNLQVLDLSY NLLEDLPSFS VCQKLQKIDL RHNEIYEIKV DTFQQLLSLR SLNLAWNKIA IIHPNAFSTL PSLIKLDLSS NLLSSFPITG LHGLTHLKLT GNHALQSLIS SENFPPELKV IEMPYAYQCCA FGVCENAYKI SNQWNKGDNS |

TABLE OF SEQUENCES

| SEQ ID NO | Description | Sequence |
|---|---|---|
| | | SMDDLHKKDA GMFQAQDERD LEDFLLDFEE DLKALHSVQC SPSPGPFKPC EHLLDGWGRA QVTDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |

What is claimed is:

1. An isolated antibody that binds LgR5, wherein the antibody comprises hypervariable regions (HVRs) selected from:
   a) (i) HVR-H1 comprising the amino acid sequence of SEQ TD NO: 12; (ii) HVR-H2 comprising the amino acid sequence of SEQ ID NO: 13; (iii) HVR-H3 comprising the amino acid sequence of SEQ ID NO: 14; (iv) HVR-L1 comprising the amino acid sequence of SEQ ID NO: 9; (v) HVR-L2 comprising the amino acid sequence of SEQ ID NO: 10; and (vi) HVR-L3 comprising the amino acid sequence of SEQ ID NO: 11; or
   b) (i) HVR-H1 comprising the amino acid sequence of SEQ ID NO: 18; (ii) HVR-H2 comprising the amino acid sequence of SEQ ID NO: 19; (iii) HVR-H-3 comprising the amino acid sequence of SEQ ID NO: 20; (iv) HVR-L 1 comprising the amino acid sequence of SEQ ID NO: 15; (v) HVR-L2 comprising the amino acid sequence of SEQ ID NO: 16; and (vi) HVR-L3 comprising the amino acid sequence of SEQ ID NO: 17.

2. The antibody of claim 1, comprising
   (i) HVR-H1 comprising the amino acid sequence of SEQ ID NO: 12; (ii) HVR-H2 comprising the amino acid sequence of SEQ II) NO: 13; (iii) HVR-H3 comprising the amino acid sequence of SEQ ID NO: 14; (iv) HVR-L1 comprising the amino acid sequence of SEQ ID NO: 9; (v) HVR-L2 comprising the amino acid sequence of SEQ ID NO: 10; and (vi) HVR-L3 comprising the amino acid sequence of SEQ ID NO: 11.

3. The antibody of claim 1, comprising:
   a) (i) a VH sequence having at least 95% sequence identity to the amino acid sequence of SEQ ID NO: 6; (n) a VL sequence having at least 95% sequence identity to the amino acid sequence of SEQ ID NO: 5; or (iii) a VH sequence as in (i) and a VL sequence as in (ii); or
   b) (i) a VH sequence having at least 95% sequence identity to the amino acid sequence of SEQ ID NO: 8; (ii) a VL sequence having at least 95% sequence identity to the amino acid sequence of SEQ ID NO: 7; or (iii) a VH sequence as in (i) and a VL sequence as in (ii).

4. The antibody of claim 1, comprising:
   a) a VH sequence of SEQ ID NO: 6 or SEQ ID NO: 8;
   b) a VL sequence of SEQ ID NO: 7 or SEQ ID NO: 5;
   c) a VH sequence of SEQ ID NO: 6 and a VL sequence of SEQ ID NO: 5; or
   d) a VI sequence of SEQ ID NO: 8 and a VL sequence of SEQ ID NO: 7.

5. The antibody of claim 1, which is a monoclonal antibody.

6. The antibody of claim 5, which is a rabbit, humanized, or chimeric antibody.

7. The antibody of claim 5, which is an IgG selected from IgG1, IgG2a, IgG2b, IgG3, and IgG4.

8. The antibody of claim 1, wherein the antibody competes for binding to LgR5 with antibody huYW353 and antibody 8E11.

9. The antibody of claim 1, wherein the antibody does not compete for binding to LgR5 with either antibody huYW353 or antibody 8E11.

10. An immunoconjugate comprising the antibody of claim 1 and a cytotoxic agent.

11. A pharmaceutical formulation comprising the immunoconjugate of claim 10 and a pharmaceutically acceptable carrier.

12. The antibody of claim 1 conjugated to a label.

13. The antibody of claim 12, wherein the label is a positron emitter.

14. The antibody of claim 13, wherein the positron emitter is $^{89}$Zr.

15. The antibody of claim 1, comprising (i) HVR-H1 comprising the amino acid sequence of SEQ ID NO: 18; (ii) HVR-H2 comprising the amino acid sequence of SEQ ID NO: 19; (iii) HVR-H3 comprising the amino acid sequence of SEQ ID NO: 20; (iv) HVR-L 1 comprising the amino acid sequence of SEQ ID NO: 15; (v) HVR-L2 comprising the amino acid sequence of SEQ ID NO: 16; and (vi) HVR-L3 comprising the amino acid sequence of SEQ ID NO: 17.

16. An isolated antibody that binds LgR5, wherein the antibody comprises:
    a) a VH sequence of SEQ ID NO: 6 and a VL sequence of SEQ ID NO: 5; or
    b) a VH sequence of SEQ ID NO: 8 and a VL sequence of SEQ ID NO: 7.

17. The antibody of claim 16, comprising a VH sequence of SEQ ID NO: 6 and a VL sequence of SEQ ID NO: 5.

18. The antibody of claim 16, comprising a VH sequence of SEQ ID NO: 8 and a VL sequence of SEQ ID NO: 7.

19. The antibody of claim 1, wherein the antibody is capable of specifically staining LgR5 on the surface of human intestinal crypt cells by immunohistochemistry.

20. A method of detecting human LgR5 in a biological sample comprising contacting the biological sample with the anti-LgR5 antibody of claim 1 under conditions permissive for binding of the anti-LgR5 antibody to human LgR5, and detecting whether a complex is formed between the anti-LgR5 antibody and human LgR5 in the biological sample.

21. The method of claim 20, wherein the anti-LgR5 antibody comprises:
    a) a VH sequence of SEQ ID NO: 6 or SEQ ID NO: 8;
    b) a VL sequence of SEQ ID NO: 7 or SEQ ID NO: 5;
    c) a VH sequence of SEQ ID NO: 6 and a VL sequence of SEQ ID NO: 5; or
    d) a VH sequence of SEQ ID NO: 8 and a VL sequence of SEQ ID NO: 7.

22. The method of claim 20, wherein the biological sample is a colon cancer sample, a colorectal cancer sample, a small intestine cancer sample, an endometrial cancer sample, a pancreatic cancer sample, or an ovarian cancer sample.

23. A method for detecting a LgR5-positive cancer comprising (i) administering a labeled anti-LgR5 antibody to a subject having or suspected of having a LgR5-positive cancer, wherein the labeled anti-LgR5 antibody comprises the anti-LgR5 antibody of claim 1, and (ii) detecting the labeled anti-LgR5 antibody in the subject, wherein detection of the labeled anti-LgR5 antibody indicates a LgR5-positive cancer in the subject.

24. The method of claim 23, wherein the labeled anti-LgR5 antibody comprises:
    a) a VH sequence of SEQ ID NO: 6 or SEQ ID NO: 8;
    a) a VL sequence of SEQ ID NO: 7 or SEQ ID NO: 5;
    a) a VH sequence of SEQ ID NO: 6 and a VL sequence of SEQ II NO: 5; or
    a) a VH sequence of SEQ ID NO: 8 and a VL sequence of SEQ ID NO: 7.

25. A method of identifying a cancer patient as having a LgR5-positive cancer, comprising contacting a cancer sample from the patient with the anti-LgR5 antibody of claim 1 under conditions permissive for binding of the anti-LgR5 antibody to human LgR5, and detecting whether a complex is formed between the anti-LgR5 antibody and human LgR5 in the cancer sample, wherein detection of the complex indicates an LgR5-positive cancer.

26. A method of selecting a cancer patient for treatment with an immunoconjugate comprising an anti-LgR5 antibody, comprising detecting the level of LgR5 expression in a cancer sample from the patient using immunohistochemistry (IHC), wherein an elevated level of LgR5 expression relative to a control level of LgR5 expression indicates that the cancer patient is more likely to benefit from treatment with an immunoconjugate comprising an anti-LgR5 antibody, wherein the IHC is performed using the antibody of claim 1, and wherein the anti-LgR5 antibody of the immunoconjugate comprises:
    a) HVR-H1 comprising the amino acid sequence of SEQ ID NO: 55, HVR-H2 comprising the amino acid sequence of SEQ ID NO: 56, HVR-H3 comprising the amino acid sequence of SEQ ID NO: 57, HVR-L1 comprising the amino acid sequence of SEQ ID NO: 52; HVR-L2 comprising the amino acid sequence of SEQ ID NO: 53; and HVR-L3 comprising the amino acid sequence of SF ID NO: 54; or
    b) HVR-H1 comprising the amino acid sequence of SEQ ID NO: 73, HVR-H2 comprising the amino acid sequence of SEQ ID NO: 74, HVR-H3 comprising the amino acid sequence of SEQ ID NO: 75, HVR-L1 comprising the amino acid sequence of SEQ ID NO: 70; HVR-L2 comprising the amino acid sequence of SEQ ID NO: 71; and HVR-L3 comprising the amino acid sequence of SEQ ID NO: 72; or
    c) HVR-H1 comprising the amino acid sequence of SEQ ID NO: 79, HVR-H2 comprising the amino acid sequence of SEQ ID NO: 80, HVR-H3 comprising the amino acid sequence of SEQ ID NO: 81, HVR-L1 comprising the amino acid sequence of SEQ ID NO: 76: HVR-L2 comprising the amino acid sequence of SEQ ID NO: 77; and HVR-L3 comprising the amino acid sequence of SEQ ID NO: 78; or
    d) HVR-H1 comprising the amino acid sequence of SEQ ID NO: 85, HVR-H2 comprising the amino acid sequence of SEQ ID NO: 86, HVR-H3 comprising the amino acid sequence of SEQ ID NO: 87, HVR-L1 comprising the amino acid sequence of SEQ ID NO: 82; HVR-L2 comprising the amino acid sequence of SEQ ID NO: 83; and HVR-L3 comprising the amino acid sequence of SEQ ID NO: 84; or
    e) a VH sequence of SEQ ID NO: 33 and a VL sequence of SEQ ID NO: 32; or
    f) a VH sequence of SEQ ID NO: 51 and a VL sequence of SEQ ID NO: 50.

27. A method of selecting a cancer patient for treatment with an immunoconjugate comprising an anti-LgR5 antibody, comprising contacting a cancer sample from the patient with the anti-LgR5 antibody of claim 1 under conditions permissive for binding of the anti-LgR5 antibody to human LgR5, detecting whether a complex is formed between the anti-LgR5 antibody and human LgR5 in the cancer sample, and selecting the patient for treatment if the complex is detected, wherein the anti-LgR5 antibody of the immunoconjugate comprises:

a) HVR-H1 comprising the amino acid sequence of SEQ ID NO: 55, HVR-112 comprising the amino acid sequence of SEQ ID NO: 56, HVR-H3 comprising the amino acid sequence of SEQ ID NO: 57, HVR-L1 comprising the amino acid sequence of SEQ ID NO: 52; HVR-L2 comprising the amino acid sequence of SEQ ID NO: 53; and HVR-L3 comprising the amino acid sequence of SEQ ID NO: 54; or
b) HVR-H1 comprising the amino acid sequence of SEQ ID NO: 73, HVR-H2 comprising the amino acid sequence of SEQ ID NO: 74, HVR-H3 comprising the amino acid sequence of SEQ ID NO: 75, HVR-L1 comprising the amino acid sequence of SEQ ID NO: 70; HVR-L2 comprising the amino acid sequence of SEQ ID NO: 71; and HVR-L3 comprising the amino acid sequence of SEQ ID NO: 72; or
c) HVR-H1 comprising the amino acid sequence of SEQ ID NO: 79, HVR-H2 comprising the amino acid sequence of SEQ ID NO: 80, HVR-H3 comprising the amino acid sequence of SEQ ID NO: 81, HVR-L1 comprising the amino acid sequence of SEQ ID NO: 76; HVR-L2 comprising the amino acid sequence of SEQ ID NO: 77; and HVR-L3 comprising the amino acid sequence of SEQ ID NO: 78; or
d) HVR-H1 comprising the amino acid sequence of SEQ ID NO: 85, HVR-H2 comprising the amino acid sequence of SEQ ID NO: 86, HVR-H3 comprising the amino acid sequence of SEQ ID NO: 87, HVR-L1 comprising the amino acid sequence of SEQ ID NO: 82; HVR-L2 comprising the amino acid sequence of SEQ ID NO: 83; and HVR-L3 comprising the amino acid sequence of SEQ ID NO: 84; or
e) a VH sequence of SEQ ID NO: 33 and a VL sequence of SEQ ID NO: 32; or
f) a VH sequence of SEQ ID NO: 51 and a VL sequence of SEQ ID NO: 50.

28. A method of treating a cancer patient comprising determining that a cancer sample from the patient has an elevated level of LgR5 expression relative to a control level by immunohistochemistry (IHC) using the antibody of claim 1 and administering to the patient a therapeutically effective amount of an immunoconjugate comprising an anti-LgR5 antibody conjugated to a cytotoxic agent, wherein the anti-LgR5 antibody of the immunoconjugate comprises:
a) HVR-H1 comprising the amino acid sequence of SEQ ID NO: 55, HVR-H2 comprising the amino acid sequence of SEQ ID NO: 56, HVR-H3 comprising the amino acid sequence of SEQ ID NO: 57, HVR-L1 comprising the amino acid sequence of SEQ ID NO: 52; HVR-L2 comprising the amino acid sequence of SEQ ID NO: 53; and HVR-L3 comprising the amino acid sequence of SEQ ID NO: 54; or
b) HVR-1L comprising the amino acid sequence of SEQ ID NO: 73, HVR-112 comprising the amino acid sequence of SEQ ID NO: 74, HVR-H3 comprising the amino acid sequence of SEQ ID NO: 75, HVR-L1 comprising the amino acid sequence of SEQ ID NO: 70; HVR-L2 comprising the amino acid sequence of SEQ ID NO: 71; and HVR-L3 comprising the amino acid sequence of SEQ ID NO: 72; or
c) HVR-H1 comprising the amino acid sequence of SEQ ID NO: 79, HVR-H2 comprising the amino acid sequence of SEQ ID NO: 80, HVR-H3 comprising the amino acid sequence of SEQ ID NO: 81, HVR-L1 comprising the amino acid sequence of SEQ ID NO: 76: HVR-L2 comprising the amino acid sequence of SEQ ID NO: 77; and HVR-L3 comprising the amino acid sequence of SEQ ID NO: 78; or
d) HVR-H1 comprising the amino acid sequence of SEQ ID NO: 85, HVR-H2 comprising the amino acid sequence of SEQ ID NO: 86, HVR-H3 comprising the amino acid sequence of SEQ ID NO: 87, HVR-L1 comprising the amino acid sequence of SEQ ID NO: 82: HVR-L2 comprising the amino acid sequence of SEQ ID NO: 83; and HVR-L3 comprising the amino acid sequence of SEQ ID NO: 84; or
e) a VH sequence of SEQ ID NO: 33 and a VL sequence of SEQ ID NO: 32; or
f) a VH sequence of SEQ ID NO: 51 and a VL sequence of SEQ ID NO: 50.

29. The method of claim 28, wherein the cancer sample is a colon cancer sample, a colorectal cancer sample, a small intestine cancer sample, an endometrial cancer sample, a pancreatic cancer sample, or an ovarian cancer sample.

30. The method of claim 25, wherein the anti-LgR5 antibody comprises:
a) a VH sequence of SEQ ID NO: 6 or SEQ TI NO: 8;
b) a VL sequence of SEQ ID NO: 7 or SEQ ID NO: 5;
c) a VH sequence of SEQ ID NO: 6 and a VL sequence of SEQ ID NO: 5; or
d) a VH sequence of SEQ ID NO: 8 and a VL sequence of SEQ ID NO: 7.

31. The method of claim 26, wherein the anti-LgR5 antibody used to perform IHC comprises:
a) a VH sequence of SEQ ID NO: 6 or SEQ ID NO: 8;
b) a VL sequence of SEQ ID NO: 7 or SEQ ID NO: 5;
c) a VH sequence of SEQ ID NO: 6 and a VL sequence of SEQ ID NO: 5; or
d) a VH sequence of SEQ ID NO: 8 and a VL sequence of SEQ ID NO: 7.

32. The method of claim 27, wherein the anti-LgR5 antibody used to contact the cancer sample comprises:
a) a VH sequence of SEQ ID NO: 6 or SEQ ID NO: 8;
b) a VL sequence of SEQ ID NO: 7 or SEQ ID NO: 5;
c) a VH sequence of SEQ ID NO: 6 and a VL sequence of SEQ ID NO: 5, or
d) a VH sequence of SEQ IT NO: 8 and a VL sequence of SEQ ID NO: 7.

33. The method of claim 28, wherein the antibody used to perform IHC comprises:
a) a VH sequence of SEQ ID NO: 6 or SEQ ID NO: 8;
b) a VL sequence of SEQ ID NO: 7 or SEQ ID NO: 5;
c) a VH sequence of SEQ ID NO: 6 and a VL sequence of SEQ ID NO: 5; or
d) a VH sequence of SEQ ID NO: 8 and a VL sequence of SEQ ID NO: 7.

\* \* \* \* \*